(12) United States Patent
Hennequin et al.

(10) Patent No.: US 7,173,135 B2
(45) Date of Patent: Feb. 6, 2007

(54) SUBSTITUTED 3-CYANOQUINOLINES AS MEK INHIBITORS

(75) Inventors: Laurent Francois Andre Hennequin, Macclesfield (GB); Keith Hopkinson Gibson, Macclesfield (GB); Kevin Michael Foote, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/520,468

(22) PCT Filed: Jul. 4, 2003

(86) PCT No.: PCT/GB03/02882

§ 371 (c)(1),
(2), (4) Date: Jan. 7, 2005

(87) PCT Pub. No.: WO2004/005284

PCT Pub. Date: Jan. 15, 2004

(65) Prior Publication Data

US 2006/0089382 A1    Apr. 27, 2006

(30) Foreign Application Priority Data

Jul. 9, 2002    (GB) ................... 0215823.6

(51) Int. Cl.
*C07D 215/38* (2006.01)
*C07D 215/44* (2006.01)

(52) U.S. Cl. ............... 546/153; 546/159; 514/311; 514/312; 514/313

(58) Field of Classification Search ........... 546/153, 546/159; 514/311, 312, 313
See application file for complete search history.

(56) References Cited

U.S. PATENT DOCUMENTS

| | | | |
|---|---|---|---|
| 3,376,195 A | 4/1968 | Allais et al. .................. 514/310 |
| 3,936,461 A | 2/1976 | Schwender et al. ........... 546/90 |
| 4,421,920 A | 12/1983 | Baudouin et al. ............ 546/163 |
| 5,409,930 A | 4/1995 | Spada et al. ................. 514/248 |
| 5,650,415 A | 7/1997 | Tang et al. .................. 514/312 |
| 5,656,643 A | 8/1997 | Spada et al. ................. 514/312 |
| RE36,256 E | 7/1999 | Spada et al. ................. 514/249 |
| 6,002,008 A | 12/1999 | Wissner et al. .............. 546/160 |
| 6,630,489 B1 * | 10/2003 | Crawley ..................... 514/311 |
| 6,638,945 B1 * | 10/2003 | Gibson ....................... 514/311 |
| 6,809,106 B1 * | 10/2004 | Gibson ....................... 514/311 |

FOREIGN PATENT DOCUMENTS

| | | |
|---|---|---|
| EP | 0326330 | 8/1989 |
| EP | 0607439 | 7/1994 |
| FR | 2077455 | 9/1969 |
| WO | WO 93/03030 | 2/1993 |
| WO | WO 96/09294 | 3/1996 |
| WO | WO 97/03069 | 1/1997 |
| WO | WO 97/17329 | 5/1997 |
| WO | WO 98/02434 | 1/1998 |
| WO | WO 99/35146 | 7/1999 |
| WO | 00/18761 A | 4/2000 |
| WO | WO 00/18761 | 4/2000 |
| WO | WO 00/68199 | 11/2000 |
| WO | WO 00/68200 | 11/2000 |
| WO | WO 00/68201 | 11/2000 |
| WO | WO 01/94341 | 12/2001 |
| WO | WO 02/16352 | 2/2002 |
| WO | WO 02/36570 | 5/2002 |
| WO | WO 02/44166 | 6/2002 |
| WO | WO 02/085895 | 10/2002 |
| WO | 03/008409 A | 1/2003 |
| WO | WO 03/008409 | 1/2003 |
| WO | WO 03/047582 | 6/2003 |
| WO | WO 03/047583 | 6/2003 |
| WO | WO 03/047585 | 6/2003 |
| WO | WO 03/053960 | 7/2003 |
| WO | WO 2004/004732 | 1/2004 |

* cited by examiner

*Primary Examiner*—D. Margaret Seaman
(74) *Attorney, Agent, or Firm*—Morgan Lewis & Bockius LLP

(57) ABSTRACT

The invention concerns quinoline derivatives of Formula (I) wherein each of $Z^1$, m, $R^1$, n, $R^3$, $Z^2$ and $R^{14}$ have any of the meanings defined hereinbefore in the description; processes for their preparation, pharmaceutical compositions containing them and their use in the manufacture of a medicament for use as an anti-invasive or anti-proliferative agent in the containment and/or treatment of solid tumour disease.

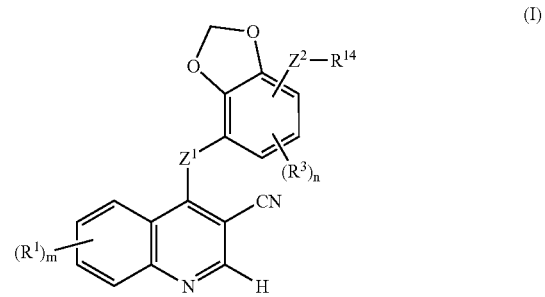

(I)

11 Claims, No Drawings

SUBSTITUTED 3-CYANOQUINOLINES AS MEK INHIBITORS

The invention concerns certain novel quinoline derivatives, or pharmaceutically-acceptable salts thereof, which possess anti-tumour activity and are accordingly useful in methods of treatment of the human or animal body. The invention also concerns processes for the manufacture of said quinoline derivatives, pharmaceutical compositions containing them and their use in therapeutic methods, for example in the manufacture of medicaments for use in the prevention or treatment of solid tumour disease in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Oncogenes give rise to the production of peptides which are receptors for growth factors. Activation of the growth factor receptor complex subsequently leads to an increase in cell proliferation. Oncogenes often encode abnormal versions of signal pathway components, such as receptor tyrosine kinases, serine-threonine kinases, or downstream signaling molecules such as the ras genes. The ras genes code for closely related small guanine nucleotide binding proteins which hydrolyse bound guanosine triphosphate (GTP) to guanosine diphosphate (GDP). Ras proteins are active in promoting cell growth and transformation when they are bound to GTP and inactive when they are bound to GDP. Transforming mutants of p21ras are defective in their GTPase activity and hence remain in the active GTP bound state. The ras oncogene is known to play an integral role in certain cancers and has been found to contribute to the formation of over 20% of all cases of human cancer.

When activated by ligand such as a growth factor, cell surface receptors which are coupled to the mitogenic response can initiate a chain of reactions which leads to the activation of guanine nucleotide exchange activity on ras proteins. When ras protein is in its active GTP-bound state, a number of other proteins interact directly with ras at the plasma membrane resulting in signal transmission through several distinct pathways. The best characterised effector protein is the product of the raf proto-oncogene. The interaction of raf and ras is a key regulatory step in the control of cell proliferation. Ras-mediated activation of the raf serine-threonine kinase in turn activates the dual-specificity MEK (MEK1 and MEK2), which is the immediate upstream activator of mitogen activated protein kinase (MAPKs known as extracellular signal regulated protein kinases or ERK1 and ERK2). To date, no substrates of MEK other than MAPK have been identified, though recent reports indicate that MEK may also be activated by other upstream signal proteins such as MEKK1 and Cot/Tpl-2. Activated MAPK translocates and accumulates in the nucleus, where it can phosphorylate and activate transcription factors such as Elk-1 and Sap1a, leading to the enhanced expression of genes such as c-fos.

The ras-dependent raf-MEK-MAPK cascade: is one of the key signalling pathways responsible for transmitting and amplifying mitogenic signals from cell surface to the nucleus resulting in changes in gene expression and cell fate. This ubiquitous pathway appears essential for normal-cell proliferation and constitutive activation of this pathway is sufficient to induce cellular transformation. Transforming mutants of p21ras are constitutively active, resulting in raf, MEK and MAPK activity and cell transformation. Inhibition of MEK activity using either antisense raf, a dominant negative MEK mutant or the selective inhibitor PD098059 has been shown to block the growth and morphological transformation of ras-transformed fibroblasts.

The mechanism of activation of raf, MEK and MAPK is through phosphorylation on specific serine, threonine or tyrosine residues. Activated raf and other kinases phosphorylate MEK1 on S218 and S222 and MEK2 on S222 and S226. This results in MEK activation and subsequent phosphorylation and activation of ERK1 on T190 and Y192 and ERK2 on T183 and Y185 by the dual specificity MEKs. Whilst MEK can be activated by a number of protein kinases, and active MAPKs phosphorylate and activate a number of substrate proteins including transcription factors and other protein kinases, MEKs appear specific and sole activators of MAPKs and could act as a focal point for cross-cascade regulation. MEK1 and MEK2 isoforms show unusual specificity and also contain a proline-rich insert between catalytic subdomains IX and X which is not present in any of the other known MEK family members. These differences between MEK and other protein kinases, together with the known role of MEK (MEK 1, MEK 2) and, more recently MEK 5, in proliferative signalling suggest it may be possible to discover and employ selective MEK inhibitors as therapeutic agents for use in proliferative disease.

Accordingly, it has been recognised that an inhibitor of the MAPK kinase pathway should be of value as an antiproliferative agent for use in the containment and/or treatment of solid tumour disease.

It is also known that several oncogenes encode tyrosine kinase enzymes and that certain growth factor receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example pp60$^{v\text{-}Src}$ tyrosine kinase (otherwise known as v-Src), and the corresponding tyrosine kinases in normal cells, for example pp60$^{c\text{-}Src}$ tyrosine kinase (otherwise known as c-Src).

Receptor tyrosine kinases are important in the transmission of biochemical signals which initiate cell replication. Some of them are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43–73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGFI receptors and insulin-related receptor (IRR) and Class III receptor tyrosine kinases comprising the platelet-derived growth factor (PDGF) family of receptor tyrosine kinases such as the PDGFα, PDGFβ and colony-stimulating factor 1 (CSF1) receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth (Ullrich et al., *Cell*, 1990, 61, 203–212, Bolen et al., *FASEB J.*, 1992, 6, 3403–3409, Brickell et al., *Critical Reviews in Oncogenesis*, 1992, 3, 401–406, Bohlen et al., *Oncogene*, 1993, 8, 2025–2031, Courtneidge et al., *Semin. Cancer Biol.*, 1994, 5, 239–246, Lauffenburger et al., *Cell*, 1996, 84, 359–369, Hanks et al., *BioEssays*, 1996, 19, 137–145, Parsons et al., *Current Opinion in Cell Biology*, 1997, 9, 187–192, Brown et al., *Biochimica et Biophysica Acta*, 1996, 1287, 121–149 and Schlaepfer et al., *Progress in Biophysics and Molecular Biology*, 1999, 71, 435–478). Various classes of non-receptor tyrosine kinases are known including the Src family such as the Src, Lyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase, are frequently significantly activated (when compared to normal cell levels) in common human cancers such as gastrointestinal cancer, for example colon, rectal and stomach cancer (Cartwright et al., *Proc. Natl. Acad. Sci. USA*, 1990, 87, 558–562 and Mao et al., *Oncogene*, 1997, 15, 3083–3090), and breast cancer (Muthuswamy et al., *Oncogene*, 1995, 11, 1801–1810). The Src family of non-receptor tyrosine kinases has also been located in other common human cancers such as non-small cell lung cancers (NSCLCs) including adenocarcinomas and squamous cell cancer of the lung (Mazurenko et al., *European Journal of Cancer*, 1992, 28, 372–7), bladder cancer (Fanning et al., *Cancer Research*, 1992, 52, 1457–62), oesophageal cancer (Jankowski et al., *Gut*, 1992, 33, 1033–8), cancer of the prostate, ovarian cancer (Wiener et al., *Clin. Cancer Research*, 1999, 5, 2164–70) and pancreatic cancer (Lutz et al., *Biochem. and Biophys. Res. Comm.*, 1998, 243, 503–8). As further human tumour tissues are tested for the Src family of non-receptor tyrosine kinases it is expected that its widespread prevalence will be, established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell*, 2000, 11, 51–64 and Klinghoffer et al., *EMBO Journal*, 1999, 18, 2459–2471). Cellular motility is necessarily required for a localised tumour to progress through the stages of dissemination into the blood stream, invasion of other tissues and initiation of metastatic tumour growth. For example, colon tumour progression from localised to disseminated, invasive metastatic disease has been correlated with c-Src non-receptor tyrosine kinase activity (Brunton et al., *Oncogene*, 1997, 14, 283–293, Fincham et al., *EMBO J*, 1998, 17, 81–92 and Verbeek et al., *Exp. Cell Research*, 1999, 248, 531–537).

Accordingly it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular an inhibitor of such non-receptor tyrosine kinases should be of value as an anti-invasive agent for use in the containment and/or treatment of solid tumour disease.

We have now found that surprisingly certain quinoline derivatives possess potent anti-tumour activity. It is believed that the compounds disclosed in the present invention provide an anti-tumour effect by way of inhibition of MEK enzymes that are involved in the MAPK kinase pathway and/or by way of inhibition of one or more of the non-receptor tyrosine-specific protein kinases that are involved in the signal transduction steps which lead to the invasiveness and migratory ability of metastasising tumour cells. In particular, it is believed that the compounds of the present invention provide an anti-tumour effect by inhibition of one or more of the MEK enzymes and/or by way of inhibition of the Src family of non-receptor tyrosine kinases, for example by inhibition of one or more of c-Src, c-Yes and c-Fyn. It is also known that c-Src non-receptor tyrosine kinase enzyme is involved in the control of osteoclast-driven bone resorption (Soriano et al., *Cell*, 1991, 64, 693–702; Boyce et al., *J. Clin. Invest.*, 1992, 90, 1622–1627; Yoneda et al., *J. Clin. Invest.*, 1993, 91, 2791–2795 and Missbach et al., *Bone*, 1999, 24, 437–49). An inhibitor of c-Src non-receptor tyrosine kinase is therefore of value in the prevention and treatment of bone diseases such as osteoporosis, Paget's disease, metastatic disease in bone and tumour-induced hypercalcaemia.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, hypersensitivity reactions of the skin, blood vessel diseases (for example atherosclerosis and restenosis), allergic asthma, insulin-dependent diabetes, diabetic retinopathy and diabetic nephropathy.

The compounds of the invention may possess inhibitory activity against the MEK enzymes that are involved in the MAPK kinase pathway. They may also possess an inhibitory activity against the Src family of non-receptor tyrosine kinases. Generally the compounds of the present invention may also possess potent inhibitory activity against the Src family of non-receptor tyrosine kinases, for example by inhibition of c-Src and/or c-Yes, whilst possessing less potent inhibitory activity against other tyrosine kinase enzymes such as the receptor tyrosine kinases, for example EGF receptor tyrosine kinase and/or VEGF receptor tyrosine kinase.

It is stated in International Patent Application WO 98/43960 that a range of 3-cyanoquinoline derivatives are useful in the treatment of cancer. Certain of the compounds are stated to be inhibitors of the mitogen-activated protein kinase (MAPK) pathway, others are stated to be inhibitors of EGF receptor tyrosine kinase, and others are stated to be inhibitors of growth factors such as vascular endothelial growth factor (VEGF). There is no disclosure therein of any 1,3-benzodioxol-4-yl-containing 3-cyanoquinoline derivatives.

It is stated in International Patent Application WO 00/68201 that a range of 3-cyanoquinoline derivatives are also useful in the treatment of cancer. Certain of the compounds are stated to be inhibitors of MEK, a MAPK kinase. There is no disclosure therein of any 1,3-benzodioxol-4-yl-containing 3-cyanoquinoline derivatives.

It is disclosed in *Journal Medicinal Chemistry*, 2001, 44, 822–833 that certain 4-anilino-3-cyanoquinoline derivatives are useful for the inhibition of Src-dependent cell proliferation. There is no disclosure therein of any 1,3-benzodioxol-4-yl-containing 3-cyanoquinoline derivatives.

According to one aspect of the invention there is provided a quinoline derivative of the Formula I

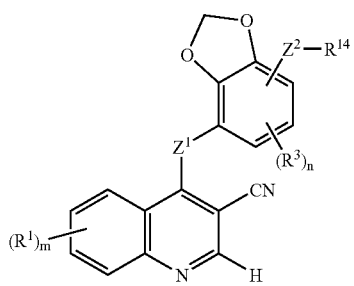

I wherein $Z^1$ is an O, S, SO, $SO_2$, $N(R^2)$ or $C(R^2)_2$ group, wherein each $R^2$ group, which may be the same or different, is hydrogen or (1–6C)alkyl;

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

$Q^1$-$X^1$— 

wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl or, when the inserted group is $N(R^5)$, $R^5$ may also be (2–6C)alkanoyl, and wherein any $CH_2$=CH— or HC≡C— group within a $R^1$ substituent optionally bears at the terminal $CH_2$= or  HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl, di-[(1–6C)alkyl]amino-(1–6C)alkyl or from a group of the formula:

$Q^2$-$X^2$— wherein $X^2$ is a direct bond or is selected from CO and $N(R^6)CO$, wherein $R^6$ is hydrogen or (1–6C)alkyl, and $Q^2$ is aryl, aryl-(1–6C)alkyl, heteroaryl, heteroaryl-(1–6C)alkyl, heterocyclyl or heterocyclyl-(1–6C)alkyl, and wherein any CH, $CH_2$ or $CH_3$ group within a $R^1$ substituent optionally bears on each said CH, $CH_2$ or $CH_3$ group one or more halogeno or (1–6C)alkyl substituents or a substituent selected from hydroxy, cyano, amino, carboxy, carbamoyl, (1–6C)alkoxy, 1–6C)alkylthio, (1–6C)alkylsulphinyl, (1–6C)alkylsulphonyl, (1–6C)alkylamino, N-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^3$-$Q^3$ 

wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^4$—$R^8$ 

wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl or from a group of the formula:

$X^5$-$Q^4$ 

wherein $X^5$ is a direct bond or is selected from O, $N(R^{10})$ and CO, wherein $R^{10}$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^1$ optionally bears 1 or 2 oxo or thioxo substituents;

n is 0, 1, 2 or 3;

each $R^3$ group is halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^6$—$R^{11}$ wherein $X^6$ is a direct bond or is selected from O and N($R^{12}$), wherein $R^{12}$ is hydrogen or (1–6C)alkyl, and $R^{11}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl;

$Z^2$ is a C≡C or C($R^{13}$)=C($R^{13}$) group, wherein each $R^{13}$ group, which may be the same or different, is hydrogen or (1–6C)alkyl; and $R^{14}$ is selected from halogeno, cyano, isocyano, formyl, carboxy, carbamoyl, (2–8C)alkenyl, (2–8C)alkynyl, (1–6C)alkoxycarbonyl, N-(1–6C)alkylcarbamoyl, N,N-di-[(1–6C)alkyl]carbamoyl, (2–6C)alkanoyl, N-(1–6C)alkylsulphamoyl, N,N-di-[(1–6C)alkyl]sulphamoyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl or from a group of the formula:

—$X^7$-$Q^5$ wherein $X^7$ is a direct bond or is selected from CO, CH(O$R^{15}$), CON($R^{15}$) or SO$_2$N($R^{15}$), wherein $R^{15}$ is hydrogen or (1–6C)alkyl, and $Q^5$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein any CH, CH$_2$ or CH$_3$ group within a $R^{14}$ substituent optionally bears on each said CH, CH$_2$ or CH$_3$ group one or more halogeno or (1–6C)alkyl substituents or a substituent selected from hydroxy, cyano, amino, carboxy, carbamoyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^8$-$Q^6$ wherein $X^8$ is a direct bond or is selected from O, S, SO, SO$_2$, N($R^{16}$), CO, CH(O$R^{16}$), CON($R^{16}$), N($R^{16}$)CO, SO$_2$N($R^{16}$), N($R^{16}$)SO$_2$, C($R^{16}$)$_2$O, C($R^{16}$)$_2$S and N($R^{16}$)C($R^{16}$)$_2$, wherein $R^{16}$ is hydrogen or (1–6C)alkyl, and $Q^6$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^{14}$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-1-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^9$—$R^{17}$ wherein $X^9$ is a direct bond or is selected from O and N($R^{18}$), wherein $R^{18}$ is hydrogen or (1–6C)alkyl, and $R^{17}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl, or from a group of the formula:

—$X^{10}$-$Q^7$ wherein $X^{10}$ is a direct bond or is selected from O, N($R^{19}$) and CO, wherein $R^{19}$ is hydrogen or (1–6C)alkyl, and $Q^7$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^{14}$ optionally bears 1 or 2 oxo or thioxo substituents;

or a pharmaceutically-acceptable salt thereof.

In this specification the generic term "alkyl" includes both straight-chain and branched-chain alkyl groups such as propyl, isopropyl and tert-butyl, and also (3–7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1–6C)alkoxy includes methoxy, ethoxy, cyclopropyloxy and cyclopentyloxy, (1–6C)alkylamino includes methylamino, ethylamino, cyclobutylamino and cyclohexylamino, and di-[(1–6C)alkyl]amino includes dimethylamino, diethylamino, N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$ to $Q^7$) when it is aryl or for the aryl group within a 'Q' group is, for example, phenyl or naphthyl, preferably phenyl.

A suitable value for any one of the 'Q' groups ($Q^1$, $Q^3$, $Q^5$ or $Q^6$) when it is (3–7C)cycloalkyl or for the (3–7C)cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^1$, $Q^3$ or $Q^6$) when it is (3–7C)cycloalkenyl or for the (3–7C)cycloalkenyl group within a 'Q' group is, for example, cyclobutenyl, cyclopentenyl, cyclohexenyl or cycloheptenyl.

A suitable value for any one of the 'Q' groups ($Q^1$ to $Q^7$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^7$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, azetidinyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4H-1,4-thiazinyl, piperidinyl or piperazinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1–6C)alkyl is, for example, heteroarylmethyl, 2-heteroarylethyl and 3-heteroarylpropyl. The invention comprises corresponding suitable values for 'Q' groups when, for example, rather than a heteroaryl-(1–6C)alkyl group, an aryl-(1–6C)alkyl, (3–7C)cycloalkyl-(1–6C)alkyl, (3–7C)cycloalkenyl-(1–6C)alkyl or heterocyclyl-(1–6C)alkyl group is present.

A suitable value for a 'Q' group when it is heterocyclyl-(1–6C)alkyl is, for example, 3-piperazin-1-ylpropyl, 3-morpholinopropyl, 3-(1,1-dioxotetrahydro-4H-1,4-thiazinyl) propyl, 3-piperidin-4-ylpropyl, 3-piperidin-1-ylpropyl or 4-pyrrolidin-1ylbutyl.

In structural Formula I there is a hydrogen atom at the 2-position on the quinoline ring. It is to be understood thereby that the $R^1$ substituents may only be located at the 5-, 6-, 7- or 8-positions on the quinoline ring i.e. that the 2-position remains unsubstituted. It is further to be understood that the $R^3$ group that may be present on the 1,3-benzodioxol-4-yl group within structural Formula I may be located on the phenyl ring or on the methylene group within the dioxol group. Preferably, any $R^3$ group that is present on the 1,3-benzodioxol-4-yl group within structural Formula I is located on the phenyl ring thereof. It is further to be understood that the $-Z^2-R^{14}$ group within structural Formula I may only be located on the phenyl ring within the 1,3-benzodioxol-4-yl group.

For the avoidance of doubt, the positions on structural Formula I are numbered as follows:

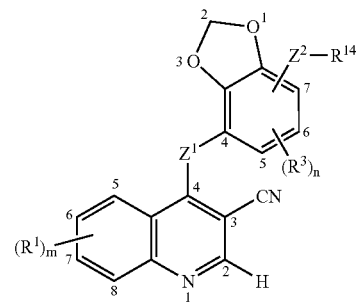

Suitable values for any of the 'R' groups ($R^1$ to $R^{19}$) or for various groups within an $R^1$, $R^3$ or $R^4$ group include:

for halogeno fluoro, chloro, bromo and iodo;

for (1–6C)alkyl: methyl, ethyl, propyl, isopropyl and tert-butyl;

for (2–8C)alkenyl: vinyl, isopropenyl, allyl and but-2-enyl;

for (2–8C)alkynyl: ethynyl, 2-propynyl and but-2-ynyl;

for (1–6C)alkoxy: methoxy, ethoxy, propoxy, isopropoxy and butoxy;

for (2–6C)alkenyloxy: vinyloxy and allyloxy;

for (2–6C)alkynyloxy: ethynyloxy and 2-propynyloxy;

for (1–6C)alkylthio: methylthio, ethylthio and propylthio;

for (1–6C)alkylsulphonyl: methylsulphinyl and ethylsulphinyl;

for (1–6C)alkylsulphonyl: methylsulphonyl and ethylsulphonyl;

for (1–6C)alkylamino: methylamino, ethylamino, propylamino, isopropylamino and butylamino;

for di-[(1–6C)alkyl]amino: dimethylamino, diethylamino, N-ethyl-N-methylamino and diisopropylamino;

for (1–6C)alkoxycarbonyl: methoxycarbonyl, ethoxycarbonyl, propoxycarbonyl and tert-butoxycarbonyl;

for N-(1–6C)alkylcarbamoyl: N-methylcarbamoyl, N-ethylcarbamoyl and N-propylcarbamoyl;

for N,N-di-[(1–6C)alkyl]carbamoyl: N,N-dimethylcarbamoyl, N-ethyl-N-methylcarbamoyl and N,N-diethylcarbamoyl;

for (2–6C)alkanoyl: acetyl and propionyl;

for (2–6C)alkanoyloxy: acetoxy and propionyloxy;

for (2–6C)alkanoylamino: acetamido and propionamido;

for N-(1–6C)alkyl-(2–6C)alkanoylamino: N-methylacetamido and N-methylpropionamido;

for N-(1–6C)alkylsulphamoyl: N-methylsulphamoyl and N-ethylsulphamoyl;

for N,N-di-[(1–6C)alkyl]sulphamoyl: N,N-dimethylsulphamoyl;

for (1–6C)alkanesulphonylamino: methanesulphonylamino and ethanesulphonylamino;

for N-(1–6C)alkyl-(1–6C)alkanesulphonylamino: N-methylmethanesulphonylamino and N-methylethanesulphonylamino;

for (3–6C)alkenoylamino: acrylamido, methacrylamido and crotonamido;

for N-(1–6C)alkyl-(3–6C)alkenoylamino: N-methylacrylamido and N-methylcrotonamido;

for (3–6C)alkynoylamino: propiolamido;

for N-(1–6C)alkyl-(3–6C)alkynoylamino: N-methylpropiolamido;

for amino-(1–6C)alkyl: aminomethyl, 2-aminoethyl, 1-aminoethyl and 3-aminopropyl;

for (1–6C)alkylamino-(1–6C)alkyl: methylaminomethyl, ethylaminomethyl, 1-methylaminoethyl, 2-methylaminoethyl, 2-ethylaminoethyl and 3-methylaminopropyl;

for di-[(1–6C)alkyl]amino-(1–6C)alkyl: dimethylaminomethyl, diethylaminomethyl, 1-dimethylaminoethyl, 2-dimethylaminoethyl and 3-dimethylaminopropyl;

for halogeno-(1–6C)alkyl: chloromethyl, 2-chloroethyl, 1-chloroethyl and 3-chloropropyl;

for hydroxy-(1–6C)alkyl: hydroxymethyl, 2-hydroxyethyl, 1-hydroxyethyl and 3-hydroxypropyl;

for (1–6C)alkoxy-(1–6C)alkyl: methoxymethyl, ethoxymethyl, 1-methoxyethyl, 2-methoxyethyl, 2-ethoxyethyl and 3-methoxypropyl;

for cyano-(1–6C)alkyl: cyanomethyl, 2-cyanoethyl, 1-cyanoethyl and 3-cyanopropyl;

for (2–6C)alkanoylamino-(1–6C)alkyl: acetamidomethyl, propionamidomethyl and 2-acetamidoethyl; and for (1–6C)alkoxycarbonylamino-(1–6C)alkyl: methoxycarbonylaminomethyl, ethoxycarbonylaminomethyl, tert-butoxycarbonylaminomethyl and 2-methoxycarbonylaminoethyl.

A suitable value for $(R^1)_m$ when it is a (1–3C)alkylenedioxy group is, for example, methylenedioxy or ethylenedioxy and the oxygen atoms thereof occupy adjacent ring positions.

When, as defined hereinbefore, an $R^1$ group forms a group of the formula $Q^1$-$X^1$— and, for example, $X^1$ is a $OC(R^4)_2$ linking group, it is the carbon atom, not the oxygen atom, of the $OC(R^4)_2$ linking group which is attached to the quinoline ring and the oxygen atom is attached to the $Q^1$ group. Similarly, when, for example a $CH_3$ group within a $R^1$ substituent bears a group of the formula —$X^3$-$Q^3$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^3$ group. A similar convention applies to the attachment of the groups of the formulae $Q^3$-$X^3$—, and —$X^8$-$Q^6$.

As defined hereinbefore, adjacent carbon atoms in any (2–6C)alkylene chain within a $R^1$ substituent may be optionally separated by the insertion into the chain of a group such as O, CON($R^5$) or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any CH, $CH_2$ or $CH_3$ group within a $R^1$ or $R^{14}$ substituent optionally bears on each said CH, $CH_2$ or $CH_3$ group a substituent as defined hereinbefore, suitable $R^1$ or $R^{14}$ substituents so formed include, for example, hydroxy-substituted heterocyclyl-(1–6C) alkoxy groups such as 2-hydroxy-3-piperidinopropoxy and 2-hydroxy-3-morpholinopropoxy.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinoline derivatives of the Formula I, or pharmaceutically-acceptable salts thereof, wherein, unless otherwise stated, each of $Z^1$, m, $R^1$, n, $R^3$, $Z^2$ and $R^{14}$ has any of the meanings defined hereinbefore or in paragraphs (a) to (y) hereinafter:—

(a) $Z^1$ is O, S, SO, $SO_2$, $CH_2$ or NH;

(b) $Z^1$ is O;

(c) $Z^1$ is NH;

(d) $R^1$ substituents may only be located at the 5-, 6- and/or 7-positions on the quinoline ring i.e. the 2- and 8-positions remain unsubstituted;

(e) $R^1$ substituents may only be located at the 6- and/or 7-positions on the quinoline ring i.e. the 2-, 5- and 8-positions remain unsubstituted;

(f) $R^1$ substituents may only be located at the 5- and/or 7-positions on the quinoline ring i.e. the 2-, 6- and 8-positions remain unsubstituted;

(g) m is 1 or 2, and each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (2–6C)alkenyloxy, (2–6C)alkyloxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino or from a group of the formula:

$Q^1$-$X^1$— wherein $X^1$ is a direct bond or is selected from O, N($R^4$), CON($R^4$), N($R^4$)CO and OC($R^4$)$_2$ wherein $R^4$ is hydrogen or (1–6C)alkyl, and $Q^1$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, N($R^5$), CON($R^5$), N($R^5$)CO, CH—CH and C≡C wherein $R^5$ is hydrogen or (1–6C)alkyl, or, when the inserted group is N($R^5$), $R^5$ may also be (2–6C)alkanoyl, and wherein any $CH_2$=CH— or HC≡C— group within a $R^1$ substituent optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^2$-$X^2$— wherein X² is a direct bond or is CO or N(R⁶)CO, wherein R⁶ is hydrogen or (1–6C)alkyl, and Q² is heteroaryl, heteroaryl-(1–6C)alkyl, heterocyclyl or heterocyclyl-(1–6C)alkyl, and wherein any CH₂ or CH₃ group within a R¹ substituent optionally bears on each said CH₂ or CH₃ group one or more halogeno groups or a substituent selected from hydroxy, amino, (1–6C)alkoxy, (1–6C)alkylsulphonyl, (1–6C)alkylamino, di-[(1–6C)alkyl]amino, (2–6C)alkanoyloxy, (2–6C)alkanoylamino, N-(1–6C)alkyl-(2–6C)alkanoylamino or from a group of the formula:

—X³-Q³ wherein X³ is a direct bond or is selected from O, N(R⁶), CON(R⁷), N(R⁷)CO and C(R⁷)₂O, wherein R⁷ is hydrogen or (1–6C)alkyl, and Q³ is heteroaryl, heteroaryl-(1–6C)alkyl, heterocyclyl or heterocyclyl-(1–6C)alkyl, and wherein any aryl, heteroaryl or heterocyclyl group within a substituent on R¹ optionally bears 1, 2 or 3 substituents, which may be the same or different, selected from halogeno, trifluoromethyl, hydroxy, amino, carbamoyl, (1–6C)alkyl, (2–8C)alkenyl, (2–8C)alkyl, (1–6C)alkoxy, (1–6C)alkylsulphonyl, N-(1–6C)alkylcarbamoyl, N,N-di-[(1–6C)alkyl]carbamoyl and (2–6C)alkanoyl, or optionally bears 1 substituent selected from a group of the formula:

—X⁴—R⁸ wherein X⁴ is a direct bond or is selected from O and N(R⁹), wherein R⁹ is hydrogen or (1–6C)alkyl, and R⁸ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl or from a group of the formula:

—X⁵-Q⁴ wherein X⁵ is a direct bond or is selected from O, N(R¹⁰) and CO, wherein R¹⁰ is hydrogen or (1–6C)alkyl, and Q⁴ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on R¹ optionally bears 1 or 2 oxo substituents;

(h) m is 1 or 2, and each R¹ group, which may be the same or different, is selected from fluoro, chloro, trifluoromethyl, hydroxy, amino, carbamoyl, methyl, ethyl, propyl, butyl, vinyl, allyl, but-3-enyl, pent-4-enyl, hex-5-enyl, ethynyl, 2-propynyl, but-3-ynyl, pent-4-ynyl, hex-5-ynyl, methoxy, ethoxy, propoxy; isopropoxy, butoxy, allyloxy, but-3-enyloxy, pent-4-enyloxy, hex-5-enyloxy, ethynyloxy, 2-propynyloxy, but-3-ynyloxy, pent-4-ynyloxy, hex-5-ynyloxy, methylamino, ethylamino, propylamino, dimethylamino, diethylamino, dipropylamino, N-methylcarbamoyl, N,N-dimethylcarbamoyl, acetamido, propionamido, acrylamido and propiolamido or from a group of the formula:

Q¹-X¹— wherein X¹ is a direct bond or is selected from O, NH, CONH, NHCO and OCH₂ and Q¹ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl) ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2–6C)alkylene chain within a R¹ substituent are optionally separated by the insertion into the chain of a group selected from O, NH, N(Me), CONH, NHCO, CH=CH and C≡C, and wherein any CH₂=CH— or HC≡C— group within a R¹ substituent optionally bears at the terminal CH₂= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl 3-dimethylaminopropyl or 4-dimethylaminobutyl, or from a group of the formula:

Q²-X² wherein X² is a direct bond or is CO, NHCO or N(Me)CO and Q² is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH₂ or CH₃ group within a R¹ substituent optionally bears on each said CH₂ or CH₃ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido or from a group of the formula:

—X³-Q³ wherein X³ is a direct bond or is selected from O, NH, CONH, NHCO and CH₂O and Q³ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl or optionally bears 1 substituent selected from a group of the formula:

—$X^4$—$R^8$ wherein $X^4$ is a direct bond or is selected from O and NH and $R^8$ is 2-fluoroethyl, 3-fluoropropyl, 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl, tert-butoxycarbonylaminomethyl or a group of the formula:

—$X^5$-$Q^4$ wherein $X^5$ is a direct bond or is selected from O, NH and CO and $Q^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(i) m is 1 or 2, and each $R^1$ group, which may be the same or different, is selected from halogeno, trifluoromethyl, hydroxy, amino, carbamoyl, (1–6C)alkyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino or from a group of the formula:

$Q^1$-$X^1$— wherein $X^1$ is selected from O, —N($R^4$), CON($R^4$), N($R^4$)CO and OC($R^4$)$_2$ wherein $R^4$ is hydrogen or (1–6C)alkyl, and $Q^1$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, or $X^1$ is a direct bond and $Q^1$ is aryl-(1–6C)alkyl, cycloalkyl-(1–6C)alkyl, heteroaryl-(1–6C)alkyl or heterocyclyl-(1–6C)alkyl, and wherein adjacent carbon atoms in any (2–6C)alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1–6C)alkyl, or, when the inserted group is N($R^5$), $R^5$ may also be (2–6C)alkanoyl, and wherein any CH$_2$ or CH$_3$ group within a $R^1$ substituent optionally bears on each said CH$_2$ or CH$_3$ group one or more halogeno groups or a substituent-selected from hydroxy, amino, (1–6C)alkoxy, (1–6C)alkylsulphonyl, (1–6C)alkylamino, di [(1–6C)alkyl]amino, (2–6C)alkanoy loxy, (2–6C)alkanoylamino, N-(1–6C)alkyl-(2–6C)alkanoylamino or a group of the formula:

—$X^3$-$Q^3$ wherein $X^3$ is a direct bond or is selected from O, N($R^6$), CON($R^7$), N($R^7$)CO and C($R^7$)$_2$O, wherein $R^7$ is hydrogen or (1–6C)alkyl, and $Q^3$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (2–8C)alkenyl, (2–8C)alkynyl, (1–6C)alkoxy, (1–6C)alkylsulphonyl, N-(1–6C)alkylcarbamoyl, N,N-di-[(1–6C)alkyl]carbamoyl and (2–6C)alkanoyl, or optionally bears 1 substituent selected from a group of the formula:

—$X^4$—$R^8$ wherein $X^4$ is a direct bond or is selected from O and N($R^9$), wherein $R^9$ is hydrogen or (1–6C)alkyl, and $R^8$ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl or from a group of the formula:

—$X^5$-$Q^4$ wherein $X^5$ is a direct bond or is selected from O, N($R^{10}$) and CO, wherein $R^{10}$ is hydrogen or (1–6C)alkyl, and $Q^4$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo substituents;

(j) m is 1 or 2, and each $R^1$ group, which may be the same or different, is selected from fluoro, chloro, trifluoromethyl, hydroxy, amino, carbamoyl, methyl, ethyl, propyl, butyl, methoxy, ethoxy, propoxy, isopropoxy, butoxy, methylamino, ethylamino, propylamino, dimethylamino, diethylamino, dipropylamino, N-methylcarbamoyl, N,N-dimethylcarbamoyl, acetamido, propionamido, acrylamido, propiolamido or from a group of the formula:

$Q^1$-$X^1$— wherein $X^1$ is selected from O, NH, CONH, NHCO and OCH$_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinomethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, or wherein $X^1$ is a direct bond and $Q^1$ is benzyl, cyclopropylmethyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, is N(Me), CONH, NHCO, CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido, N-methylacetamido or from a group of the formula:

—$X^3$-$Q^3$ wherein $X^3$ is a direct bond or is selected from O, NH, CONH, NHCO and $CH_2O$ and $Q^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—$X^4$—$R^8$ wherein $X^4$ is a direct bond or is selected from O and NH and $R^8$ is 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl, tert-butoxycarbonylaminomethyl or from a group of the formula:

—$X^5$-$Q^4$ wherein $X^5$ is a direct bond or is selected from O, NH and CO and $Q^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(k) m is 2 and each $R^1$ group, which may be the same or different, is located at the 5- and 7-positions or at the 6- and 7-positions and $R^1$ is selected from hydroxy, amino, methyl, ethyl, propyl, methoxy, ethoxy, propoxy, isopropoxy, butoxy, pentyloxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1, 1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein adjacent carbon atoms in any (2–6C)alkylene chain within a $R^1$ substituent are optionally separated by the insertion into the chain of a group selected from O, NH, N(Me), CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, and wherein any phenyl, imidazolyl, triazolyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, N-methylcarbamoyl, N,N-dimethylcarbamoyl and methoxy, and a pyrrolidin-2-yl, piperidin-3-yl, piperidin-4-yl, piperazin-1-yl or homopiperazin-1-yl group within a $R^1$ substituent is optionally N-substituted with allyl, 2-propynyl, methylsulphonyl, acetyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(l) n is 0;

(m) n is 1 or 2 and the $R^3$ groups, which may be the same or different, are located at the 5- and/or 6-positions of the 1,3-benzodioxol-4-yl group and are selected from halogeno, trifluoromethyl cyano, hydroxy, (1–6C)alkyl, (2–8C)alkenyl, (2–8C)alkynyl, (1–6C)alkoxy, (1–6C)alkylthio, (1–6C)alkylsulphinyl, (1–6C)alkylsulphonyl or from a group of the formula:

wherein $X^6$ is a direct bond and $R^{11}$ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl;

(n) n is 1 or 2 and the $R^3$ groups, which may be the same or different, are located at the 5- and/or 6-positions of the 1,3-benzodioxol-4-yl group and are selected from halogeno, trifluoromethyl, cyano, hydroxy, (1–6C)alkyl, (2–8C)alkenyl, (2–8C)alkynyl and (1–6C)alkoxy;

(o) n is 1 or 2 and the $R^3$ groups, which may be the same or different, are located at the 5- and/or 6-positions of the 1,3-benzodioxol-4-yl group and are selected from fluoro, chloro, bromo, iodo, trifluoromethyl, cyano, hydroxy, methyl, ethyl, vinyl, allyl, isopropenyl, ethynyl, 1-propynyl, 2-propynyl, methoxy and ethoxy;

(p) n is 1 and the $R^3$ group is located at the 5- or 6-position of the 1,3-benzodioxol-4-yl group, especially the 5-position, and is selected from chloro, bromo, trifluoromethyl, cyano, hydroxy, methyl, ethyl, methoxy and ethoxy;

(q) n is 1 and the $R^3$ group is located at the 5- or 6-position of the 1,3-benzodioxol-4-yl group, especially the 5-position, and is selected from fluoro, chloro, bromo, trifluoromethyl, cyano, hydroxy, methyl, ethyl, methoxy and ethoxy;

(r) the $-Z^2-R^{14}$ group is located at the 7- or 6-position on the 1,3-benzodioxol-4-yl group;

(s) the $-Z^2-R^{14}$ group is located at the 7-position on the 1,3-benzodioxol-4-yl group;

(t) $Z^2$ is a C≡C group;

(u) $Z^2$ is a CH=CH group;

(v) $R^{14}$ is selected from halogeno, cyano, formyl, carboxy, carbamoyl, (2–8C)alkenyl, (1–6C)alkoxycarbonyl, N-(1–6C)alkylcarbamoyl, N,N-di-[(1–6C)alkyl]carbamoyl, (2–6C)alkanoyl, N-(1–6C)alkylsulphamoyl, N,N-di-[(1–6C)alkyl]sulphamoyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or from a group of the formula:

wherein $X^7$ is a direct bond or CO and $Q^5$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^{14}$ substituent optionally bears on each said $CH_2$ or $CH_3$ group one or more halogeno or (1–6C)alkyl substituents or a substituent selected from hydroxy, cyano, amino, (1–6C)alkoxy, (1–6C)alkylthio, (1–6C)alkylsulphinyl, (1–6C)alkylsulphonyl, (1–6C)alkylamino, di-[(1–6C)alkyl]amino, (2–6C)alkanoyl, (2–6C)alkanoyloxy, (2–6C)alkanoylamino, N-(1–6C)alkyl-(2–6C)alkanoylamino or from a group of the formula:

wherein $X^8$ is a direct bond or is selected from O, $N(R^{16})$, $CON(R^{16})$, $N(R^{16})CO$ and $C(R^{16})_2O$, wherein $R^{16}$ is hydrogen or (1–6C)alkyl, and $Q^6$ is heteroaryl, heteroaryl-(1–6C)alkyl, heterocyclyl or heterocyclyl-(1–6C)alkyl, and wherein any aryl, heteroaryl or heterocyclyl group within a substituent on $R^{15}$ optionally bears 1, 2 or 3 substituents, which may be the same or different, selected from halogeno, trifluoromethyl, hydroxy, amino, carbamoyl, (1–6C)alkyl, (2–8C)alkenyl, (2–8C)alkynyl, (1–6C)alkoxy, (1–6C)alkylsulphonyl, N-(1–6C)alkylcarbamoyl, N,N-di-[(1–6C)alkyl]carbamoyl and (2–6C)alkanoyl, or optionally bears 1 substituent selected from a group of the formula:

wherein $X^9$ is a direct bond or is selected from O and $N(R^{18})$, wherein $R^{18}$ is hydrogen or (1–6C)alkyl, and $R^{17}$ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl, and from a group of the formula:

wherein $X^{10}$ is a direct bond or is selected from O, $N(R^{19})$ and CO, wherein $R^{19}$ is hydrogen or (1–6C)alkyl, and $Q^7$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^{14}$ optionally bears 1 or 2 oxo substituents;

(w) $R^{14}$ is selected from chloro, cyano, formyl, carboxy, carbamoyl, methoxycarbonyl, vinyl, ethoxycarbonyl, N-methylcarbamoyl, N-ethylcarbamoyl, N N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, cyanomethyl, 2-cyanoethyl, 3-cyanopropyl, aminomethyl, 2-aminoethyl, 3-aminopropyl, methylaminomethyl ethylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, 2-acetamidoethyl, 3-acetamidopropyl or from a group of the formula:

—X$^7$-Q$^5$ wherein-X$^7$ is a direct bond or CO and Q$^5$ is phenyl, benzyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 1,1-dioxotetrahydro-4H-1,4-thiazin-4-ylmethyl, piperazin-1-ylmethyl, homopiperazin-1-ylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein any CH$_2$ or CH$_3$ group within a R$^{14}$ substituent optionally bears on each said CH$_2$ or CH$_3$ group one or more fluoro, chloro or methyl groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, or from a group of the formula:

—X$^8$-Q$^6$ wherein X$^8$ is a direct bond or is selected from O, NH, CONH, NHCO and CH$_2$O and Q$^6$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on R$^{14}$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—X$^9$—R$^{17}$ wherein X$^9$ is a direct bond or is selected from O and NH and R$^{17}$ is 2-fluoroethyl, 3-fluoropropyl, 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl, tert-butoxycarbonylaminomethyl and from a group of the formula:

—X$^{10}$-Q$^7$ wherein X$^{10}$ is a direct bond or is selected from O, NH and CO and Q$^7$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on R$^{14}$ optionally bears 1 or 2 oxo substituents; and (x) R$^{14}$ is selected from chloro, cyano, formyl, carboxy, carbamoyl, vinyl, methoxycarbonyl, ethoxycarbonyl, N-methylcarbamoyl, N-ethylcarbamoyl, N N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, cyanomethyl, 2-cyanoethyl, 3-cyanopropyl, aminomethyl, 2-aminoethyl, 3-aminopropyl, methylaminomethyl, ethylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, 2-acetamidoethyl, 3-acetamidopropyl or from a group of the formula:

—X$^7$-Q$^5$ wherein X$^7$ is a direct bond or CO and Q$^5$ is phenyl, benzyl, 1-, 2- or 3-pyrrolidinyl, morpholino, 1,1-dioxotetrahydro-4H-1,4-thiazin-4-yl, pyridin-2-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 1,1-dioxotetrahydro-4H-1,4-thiazin-4-ylmethyl, piperazin-1-ylmethyl, homopiperazin-1-ylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4' thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein any CH$_2$ or CH$_3$ group within a R$^{14}$ substituent optionally bears on each said CH$_2$ or CH$_3$ group one or more fluoro, chloro or methyl groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, or from a group of the formula:

—X$^8$-Q$^6$ wherein X$^8$ is a direct bond or is selected from O, NH, CONH, NHCO and CH$_2$O and Q$^6$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on R$^{14}$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—$X^9$—$R^{17}$ wherein $X^9$ is a direct bond or is selected from O and NH and $R^{17}$ is 2-fluoroethyl, 3-fluoropropyl, 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl, tert-butoxycarbonylaminomethyl and from a group of the formula:

—$X^{10}$-$Q^7$ wherein $X^{10}$ is a direct bond or is selected from O, NH and CO and $Q^7$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^{14}$ optionally bears 1 or 2 oxo substituents; and (y) $R^{14}$ is selected from cyano, formyl, carboxy, carbamoyl, vinyl, methoxycarbonyl, ethoxycarbonyl, N-methylcarbamoyl, N-ethylcarbamoyl, N,N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl or from a group of the formula:

—$X^7$-$Q^5$ wherein $X^7$ is a direct bond or CO and $Q^5$ is pyridin-2-yl, 1-pyrrolidinyl, morpholino, 1,1-dioxotetrahydro-4H-1,4-thiazin-4-yl, piperidino, 1-homopiperidinyl, piperazin-1-yl, homopiperazin-1-yl,1-pyrrolidinylmethyl, morpholinomethyl, piperidinomethyl, 1-homopiperidinylmethyl, 1,1-dioxotetrahydro-4H-1,4-thiazin-4-ylmethyl, piperazin-1-ylmethyl, homopiperazin-1-ylmethyl or 3-morpholinopropyl, and wherein any $CH_2$ or $CH_3$ group within a $R^{14}$ substituent optionally bears on each said $CH_2$ or $CH_3$ group one or more fluoro, chloro or methyl groups or a substituent selected from hydroxy, amino, methoxy, methylamino, dimethylamino, acetoxy, acetamido and N-methylacetamido, and wherein any heteroaryl or heterocyclyl group within a substituent on $R^{14}$ optionally bears 1, 2 or 3 substituents, which may be the same or different, selected from hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—$X^9$—$R^{17}$ wherein $X^9$ is a direct bond and $R^{17}$ is 2-fluoroethyl, 2-hydroxyethyl, 3-hydroxypropyl, 2-methoxyethyl, 3-methoxypropyl, cyanomethyl, aminomethyl, methylaminomethyl, dimethylaminomethyl, acetamidomethyl, methoxycarbonylaminomethyl, ethoxycarbonylaminomethyl or tert-butoxycarbonylaminomethyl, and wherein any heterocyclyl group within a substituent on $R^{14}$ optionally bears 1 or 2 oxo substituents.

A particular compound of the invention is a quinoline derivative of the Formula I wherein:

$Z^1$ is O or NH;

m is 1 and the $R^1$ group is located at the 5-, 6- or 7-position or m is 2 and each $R^1$ group, which may be the same or different, is located at the 5- and 7-positions or at the 6- and 7-positions and $R^1$ is selected from hydroxy, amino, methyl, ethyl, propyl, butyl, methoxy, ethoxy, propoxy, isopropoxy, butoxy, pent-4-ynyloxy, hex-5-ynyloxy, methylamino, ethylamino, dimethylamino, diethylamino, acetamido, propionamido, 2-imidazol-1-ylethoxy, 2-(1,2,4-triazol-1-yl)ethoxy, tetrahydrofuran-3-yloxy, tetrahydropyran-4-yloxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, N(Me), CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy;

and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a $R^1$ substituent is optionally N-substituted with allyl, methylsulphonyl, acetyl, 2-fluoroethyl, 3-fluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

n is 0 or 1 and the $R^3$ group, if present, is located at the 5- or 6-position of the 1,3-benzodioxol-4-yl group and is selected from fluoro, chloro, bromo, trifluoromethyl, cyano, hydroxy, methyl, ethyl, vinyl, allyl, ethynyl, methoxy and ethoxy;

$Z^2$ is a C≡C or CH═CH group; and $R^{14}$ is selected from cyano, formyl, carboxy, carbamoyl, methoxycarbonyl, ethoxycarbonyl, N-methylcarbamoyl, N-ethylcarbamoyl, N,N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, cyanomethyl, 2-cyanoethyl, 3-cyanopropyl, methylaminomethyl, ethylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, 2-acetamidoethyl and 3-acetamidopropyl, or from a group of the formula:

—$X^7$-$Q^5$ wherein $X^7$ is a direct bond or CO and $Q^5$ is 1-pyrrolidinyl, morpholino, 1,1-dioxotetrahydro-4H-1,4-thiazinyl, piperidino, 1-homopiperidinyl, piperazin-1-yl, homopiperazin-1-yl, 1-pyrrolidinylmethyl, morpholinomethyl, piperidinomethyl, 1-homopiperidinylmethyl, 1,1-dioxotetrahydro-4H-1,4-thiazin-4-ylmethyl, piperazin-1-ylmethyl, homopiperazin-1-ylmethyl or 3-morpholinopropyl, and wherein any $CH_2$ or $CH_3$ group within a $R^{14}$ substituent optionally bears on each said $CH_2$ or $CH_3$ group one or more fluoro, chloro or methyl groups or a substituent selected from hydroxy, amino, methoxy, methylamino, dimethylamino, acetoxy, acetamido and N-methylacetamido, and wherein any heterocyclyl group within a substituent on $R^{14}$ optionally bears 1, 2 or 3 substituents, which may be the same or different, selected from hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—$X^9$—$R^{17}$ wherein $X^9$ is a direct bond and $R^{17}$ is 2-hydroxyethyl, 3-hydroxypropyl, 2-methoxyethyl, 3-methoxypropyl, cyanomethyl, aminomethyl, methylaminomethyl, dimethylaminomethyl, acetamidomethyl, methoxycarbonylaminomethyl, ethoxycarbonylaminomethyl or tert-butoxycarbonylaminomethyl, and wherein any heterocyclyl group within a substituent on $R^{14}$ optionally bears 1 or 2 oxo substituents;

or a pharmaceutically-acceptable acid-addition salt thereof.

A particular compound of the invention is a quinoline derivative of the Formula I wherein:

$Z^1$ is O or NH, m is 1 and the $R^1$ group is located at the 5-, 6- or 7-position or m is 2 and each $R^1$ group, which may be the same or different, is located at the 5- and 7-positions or at the 6- and 7-positions and $R^1$ is selected from hydroxy, amino, methyl, ethyl, propyl, butyl, methoxy, ethoxy, propoxy, isopropoxy, butoxy, pent-4-ynyloxy, hex-5-ynyloxy, methylamino, ethylamino, dimethylamino, diethylamino, acetamido, propionamido, 2-imidazol-1-ylethoxy, 2-(1,2,4-triazol-1-yl)ethoxy, tetrahydrofuran-3-yloxy, tetrahydropyran-4-yloxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, N(Me), CH═CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy, and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a $R^1$ substituent is optionally N-substituted with allyl, methylsulphonyl, acetyl, 2-fluoroethyl, 3-fluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

n is 0 or 1 and the $R^3$ group, if present, is located at the 5- or 6-position of the 1,3-benzodioxol-4-yl group and is selected from fluoro, chloro, bromo, trifluoromethyl, cyano, hydroxy, methyl, ethyl, vinyl, allyl, ethynyl, methoxy and ethoxy;

$Z^2$ is a C≡C or CH═CH group; and $R^{14}$ is selected from cyano, formyl, carboxy, carbamoyl, vinyl, methoxycarbonyl, ethoxycarbonyl, N-methylcarbamoyl, N-ethylcarbamoyl, N N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, cyanomethyl, 2-cyanoethyl, 3-cyanopropyl, methylaminomethyl, ethylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, 2-acetamidoethyl and 3-acetamidopropyl, or from a group of the formula:

—$X^7$-$Q^5$ wherein $X^7$ is a direct bond or CO and $Q^5$ is pyridin-2-yl, 1-pyrrolidinyl, morpholino, 1,1-dioxotetrahydro-4H-1,4-thiazin-4-yl, piperidino, 1-homopiperidinyl, piperazin-1-yl, homopiperazin-1-yl, 1-pyrrolidinylmethyl, morpholinomethyl, piperidinomethyl, 1-homopiperidinylmethyl, 1,1-dioxotetrahydro-4H-1,4-thiazin-4-ylmethyl, piperazin-1-ylmethyl, homopiperazin-1-ylmethyl or 3-morpholinopropyl;

and wherein any $CH_2$ or $CH_3$ group within a $R^{14}$ substituent optionally bears on each said $CH_2$ or $CH_3$ group one or more fluoro, chloro or methyl groups or a substituent selected from hydroxy, amino, methoxy, methylamino, dimethylamino, acetoxy, acetamido and N-methylacetamido, and wherein any heteroaryl or heterocyclyl group within a substituent on $R^{14}$ optionally bears 1, 2 or 3 substituents, which may be the same or different, selected from hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—$X^9$—$R^{17}$ wherein $X^9$ is a direct bond and $R^{17}$ is 2-hydroxyethyl, 3-hydroxypropyl, 2-methoxyethyl, 3-methoxypropyl, cyanomethyl, aminomethyl, methylaminomethyl, dimethylaminomethyl, acetamidomethyl, methoxycarbonylaminomethyl, ethoxycarbonylaminomethyl or tert-butoxycarbonylaminomethyl, and wherein any heterocyclyl group within a substituent on $R^{14}$ optionally bears 1 or 2 oxo substituents;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy and 2-[2-(4-methylpiperazin-1-yl)ethoxy]ethoxy and 2-fluoro-3-(4-hydroxypiperidin-1-yl)propoxy;

n is 0 or n is 1 and the $R^3$ group, if present, is located at the 5-position of the 1,3-benzodioxol-4-yl group and is selected from fluoro, chloro and bromo;

the -$Z^2$-$R^{14}$ group is located at the 7-position on the 1,3-benzodioxol-4-yl group, $Z^2$ is a C≡C or CH=CH group; and $R^{14}$ is selected from cyano, formyl, carboxy, carbamoyl, methoxycarbonyl, vinyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, pyridin-2-yl, 1-pyrrolidinylcarbonyl, morpholinocarbonyl, 1,1-dioxotetrahydro-4H-1,4-thiazin-4-ylcarbonyl, piperidinocarbonyl, piperazin-1-ylcarbonyl, 1-pyrrolidinylmethyl, morpholinomethyl, piperidinomethyl, 1,1-dioxotetrahydro-4H-1,4-thiazin-4-ylmethyl, piperazin-1-ylmethyl and 3-morpholinopropyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy and 2-[2-(4-methylpiperazin-1-yl)ethoxy]ethoxy;

n is 0 or n is 1 and the $R^3$ group, if present, is located at the 5-position of the 1,3-benzodioxol-4-yl group and is selected from chloro and bromo;

the -$Z^2$-$R^{14}$ group is located at the 7-position on the 1,3-benzodioxol-4-yl group, $Z^2$ is a C≡C or CH=CH group; and $R^{14}$ is selected from cyano, formyl, carboxy, carbamoyl, methoxycarbonyl, ethoxycarbonyl, N-methylcarbamoyl, N-ethylcarbamoyl, N-(2-methoxyethyl)carbamoyl, N,N-methylcarbamoyl, N-ethyl-N-methylcarbamoyl, N-(2-methoxyethyl)-N-methylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, 1-pyrrolidinylcarbonyl, morpholinocarbonyl, 1,1-dioxotetrahydro-4H-1,4-thiazin-4-ylcarbonyl, piperidinocarbonyl, piperazin-1-ylcarbonyl, 1-pyrrolidinylmethyl, morpholinomethyl, piperidinomethyl, 1,1-dioxotetrahydro-4H-1,4-thiazin-4-ylmethyl, piperazin-1-ylmethyl and 3-morpholinopropyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy, 2-[2-(4-methylpiperazin-1-yl)ethoxy]ethoxy and 2-fluoro-3-(4-hydroxypiperidin-1-yl-propoxy;

n is 0 or n is 1 and the $R^3$ group, if present, is located at the 5-position of the 1,3-benziodioxol-4-yl group and is selected from fluoro, chloro and bromo;

the $-Z^2-R^{14}$ group is located at the 7-position on the 1,3-benzodioxol-4-yl group, Z is a C≡C group; and $R^{14}$ is selected from chloromethyl, 2-chloroethyl, 3-chloropropyl, hydroxymethyl, vinyl 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, pyridin-2-yl, 1-pyrrolidinylmethyl, morpholinomethyl, piperidinomethyl, 1,1-dioxotetrahydro-4H-1,4-thiazin-4-ylmethyl, piperazin-1-ylmethyl and 3-morpholinopropyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy and 2-[2-(4-methylpiperazin-1-yl)ethoxy]ethoxy;

n is 0 or n is 1 and the $R^3$ group, if present, is located at the 5-position of the 1,3-benzodioxol-4-yl group and is selected from chloro and bromo;

the $-Z^2-R^{14}$ group is located at the 7-position on the 1,3-benzodioxol-4-yl group, $Z^2$ is a CH=CH group; and $R^{14}$ is selected from cyano, formyl, carboxy, carbamoyl, methoxycarbonyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, 1-pyrrolidinylcarbonyl, morpholinocarbonyl, 1,1-dioxotetrahydro-4H-1,4-thiazin-4-ylcarbonyl, piperidinocarbonyl, piperazin-1-ylcarbonyl, 1-pyrrolidinyl-methyl, morpholinomethyl, piperidinomethyl, 1,1-dioxotetrahydro-4H-1,4-thiazin-4-ylmethyl and piperazin-1-ylmethyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy and 2-fluoro-3-(4-hydroxypiperidin-1-yl)propoxy;

n is 0 or n is 1 and $R^3$ is a fluoro or chloro group located at the 5-position of the 1,3-benzodioxol-4-yl group;

the $-Z^2-R^{14}$ group is located at the 7-position on the 1,3-benzodioxol-4-yl group, $Z^2$ is a C≡C group; and $R^{14}$ is selected from vinyl, hydroxymethyl, methoxymethyl, dimethylaminomethyl, pyridin-2-yl, 1-pyrrolidinylmethyl, morpholinomethyl, piperidinomethyl, 1,1-dioxotetrahydro-4H-1,4-thiazin-4-ylmethyl and piperazin-1-ylmethyl;

or a pharmaceutically-acceptable acid-addition salt thereof.

A further particular compound of the invention is a quinoline derivative of the Formula I wherein:

$Z^1$ is NH m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy and 2-(2-pyrrolidin-1-ylethoxy)ethoxy;

n is 0 or n is 1 and $R^3$ is a chloro group located at the 5-position of the 1,3-benziodioxol-4-yl group;

the $-Z^2-R^{14}$ group is located at the 7-position on the 1,3-benzodioxol-4-yl group, $Z^2$ is a C≡C group; and $R^{14}$ is selected from hydroxymethyl, methoxymethyl, dimethylaminomethyl, 1-pyrrolidinylmethyl, morpholinomethyl, piperidinomethyl, 1,1-dioxotetrahydro-4H-1,4-thiazin-4-ylmethyl and piperazin-1-ylmethyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy and 2-(2-pyrrolidin-1-ylethoxy)ethoxy;

n is 0 or n is 1 and $R^3$ is a chloro group located at the 5-position of the 1,3-benziodioxol-4-yl group;

the $-Z^2-R^4$ group is located at the 7-position on the 1,3-benzodioxol-4-yl group, $Z^2$ is a CH=CH group; and $R^{14}$ is selected from cyano, carboxy, carbamoyl, methoxycarbonyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, 1-pyrrolidinylcarbonyl, morpholinocarbonyl, 1,1-dioxotetrahydro-4H-1,4-thiazin-4-ylcarbonyl, piperidinocarbonyl and piperazin-1-ylcarbonyl;

or a pharmaceutically-acceptable acid-addition salt thereof.

A further particular compound of the invention is a quinoline derivative of the Formula I wherein:

$Z^1$ is NH;

m is 2 and the first $R^1$ group is located at the 5-position and is selected from N-methylpiperidin-4-yloxy and tetrahydro-2H-pyran-4-yloxy and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(E-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy, 2-[2-(4-methylpiperazin-1-yl)ethoxy]ethoxy and 2-fluoro-3-(4-hydroxypiperidin-1-yl)propoxy;

n is 0 or n is 1 and $R^3$ is located at the 5-position of the 1,3-benzodioxol-4-yl group and is selected from a fluoro, chloro or bromo group;

the $-Z^2-R^{14}$ group is located at the 7-position on the 1,3-benzodioxol-4-yl group, $Z^2$ is a C≡C group; and $R^{14}$ is selected from cyano, formyl, carboxy, carbamoyl, vinyl, methoxycarbonyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, 1-pyrrolidinylcarbonyl, morpholinocarbonyl, 1,1-dioxotetrahydro-4H-1,4-thiazin-4-ylcarbonyl, piperidinocarbonyl, piperazin-1-ylcarbonyl, 1-pyrrolidinylmethyl, morpholinomethyl, piperidinomethyl, 1,1-dioxotetrahydro-4H-1,4-thiazin-4-ylmethyl, piperazin-1-ylmethyl and 3-morpholinopropyl;

or a pharmaceutically-acceptable acid-addition salt thereof.

A further particular compound of the invention is a quinoline derivative of the Formula I wherein:

$Z^1$ is NH;

m is 2 and the first $R^1$ group is located at the 5-position and is selected from N-methylpiperidin-4-yloxy and tetrahydro-2H-pyran-4-yloxy and the second $R^1$ group is located at the 7-position and is selected from methoxy and 3-morpholinopropoxy, n is 0 or n is 1 and $R^3$ is located at the 5-position of the 1,3-benzodioxol-4-yl group and is selected from a fluoro, chloro or bromo group;

the -Z²-R¹⁴ group is located at the 7-position on the 1,3-benzodioxol-4-yl group, Z² is a C≡C group; and R¹⁴ is selected from chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, pyridin-2-yl, 1-pyrrolidinylmethyl, morpholinomethyl, piperidinomethyl, 1,1-dioxotetrahydro-4H-1,4-thiazin-4-ylmethyl, piperazin-1-ylmethyl and 3-morpholinopropyl;

or a pharmaceutically-acceptable acid-addition salt thereof.

A further particular compound of the invention is a quinoline derivative of the Formula I wherein:

Z¹ is NH;

m is 2 and the first R¹ group is located at the 5-position and is selected from N-methylpiperidin-4-yloxy and tetrahydro-2H-pyran-4-yloxy and the second R¹ group is located at the 7-position and is selected from methoxy and 3-morpholinopropoxy, n is 0 or n is 1 and the R³ group, if present, is located at the 5-position of the 1,3-benziodioxol-4-yl group and is chloro;

the -Z²-R¹⁴ group is located at the 7-position on the 1,3-benzodioxol-4-yl group, Z² is a C≡C group; and R¹⁴ is selected from methoxymethyl and 2-methoxyethyl;

or a pharmaceutically-acceptable acid-addition salt thereof.

Particular compounds of the invention include, for example, the quinoline derivatives of the Formula I described hereinafter in Examples 1, 2, 3, 9(1) to 9(7), 10 and 11. Particular compounds also include 3-cyano-4-[6-chloro-4-(3-methoxyprop-1-ynyl)-2,3-methylenedioxyanilino]-7-methoxy-5-[(1-methylpiperidin-4-yl)oxy]quinoline, 3-cyano-7-methoxy-5-[(1-methylpiperidin-4-yl)oxy]-4-[4-(3-methoxyprop-1-ynyl)-2,3-methylenedioxyanilino] quinoline, 3-cyano-7-(3-morpholin-4-ylpropoxy)-5-(tetrahydro-2H-pyran-4-yloxy)-4-[4-(3-methoxyprop-1-ynyl)-2,3-methylenedioxyanilino]quinoline, 3-cyano-7-methoxy-4-[4-(4-methoxybut-1-ynyl)-2,3-methylenedioxyanilino]-5-[(1-methylpiperidin-4-yl)oxy] quinoline, 3-cyano-6-methoxy-7-[3-(4-methylpiperazin-1-yl)propoxy]4[4-(3-methoxyprop-1-ynyl)-2,3-methylenedioxyanilino]quinoline, 3-cyano-6,7-dimethoxy-4-[4-(pyridin-2-ylethynyl)-2,3-methylenedioxyanilino] quinoline, 3-cyano-6-methoxy-4-[4-(3-methoxyprop-1-ynyl)-2,3-methylenedioxyanilino]-7-[2-(2-pyrrolidin-1-ylethoxy)ethoxy]-quinoline, 4-[(4-but-3-en-1-ynyl-2,3-methylendioxy)anilino]-3-cyano-7-methoxy-5-[(1-methylpiperidin-4-yl)oxy]quinoline, 3-cyano-6-methoxy-7-[3-(4-methylpiperazin-1-yl)propoxy]-4-[6-fluoro-4-(3-methoxyprop-1-ynyl)-2,3-methylenedioxyanilino] quinoline, 3-cyano-6-methoxy-7-[2-fluoro-3-(4-hydroxypiperidin-1-yl)propoxy]-4-[4-(3-methoxyprop-1-ynyl)-2,3-methylenedioxyanilino]quinoline and 3-cyano-6-methoxy-7-[2-(2-methoxyethoxy)ethoxy]4-[4-(3-methoxyprop-1-ynyl)-2,3-methylenedioxyanilino] quinoline.

A quinoline derivative of the Formula I, or a pharmaceutically-acceptable salt thereof, may be prepared by any process known to be applicable to the preparation of chemically-related compounds. Such processes, when used to prepare a quinoline derivative of the Formula I are provided as a further feature of the invention and are illustrated by the following representative process variants in which, unless otherwise stated, m, R¹, Z¹, n, R³, Z² and R¹⁴ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) For the production of those compounds of the Formula I wherein Z¹ is an O, S or N(R²) group, the reaction of a quinoline of the Formula II

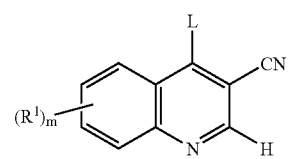

II wherein L is a displaceable group and m and R¹ have any of the meanings defined hereinbefore except that any functional group is protected if necessary, with a compound of the Formula III

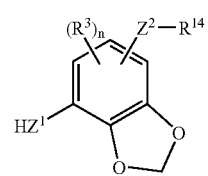

III wherein Z¹ is O, S, or N(R²) and n, R³, R², Z² and R¹⁴ have any of the meanings defined hereinbefore except that any functional group is protected if necessary, whereafter any protecting group that is present is removed by conventional means.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide N-methylpyrrolidin-2-one or dimethylsulphoxide. The reaction is conveniently carried out at a temperature in the range, for example, 0 to 250° C., preferably in the range 0 to 120° C.

Typically, the quinoline of the Formula II may be reacted with a compound of the Formula III in the presence of an aprotic solvent such as N,N-dimethylformamide, conveniently in the presence of a base, for example potassium carbonate or sodium hexamethyldisilazane, and at a temperature in the range, for example, 0 to 150° C., preferably in the range, for example, 0 to 70° C.

The quinoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower allyl groups (for example 1-methoxycarbonyloxyethyl and 1-ethoxycarbonyloxyethyl); aryllower alkyl groups (for example benzyl, 4-methoxybenzyl, 2-nitrobenzyl, 4-nitrobenzyl, benzhydryl and phthalidyl); tri(lower allyl)silyl groups (for example trimethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

Quinoline starting materials of the Formula II may be obtained by conventional procedures such as those disclosed in International Patent Applications WO 98/43960 and WO 00/68201. For example, a 1,4-dihydroquinolin-4-one of Formula IV

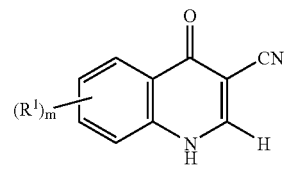

IV wherein m and $R^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinoline so obtained may be converted, if required, into a 4-pentafluorophenoxyquinoline by reaction with pentafluorophenol in the presence of a suitable base such as potassium carbonate and in the presence of a suitable solvent such as N,N-dimethylformamide.

2,3-Methylenedioxyanilino starting materials (Formula III, for example when Z is NH) may be obtained by conventional procedures as illustrated in the Examples. Corresponding 2,3-methylenedioxyphenol and 2,3-methylenedioxythiophenol starting materials (Formula III, when Z is O or S) may be obtained by conventional procedures.

(b) For the production of those compounds of the Formula I wherein at least one $R^1$ group is a group of the formula $$Q^1\text{-}X^1\text{—}$$

wherein $Q^1$ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group or an optionally substituted alkyl group and $X^1$ is an oxygen atom, the coupling, conveniently in the presence of a suitable dehydrating agent, of a quinoline of the Formula V

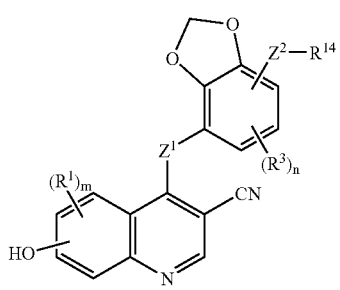

wherein m, $R^1$, $Z^1$, n, $R^3$, $Z^2$ and $R^{14}$ have any of the meanings defined hereinbefore except that any functional group is protected if necessary, with an appropriate alcohol of the formula $Q^1$-OH wherein any functional group is protected if necessary, whereafter any protecting group that is present is removed by conventional means.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(c) For the production of those compounds of the Formula I wherein $R^1$ is an amino-substituted (1–6C)alkoxy group (such as 2-homopiperidin-1-ylethoxy or 3-dimethylaminopropoxy), the reaction of a compound of the Formula I wherein $R^1$ is a halogeno-substituted (1–6C)alkoxy group with a heterocyclyl compound or an appropriate amine. The reaction is conveniently carried out in the presence of a suitable inert diluent or carrier as defined hereinbefore and at a temperature in the range 10 to 150° C., preferably at or near ambient temperature.

(d) For the production of those compounds of the Formula I wherein an $R^1$ group contains a (1–6C)alkoxy or substituted (1–6C)alkoxy group or a (1–6C)alkylamino or substituted (1–6C)alkylamino group, the alkylation, conveniently in the presence of a suitable base as defined hereinbefore, of a quinoline derivative of the Formula I wherein the $R^1$ group contains hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein $R^1$ contains a (1–6C)alkylamino or substituted (1–6C)alkylamino group, a reductive amination reaction may be employed. For example, for the production of those compounds of the Formula I wherein $R^1$ contains a N-methyl group, the corresponding compound containing a N—H group may be reacted with formaldehyde in the presence of a suitable reducing agent. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(e) For the production of those compounds of the Formula I wherein $Z^1$ is a SO or $SO_2$ group, wherein an $R^1$ or $R^3$ substituent is a (1–6C)alkylsulphinyl or (1–6C)alkylsulphonyl group or wherein an $R^1$, $R^3$ or $R^{14}$ substituent contains a SO or $SO_2$ group, the oxidation of a compound of Formula I wherein $Z^1$ is a S group or wherein an $R^1$ or $R^3$ substituent is a (1–6C)alkylthio group or wherein an $R^1$, $R^3$ or $R^{14}$ substituent contains a S group as appropriate.

Conventional oxidation reagents and reaction conditions for such partial or complete oxidation of a sulphur atom are well known to the organic chemist.

(f) The reaction, conveniently in the presence of a suitable base as defined hereinbefore and in the presence of a suitable catalyst, of a compound of the Formula VI

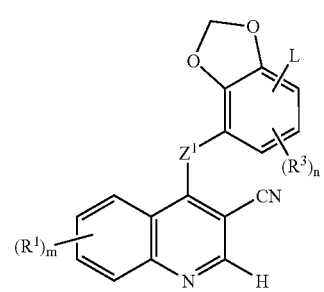

wherein L is a displaceable group as defined hereinbefore and m, $R^1$, $Z^1$, n and $R^3$ have any of the meanings defined hereinbefore except that any functional group is protected if necessary, with a compound of the Formula VII $$HZ^2\text{-}R^{14} \qquad\qquad VII$$

wherein $Z^2$ is a C≡C or $C(R^3)$=$C(R^{13})$ group and $R^{13}$ and $R^{14}$ have any of the meanings defined hereinbefore except that any functional group is protected if necessary, whereafter any protecting group that is present is removed by conventional means.

Conveniently the displaceable group is a halogeno group such as iodo, bromo or chloro. A suitable catalyst is, for example, an organometallic reagent, for example an organopalladium compound such as tetrakis(triphenylphosphine)palladium(0) or bis(triphenylphosphine)palladium(II) dichloride. The conversion reaction is conveniently carried out in the presence of a suitable inert diluent or carrier as defined hereinbefore and at a temperature in the range 10 to 150° C., preferably at or near 60° C.

(g) For the production of a compound of the Formula I wherein $R^{14}$ is a carboxy group, the cleavage of a compound of the Formula I wherein $R^{14}$ is a (1–6C)alkoxycarbonyl group.

The cleavage reaction is conveniently carried out by the hydrolysis of the (1–6C)alkoxycarbonyl group in the presence of a suitable base, for example an alkali or alkaline earth metal carbonate or hydroxide such as sodium carbonate, potassium carbonate, calcium carbonate, sodium hydroxide or potassium hydroxide and in the presence of a suitable inert diluent or carrier as defined hereinbefore such as methanol and at a temperature in the range 10 to 150° C., preferably at or near 40° C.

(h) The reaction, conveniently in the presence of a suitable dehydrating agent as defined hereinbefore, of a compound of the Formula I wherein $R^{14}$ is a carboxy group with an appropriate amine to form a further compound of the Formula I wherein $R^{14}$ is a carbamoyl, N-(1–6C)alkylcarbamoyl, N,N-di-[(1–6C)alkyl]carbamoyl or heterocyclylcarbonylamino group.

The reaction is conveniently carried out in the presence of a suitable inert diluent or carrier as defined hereinbefore and at a temperature in the range, for example, 10 to 150° C., preferably at or near ambient temperature.

When a pharmaceutically-acceptable salt of a quinoline derivative of the Formula I is required; for example an acid-addition salt, it may be obtained by, for example, reaction of said quinoline derivative with a suitable acid using a conventional procedure.

Biological Assays

The following assays can be used to measure the effects of the compounds as inhibitors of the MAPK pathway.

(a) Assay to Detect MEK Inhibition

To evaluate inhibitors of the MAPK pathway, a coupled assay was carried out which measures phosphorylation of serine/threonine residues present in the substrate in the presence or absence of inhibitor. Recombinant glutathione S-transferase fusion protein containing human p45MEK1 (GST-MEK) was activated by c-raf (Sf9 insect cell lysate from triple baculoviral infection with c-raf/ras/lck) and used for the assay. Active GST-MEK was first used to activate a recombinant glutathione S-transferase fusion protein containing p44MAP kinase (GST-MAPK) in the presence of ATP and $Mg^{2+}$ for 60 minutes at room temperature in the presence or absence of potential inhibitors. The activated GST-MAPK was then incubated with myelin basic protein (MBP) as substrate for 10 minutes at room temperature in the presence of ATP, $Mg^{2+}$ and $^{33}$P-ATP. The reaction was stopped by addition of 20% v/v phosphoric acid. Incorporation of $^{33}$P into the myelin basic protein was determined by capture of the substrate on a filter mat, washing and counting using scintillation methods. The extent of inhibition was determined by comparison with untreated controls.

The final assay solution contained 10 mM Tris, pH 7.5, 0.05 mM EGTA, 8.33 µM [γ$^{33}$P]ATP, 8.33 mM Mg(OAc)$_2$, 0.5 mM sodium orthovanadate, 0.05% w/v BSA, 6.5 ng GST-MEK, log GST-MAPK and 16.5 µg MBP in a reaction volume of 60 µl.

(b) In Vitro MAP Kinase Assay

To determine whether compounds were inhibiting GST-MEK or GST-MAPK, a direct assay of MAPK activity was employed. GST-MAPK was activated by a constitutively active GST-MEK fusion protein containing two point mutations (S217E, S221E) and used for the assay in the presence and absence of potential inhibitors. The activated GST-MAPK was incubated with substrate (MBP) for 60 min at room temperature in the presence of ATP, $Mg^{2+}$ and $^{33}$P-ATP. The reaction was stopped by addition of 20% v/v phosphoric acid. Incorporation of $^{33}$P into the myelin basic protein was determined by capture of the substrate on a filter mat, washing and counting using scintillation methods.

The final assay solution contained 12 mM Tris, pH 7.5, 0.06 mM EGTA, 30 µM [γ$^{33}$P]ATP, 10 mM Mg(OAc)$_2$, 0.6 mM sodium orthovanadate, 0.06% w/v BSA, 28 ng GST-MAPK and 16.5 µg MBP in a reaction volume of 60 µl;

(c) Cell Proliferation Assays

Cells were seeded into multi-well plates at 20,000–40,000 cells/ml in growth medium containing 5% FCS and incubated overnight at 37° C. The compounds were prepared in fresh medium at an appropriate concentration and added to the wells containing the cells. These were then incubated for a further 72 hours. Cells were then either removed from the wells by incubating with trypsin/EDTA and counted using a Coulter counter, or treated with XTT/PMS in PBSA and optical densities read at 450 nm.

The following assays can be used to measure the effects of the compounds of the present invention as c-Src tyrosine kinase inhibitors, as inhibitors in vitro of the proliferation of c-Src transfected fibroblast cells, as inhibitors in vitro of the migration of A549 human lung tumour cells and as inhibitors in vivo of the growth in nude mice of xenografts of A549 tissue.

(d) In Vitro Src Enzyme Assay

The ability of test compounds to inhibit the phosphorylation of a tyrosine containing polypeptide substrate by the enzyme c-Src kinase was assessed using a conventional Elisa assay.

A substrate solution [100 µl of a 20 µg/ml solution of the polyamino acid Poly(Glu, Tyr) 4:1 (Sigma Catalogue No. P0275) in phosphate buffered saline (PBS) containing 0.2 mg/ml of sodium azide] was added to each well of a number of Nunc 96-well immunoplates (Catalogue No. 439454) and the plates were sealed and stored at 4° C. for 16 hours. The excess of substrate solution was discarded, and aliquots of Bovine Serum Albumin (BSA; 150 µl of a 5% solution in PBS) were transferred into each substrate-coated assay well and incubated for 1 hour at ambient temperature to block non specific binding. The assay plate wells were washed in turn with PBS containing 0.05% v/v Tween 20 (PBST) and with Hepes pH7.4 buffer (50 mM, 300 µl/well) before being blotted dry.

Each test compound was dissolved in dimethyl sulphoxide and diluted with distilled water to give a series of dilutions (from 100 μM to 0.001 μM). Portions (25 μl) of each dilution of test compound were transferred to wells in the washed assay plates. "Total" control-wells contained diluted DMSO instead of compound. Aliquots (25 μl) of an aqueous magnesium chloride solution (80 mM) containing adenosine-5'-triphosphate (ATP; 40 μM) was added to all test wells except the "blank" control wells which contained magnesium chloride without ATP.

Active human c-Src kinase (recombinant enzyme expressed in Sf9 insect cells; obtained from Upstate Biotechnology Inc. product 14–117) was diluted immediately prior to use by a factor of 1:10,000 with an enzyme diluent which comprised 100 mM Hepes pH7.4 buffer, 0.2 mM sodium orthovanadate, 2 mM dithiothreitol and 0.02% BSA. To start the reactions, aliquots (50 μl) of freshly diluted enzyme were added to each well and the plates were incubated at ambient temperature for 20 minutes. The supernatant liquid in each well was discarded and the wells were washed twice with PBST. Mouse IgG anti-phosphotyrosine antibody (Upstate Biotechnology Inc. product 05–321; 100 μl) was diluted by a factor of 1:6000 with PBST containing 0.5% w/v BSA and added to each well. The plates were incubated for 1 hour at ambient temperature. The supernatant liquid was discarded and each well was washed with PBST (×4). Horse radish peroxidase (HRP)-linked sheep anti-mouse Ig antibody (Amersham Catalogue No. NXA 931; 100 μl) was diluted by a factor of 1:500 with PBST containing 0.5% w/v BSA and added to each well. The plates were incubated for 1 hour at ambient temperature. The supernatant liquid was discarded and the wells were washed with PBST (×4).

A PCSB capsule (Sigma Catalogue No. P4922) was dissolved in distilled water (100 ml) to provide phosphate-citrate pH5 buffer (50 mM) containing 0.03% sodium perborate. An aliquot (50 ml) of this buffer was mixed with a 50 mg tablet of 2,2'-azinobis(3-ethylbenzothiazoline-6-sulphonic acid) (ABTS; Boehringer Catalogue No. 1204 521). Aliquots (100 μL) of the resultant solution were added to each well. The plates were incubated for 20 to 60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(e) In Vitro c-Src Transfected NIH 3T3 (c-src 3T3) Fibroblast Proliferation Assay This assay determined the ability of a test compound to inhibit the proliferation of National Institute of Health (NIH) mouse 3T3 fibroblast cells that had been stably-transfected with an activating mutant (Y530F) of human c-Src.

Using a similar procedure to that described by Shalloway et al., Cell, 1987, 49, 65–73, NIH 3T3 cells were transfected with an activating mutant (Y530F) of human c-Src. The resultant c-Src 3T3 cells were typically seeded at $1.5 \times 10^4$ cells per well into 96-well tissue-culture-treated clear assay plates (Costar) each containing an assay medium comprising Dulbecco's modified Eagle's medium (DMEM; Sigma) plus 0.5% foetal calf serum (FCS), 2 mM glutamine, 100 units/ml penicillin and 0.1 mg/ml streptomycin in 0.9% aqueous sodium chloride solution. The plates were incubated overnight at 37° C. in a humidified (7.5% $CO_2$: 95% air) incubator.

Test compounds were solubilised in DMSO to form a 10 mM stock solution. Aliquots of the stock solution were diluted with the DMEM medium described above and added to appropriate wells. Serial dilutions were made to give a range of test concentrations. Control wells to which test compound was not added were included on each plate. The plates were incubated overnight at 37° C. in a humidified (7.5% $CO_2$: 95% air) incubator.

BrdU labelling reagent (Boehringer Mannheim Catalogue No. 647 229) was diluted by a factor of 1:100 in DMEM medium containing 0.5% FCS and aliquots (20 μl) were added to each well to give a final concentration of 10 μl). The plates were incubated at 37° C. for 2 hours. The medium was decanted. A denaturating solution (FixDenat solution, Boehringer Mannheim Catalogue No. 647 229; 50 μl) was added to each well and the plates were placed on a plate shaker at ambient temperature for 45 minutes. The supernatant was decanted and the wells were washed with PBS (200 μl per well). Anti-BrdU-Peroxidase solution (Boehringer Mannheim Catalogue No. 647 229) was diluted by a factor of 1:100 in PBS containing 1% BSA and 0.025% dried skimmed milk (Marvel (registered trade mark), Premier Beverages, Stafford, GB) and an aliquot (100 μl) of the resultant solution was added to each well. The plates were placed on a plate shaker at ambient temperature for 90 minutes. The wells were washed with PBS (×5) to ensure removal of non-bound antibody conjugate. The plates were blotted dry and tetramethylbenzidine substrate solution (Boehringer Mannheim Catalogue No. 647 229; 100 μl) was added to each well. The plates were gently agitated on a plate shaker while the colour developed during a 10 to 20 minute period. The absorbance of the wells was measured at 690 nm. The extent of inhibition of cellular proliferation at a range of concentrations of each test compound was determined and an anti-proliferative $IC_{50}$ value was derived.

(f) In Vitro Microdroplet Migration Assay

This assay determines the ability of a test compound to inhibit the migration of adherent mammalian cell lines, for example the human tumour cell line A549.

RPMI medium(Sigma) containing 10% FCS, 1% L-glutamine and 0.3% agarose (Difco Catalogue No. 0142-01) was warmed to 37° C. in a water bath. A stock 2% aqueous agar solution was autoclaved and stored at 42° C. An aliquot (1.5 ml) of the agar solution was added to RPMI medium (10 ml) immediately prior to its use. A549 cells (Accession No. ATCC CCL185) were suspended at a concentration of $2 \times 10^7$ cells/ml in the medium and maintained at a temperature of 37° C.

A droplet (2 μl) of the cell/agarose mixture was transferred by pipette into the centre of each well of a number of 96-well, flat bottomed non-tissue-culture-treated microtitre plate (Bibby Sterilin Catalogue No. 642000). The plates were placed briefly on ice to speed the gelling of the agarose-containing droplets. Aliquots (90 μl) of medium which had been cooled to 4° C. were transferred into each well, taking care not to disturb the microdroplets. Test compounds were diluted from a 10 mM stock solution in DMSO using RPMI medium as described above. Aliquots (10 μl) of the diluted test compounds were transferred to the wells, again taking care not to disturb the microdroplets. The plates were incubated at 37° C. in a humidified (7.5% $CO_2$: 95% air) incubator for about 48 hours.

Migration was assessed visually and the distance of migration was measured back to the edge of the agar droplet.

A migratory inhibitory $IC_{50}$ was derived by plotting the mean migration measurement against test compound concentration.

(g) In Vivo A549 Xenograft Growth Assay

This test measures the ability of compounds to inhibit the growth of the A549 human carcinoma grown as a tumour in athymic nude mice (Alderley Park nu/nu strain). A total of about $5 \times 10^6$ A549 cells in matrigel (Beckton Dickinson Catalogue No. 40234) were injected subcutaneously into the left flank of each test mouse and the resultant tumours were allowed to grow for about 14 days. Tumour size was measured twice weekly using callipers and a theoretical volume was calculated. Animals were selected to provide control and treatment groups of approximately equal average tumour volume. Test compounds were prepared as a ball-milled suspension in 1% polysorbate vehicle and dosed orally once daily for a period of about 28 days. The effect on tumour growth was assessed.

Although the pharmacological properties of the compounds of the Formula I vary with structural change as expected, in general activity possessed by compounds of the Formula I, may be demonstrated at the following concentrations or doses in one or more of the above tests (a) to (g):

Test (a):—$IC_{50}$ in the range, for example, less than 4 µM;
Test (b):—activity was observed in this screen;
Test (c):—$IC_{50}$ in the range, for example, less than 30 µM.
Test (d):—$IC_{50}$ in the range, for example, 0.001–10 µM;
Test (d):—$IC_{50}$ in the range, for example, 0.01–20 µM;
Test (f):—activity in the range, for example, 0.1–25 µM;
Test (g):—activity in the range, for example, 1–200 mg/kg/day;

No physiologically-unacceptable toxicity was observed in Test (g) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinoline derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinoline derivative of the Formula I, or a pharmaceutically-acceptable salt thereof, as defined hereinbefore for use in a method of treatment of the human or animal body by therapy.

According to a further aspect of the invention there is provided a quinoline derivative of the Formula I, or a pharmaceutically-acceptable salt thereof, as defined hereinbefore for use in the treatment or cancer.

As stated above we have also found that the quinoline derivatives of the present invention of Formula I possess potent anti-tumour activity which it is believed is obtained by way of inhibition of one or more of the MEK enzymes that are involved in the MAPK pathway.

Accordingly, the quinoline derivatives of Formula I are of value as anti-proliferative agents in the containment and/or treatment of solid tumour disease. Particularly, the compounds of Formula I are expected to be useful in the prevention or treatment of those tumours which are sensitive to inhibition of one or more of the MEK enzymes that are involved in the MAPK pathway. Further, the compounds of Formula I are expected to be useful in the prevention or treatment of those tumours which are mediated alone or in part by inhibition of the MEK enzymes i.e. the compounds may be used to produce a MEK enzyme inhibitory effect in a warm-blooded animal in need of such treatment. Specifically, the compounds of Formula I are expected to be useful in the prevention or treatment of solid tumour disease.

Thus, according to this aspect of the invention there is provided of a quinoline derivative of the Formula I, or a pharmaceutically-acceptable salt thereof, as defined hereinbefore for use as an anti-proliferative agent in the containment and/or treatment of solid tumour disease.

According to a farther aspect of the invention there is provided the use of a quinoline derivative of the Formula I, or a pharmaceutically-acceptable salt thereof, as defined hereinbefore in the manufacture of a medicament for use as an anti-proliferative agent in the containment and/or treatment of solid tumour disease.

According to a further feature of the invention there is provided a method for producing an anti-proliferative effect by the containment and/or treatment of solid tumour disease in a warm-blooded animal, such as man, in need of such treatment which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in the prevention or treatment of solid tumour disease in a warm-blooded animals such as man.

According to a further feature of this aspect of the invention there is provided a method for the prevention or treatment of solid tumour disease in a warm-blooded animal, such as man, in need of such treatment which comprises administering to said animal an effective amount of a quinoline derivative of the Formula 1, or a pharmaceutically-acceptable salt thereof as defined hereinbefore.

According to a further aspect of the invention there is provided the use of a quinoline derivative of the Formula I, or a pharmaceutically-acceptable salt thereof, as defined hereinbefore in the manufacture of a medicament for use in the prevention or treatment of those tumours which are sensitive to inhibition of MEK enzymes that are involved in the MAPK pathway. Particular enzymes that the tumours may be sensitive to are MEK 1, MEK 2 and MEK 5.

According to a further feature of this aspect of the invention there is provided a method for the prevention or treatment of those tumours which are sensitive to inhibition of MEK enzymes that are involved in the MAPK pathway which comprises administering to said animal an effective amount of a quinoline derivative of the Formula L or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in providing a MEK enzyme inhibitory effect.

According to a further feature of this aspect of the invention there is provided a method for providing a MEK enzyme inhibitory effect which comprises administering to said animal an effective amount of a quinoline derivative of the Formula I, or a pharmaceutically-acceptable salt thereof, as defined hereinbefore.

We have also found that the quinoline derivatives of the present invention possess potent anti-tumour activity which it is believed is obtained by way of inhibition of one or more of the non-receptor tyrosine-specific protein kinases such as c-Src kinase that are involved in the signal transduction steps which lead to the invasiveness and migratory ability of metastasising tumour cells.

Particularly, the quinoline derivatives of the present invention are of value as anti-invasive agents in the containment and/or treatment of solid tumour disease. Particularly, the compounds of the present invention are expected to be useful in the prevention or treatment of those tumours which are sensitive to inhibition of one or more of the multiple non-receptor tyrosine kinases such as c-Src kinase that are involved in the signal transduction steps which lead to the invasiveness and migratory ability of metastasising tumour cells. Further, the compounds of the present invention are expected to be useful in the prevention or treatment of those tumours which are mediated alone or in part by inhibition of the enzyme c-Src, i.e. the compounds may be used to produce a c-Src enzyme inhibitory effect in a warm-blooded animal in need of such treatment. Specifically, the compounds of the present invention are expected to be useful in the prevention or treatment of solid tumour disease.

According to this aspect of the invention there is provided a quinoline derivative of the Formula I, or a pharmaceutically-acceptable salt thereof, as defined hereinbefore for use as an anti-invasive agent in the containment and/or treatment of solid tumour disease.

According to a further feature of this aspect of the invention there is provided the use of a quinoline derivative of the Formula I, or a pharmaceutically-acceptable salt thereof, as defined hereinbefore in the manufacture of a medicament for use as an anti-invasive agent in the containment and/or treatment of solid tumour disease.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in the prevention or treatment of those tumours which are sensitive to inhibition of non-receptor tyrosine kinases such as c-Src kinase that are involved in the signal transduction steps which lead to the invasiveness and migratory ability of metastasising tumour cells.

According to a further feature of this aspect of the invention there is provided a method for the prevention or treatment of those tumours which are sensitive to inhibition of non-receptor tyrosine kinases such as c-Src kinase that are involved in the signal transduction steps which lead to the invasiveness and migratory ability of metastasising tumour cells which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in providing a c-Src kinase inhibitory effect.

According to a further feature of this aspect of the invention there is provided a method for providing a c-Src kinase inhibitory effect which comprises administering to said animal an effective amount of a quinoline derivative of the Formula I, or a pharmaceutically-acceptable salt thereof, as defined hereinbefore.

The anti-proliferative and anti-invasive treatment defined hereinbefore may be applied as a sole therapy or may involve, in addition to the quinoline derivative of the invention, conventional surgery or radiotherapy or chemotherapy. Such chemotherapy may include one or more of the following categories of anti-tumour agents:

(i) other anti-invasion agents (for example metalloproteinase inhibitors like marimastat and inhibitors of urokinase plasminogen activator receptor function);

(ii) other anti-proliferative or antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylm-ethyl)-N-(prop-2-ynyl)amino]benzamido}-4-(tetrazol-5-yl)butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5 α-reductase such as finasteride;

(iv) inhibitors of growth factor function, for example such inhibitors include growth factor antibodies, growth factor receptor antibodies, farnesyl transferase inhibitors, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin $\alpha v \beta_3$ function and angiostatin);

(vi) antisense therapies, for example those which are directed to the targets listed above, such as ISIS 2503, an anti-ras antisense;

(vii) gene therapy approaches, including for example approaches to replace aberrant genes such as aberrant p53 or aberrant BRCA1, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinoline derivative of the formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of the MEK enzymes that are involved in the MAPK kinase pathway or the effects of c Src. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, Where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture;

(viii) the following abbreviations have been used:

DMF N,N-dimethylform amide

DMSO dimethylsulphoxide

THF tetrahydrofuran

EXAMPLE 1

3-cyano-6,7-dimethoxy-4-[4-(3-methoxyprop-1-ynyl)-2,3-methylenedioxyanilino]quinoline monohydrochloride salt A mixture of 3-cyano-4-(4-iodo-2,3-methylenedioxyanilino)-6,7-dimethoxyquinoline (0.2 g), methyl 2-propynyl ether (0.071 ml), tetrakis(triphenylphosphine)palladium(0) (0.05 g), cuprous iodide (0.01 g) and N,N-diethylamine (4 ml) was stirred and heated to 60° C. for 4 hours. The reaction mixture was evaporated and the residue was partitioned between methylene chloride and a 2N aqueous hydrochloric acid solution. The precipitate that was formed was isolated by filtration, washed in turn with methylene chloride, ethanol and diethyl ether and dried. There was thus obtained the title compound (0.085 g); NMR Spectrum: (DMSOd$_6$) 3.33 (s, 3H), 3.98 (s, 3H), 3.99 (s, 3H), 4.36 (s, 2H), 6.12 (s, 2H), 6.98 (d, 1H), 7.02 (d, 1H), 7.47 (s, 1H), 8.13 (s, 1H), 8.98 (s, 1H); Mass Spectrum: M+H$^+$ 418.

The 3-cyano-4-(4-iodo-2,3-methylenedioxyanilino)-6,7-dimethoxyquinoline used as a starting material was prepared as follows:

Sodium hexamethyldisilazane (1M solution in THF; 3.8 ml) was added to a solution of 4-iodo-2,3-methylenedioxyaniline (0.5 g) in DMF (1.2 ml) that was cooled to 0° C. and the mixture was stirred for 5 minutes. A solution of 4-chloro-3-cyano-6,7-dimethoxyquinoline (International Patent Application WO 98/43960; 0.43 g) in DMF (3 ml) was added and the resultant mixture was stirred at ambient temperature for 2 hours. The reaction mixture was diluted with water and extracted with ethyl acetate. The organic phase was washed with water and with a saturated brine solution, dried over magnesium sulphate and evaporated. The residue was purified by column chromatography on silica increasingly polar mixtures of methylene chloride and ethyl acetate as eluent. There was thus obtained 3-cyano-4-(4-iodo-2,3-methylenedioxyanilino)-6,7-dimethoxyquinoline as a solid (0.8 g); NMR Spectrum: (DMSOd$^6$) 3.77 (s, 3H), 3.81 (s, 3H), 5.88 (s, 2H), 6.3 (d, 1H), 6.87 (d, 1H), 6.93 (s, 1H), 7.7 (s, 1H), 7.83 (s, 1H); Mass Spectrum: M+H$^+$ 476.

The 4-iodo-2,3-methylenedioxyaniline used as a starting material was prepared as follows:

A mixture of 2,3-dihydroxybenzoic acid (5 g), methanol (50 ml) and concentrated sulphuric acid (10 drops) was stirred and heated to 60° C. for 24 hours. The mixture was evaporated and the residue was taken up in ethyl acetate. The organic solution was washed with a saturated solution of sodium bicarbonate, dried over magnesium sulphate and evaporated to give methyl 2,3-dihydroxybenzoate (2.19 g); NMR Spectrum: (CDCl$_3$) 3.95 (s, 3H), 5.7 (s, 1H), 6.8 (t, 1H), 7.15 (d, H), 7.35 (d, H).

After repetition of the previous reaction, a mixture of methyl 2,3-dihydroxybenzoate (2.8 g), potassium fluoride (4.8 g) and DMF (45 ml) was stirred at ambient temperature for 30 minutes. Dibromomethane (1.28 ml) was added and the mixture was heated to 120° C. for 3 hours. The mixture was cooled to ambient temperature, poured into water and extracted with diethyl ether. The organic phase was washed with water and with a saturated brine solution, dried over magnesium sulphate and evaporated. The residue was purified by column chromatography using a 9:1 mixture of petroleum ether (b.p. 40–60° C.) and ethyl acetate as eluent. There was thus obtained methyl 2,3-methylenedioxybenzoate (2.3 g) as a solid; NMR Spectrum: (CDCl$_3$) 3.95 (s, 3H), 6.1 (s, 2H), 6.85 (t, 1H), 7.0 (d, 1H), 7.45 (d, 1H).

A mixture of the material so obtained, a 2N aqueous potassium hydroxide solution (15.5 ml) and methanol (40 ml) was stirred at ambient temperature for 2 hours. The solution was concentrated to about one quarter of the original volume and cooled in an ice bath. The mixture was acidified to pH3.5 by the addition of a 2N aqueous hydrochloric acid solution. The resultant precipitate was collected by filtration and washed in turn with water and diethyl ether. There was thus obtained 2,3-methylenedioxybenzoic acid (1.87 g); NMR Spectrum: (DMSOd$_6$) 6.1 (s, 1H), 6.9 (t, 1H), 7.15 (d, 1H), 7.3 (d, 1H), 13.0 (br s, 1H).

The material so obtained was suspended in anhydrous dioxane (30 ml) and anhydrous diphenylphosphoryl azide (2.45 ml), triethylamine (1.6 ml) and tert-butanol (9 ml) were added. The mixture was heated to reflux for 5 hours. The mixture was cooled to ambient temperature, concentrated by evaporation and diluted with ethyl acetate. The organic phase was washed in turn with a 5% aqueous citric acid solution, water, an aqueous sodium bicarbonate solution and a saturated brine solution and dried over magnesium sulphate. The solvent was evaporated and the residue was purified by column chromatography on silica using a 19:1 mixture of petroleum ether (b.p. 40–60° C.) and ethyl acetate as eluent. There was thus obtained tert-butyl N-(2,3-methylenedioxyphenyl)carbamate (1.98 g) as a solid; NMR Spectrum: (CDCl$_3$) 1.55 (s, 9H), 5.95 (s, 2H), 6.4 (br s, 1H), 6.55 (d, 1H), 6.8 (t, 1H), 7.45 (d, 1H).

A 5N aqueous hydrochloric acid solution (30 ml) was added to a solution of tert-butyl N-(2,3-methylenedioxyphenyl)carbamate (1.9 g) in ethanol (38 ml) and the reaction mixture was stirred at ambient temperature for 20 hours. The ethanol was evaporated and the residual aqueous phase was washed with diethyl ether and neutralised to pH7 by the addition of solid potassium hydroxide. The resultant mixture was filtered and the aqueous phase was extracted with diethyl ether. The organic phase was washed with a saturated brine solution, dried over magnesium sulphate and evaporated. There was thus obtained 2,3-methylenedioxyaniline (1.0 g) as an oil; NMR Spectrum: (CDCl$_3$) 3.0 (br s, 2H), 5.9 (s, 2H), 6.3 (m, 2H), 7.25 (t, 1H).

Benzyltrimethylammonium dichloroiodate (2.8 g) was added portionwise during 10 minutes to a stirred mixture of 2,3-methylenedioxyaniline (1 g), calcium carbonate (0.95 g), methanol (5 ml) and methylene chloride (10 ml). The reaction mixture was stirred at ambient temperature for 1.5 hours. The resultant mixture was diluted with water and extracted with methylene chloride. The organic phase was washed with water and with a saturated-brine solution, dried over magnesium sulphate and evaporated. The residue was purified by column chromatography on silica using increasingly polar mixtures of isohexane, and methylene chloride as eluent. There was thus obtained 4-iodo-2,3-methylenedioxyaniline as a solid (1.1 g); NMR Spectrum: (DMSOd$_6$) 5.04 (br s, 2H), 5.94 (s, 2H), 6.13 (d, 1H), 6.8 (d, 1H).

EXAMPLE 2

3-cyano-6,7-dimethoxy-4-[6-chloro-4-(3-methoxyprop-1-ynyl)-2,3-methylene dioxyanilino]quinoline A mixture of 4-(6-chloro-4-iodo-2,3-methylenedioxyanilino)-3-cyano-6,7-dimethoxyquinoline (0.25 g), methyl 2-propynyl ether (0.09 ml), N,N-diisopropylamine (0.154 ml), bis(triphenylphosphine)palladium(II) dichloride (0.069 g), cuprous iodide (0.028 g) and ethyl acetate (10 ml) was stirred and heated to reflux for 12 hours. The reaction mixture was cooled to ambient temperature and partitioned between ethyl acetate and water. The organic layer was dried over magnesium sulphate and evaporated and the residue was purified by column chromatography on silica using increasingly polar mixtures of hexane and ethyl acetate as eluent. There was thus obtained the title compound as an oil (0.138 g); NMR Spectrum: (DMSOd$_6$) 3.42 (s, 3H), 3.97 (s, 3H), 3.99 (s, 3H), 4.38 (s, 2H), 6.17 (s, 2H), 7.13 (s, 1H), 7.36 (s, 1H), 7.92 (s, 1H), 8.39 (s, 1H), 9.42 (br s, 1H); Mass Spectrum: M+H$^+$ 452.

The 4-(6-chloro-4-iodo-2,3-methylenedioxyanilino)-3-cyano-6,7-dimethoxyquinoline used as a starting material was prepared as follows:

Using an analogous procedure to that described in the portion of Example 1 that is concerned with the preparation of starting materials, 4-chloro-3-cyano-6,7-dimethoxyquinoline (1.74 g) was reacted with 6-chloro-4-iodo-2,3-methylenedioxyaniline (2.5 g) to give 4-(6-chloro-4-iodo-2,3-methylenedioxyanilino)-3-cyano-6,7-dimethoxyquinoline as a solid (2.59 g) which gave the following characterising data; NMR Spectrum: (DMSOd$_6$) 4.0 (s, 6H), 6.18 (s, 2H), 7.38 (s, 1H), 7.48 (s, 1H), 7.88 (s, 1H), 8.44 (s, 1H), 9.45 (s, 1H); Mass Spectrum: M+H$^+$ 510.

The 6-chloro-4-iodo-2,3-methylenedioxyaniline used as a starting material was prepared as follows:

Sulphuryl chloride (72.5 ml) was added dropwise during 1.7 hours to a stirred mixture of benzodioxole (100 g), aluminium trichloride (0.43 g) and diphenyl sulphide (0.55 ml). Once the reaction started with the evolution of sulphur dioxide, the reaction mixture was cooled in a water bath to a temperature of approximately 22° C. After completion of the addition, the reaction mixture was stirred at ambient temperature for 45 minutes. The reaction mixture was degassed under vacuum and filtered and the filtrate was distilled at atmospheric pressure using a Vigreux distillation column. There was thus obtained 5-chloro-1,3-benzodioxole; b.p. 185–187° C.; NMR Spectrum: (CDCl$_3$) 6.0 (s, 2H); 6.7 (d, 1H); 6.75–6.9 (m, 2H).

A mixture of diisopropylamine (4.92 ml) and THF (100 ml) was cooled to −78° C. and n-butyllithium (2.5 M in hexane, 14 ml) was added dropwise. The mixture was stirred at −78° C. for 15 minutes. 5-Chloro-1,3-benzodioxole (3.73 ml) was added dropwise and the reaction mixture was stirred at −78° C. for 30 minutes. Dry carbon dioxide gas was bubbled into the reaction mixture for 30 minutes. The resultant reaction mixture was allowed to warm to ambient temperature and was stirred for a further hour. Water was added and the organic solvent was evaporated. The residue was acidified to pH2 by the addition of 2N aqueous hydrochloric acid solution. The resultant solid was isolated and washed in turn with water and diethyl ether. There was thus obtained 5-chloro-1,3-benzodioxole-4-carboxylic acid (5.4 g); NMR Spectrum: (DMSOd$_6$) 6.15 (s, 2H), 7.0 (m, 2H), 13.7 (br s, 1H).

A portion (1 g) of the material so obtained was dissolved in 1,4-dioxane (15 ml) and anhydrous tert-butanol (4 ml), diphenylphosphoryl azide (1.12 ml) and triethylamine (0.73 ml) were added in turn. The resultant mixture was stirred and heated to 100° C. for 4 hours. The mixture was evaporated and the residue was partitioned between ethyl acetate and a 5% aqueous citric acid solution. The organic phase was washed in turn with water, a saturated aqueous sodium bicarbonate solution and a saturated brine solution, dried over magnesium sulphate and evaporated. The residue was purified by column chromatography on silica using a 9:1 mixture of petroleum ether (b.p. 40–60° C.) and ethyl acetate as eluent. There was thus obtained tert-butyl N-(5-chloro-1,3-benzodioxol-4-yl)carbamate (1.1 g); NMR Spectrum: (DMSOd$_6$) 1.45 (s, 9H), 6.1 (s, 2H), 6.85 (d, 1H), 6.95 (d, 1H), 8.75 (s, 1H).

A mixture of the material so obtained (1.1 g), trifluoroacetic acid (6 ml) and methylene chloride (20 ml) was stirred at ambient temperature for 3 hours. The solvent was evaporated and the residue was partitioned between ethyl acetate and a saturated aqueous sodium bicarbonate solution. The organic phase was washed with a saturated brine solution, dried over magnesium sulphate and evaporated. There was thus obtained 6-chloro-2,3-methylenedioxyaniline (0.642 g); NMR Spectrum: DMSOd$_6$) 5.15 (s, 2H), 6.0 (s, 2H), 6.25 (d, 1H), 6.75 (d, 1H).

6-Chloro-2,3-methylenedioxyaniline was reacted with benzyltrimethylammonium dichloroiodate in an analogous manner to that described in the last paragraph of the portion of Example 1 that is concerned with the preparation of starting materials. There was thus obtained 4-(6-chloro-4-iodo-2,3-methylenedioxyanilino)-3-cyano-6,7-dimethoxyquinoline which gave the following characterising data; NMR Spectrum: (DMSOd$_6$) 6.04 (s, 2H), 7.0 (s, 1H).

EXAMPLE 3

3-cyano-7-ethoxy-6-methoxy-4-[4-(3-methoxyprop-1-ynyl)-2,3-methylenedioxyanilino]quinoline monohydrochloride salt Sodium hexamethyldisilazane (1M solution in THF; 1.17 ml) was added to a stirred mixture of 4-(3-methoxyprop-1-ynyl)-2,3-methylenedioxyaniline (0.12 g), 4-chloro-3-cyano-7-ethoxy-6-methoxyquinoline (0.146 g) and DMF (8 ml) that had been cooled to 0° C. and the resultant mixture was allowed to warm to ambient temperature and was stirred for 2 hours. The reaction mixture was diluted with water and extracted with ethyl acetate. The organic phase was washed with water and with a saturated brine solution, dried over magnesium sulphate and evaporated. The residue was purified by column chromatography on silica increasingly polar mixtures of methylene chloride and methanol as eluent. The material so obtained was dissolved in the minimum quantity of methylene chloride. The solution was diluted with diethyl ether and a solution of hydrogen chloride in diethyl ether (1M) was added. The resultant solid was isolated, washed with diethyl ether and dried. Thereby, the product was obtained the title compound (0.18 g); NMR Spectrum: (DMSOd$_6$) 1.44 (t, 3H), 3.33 (s, 3H), 4.0 (s, 3H), 4.24 (q, 2H), 4.36 (s, 2H), 6.12 (s, 2H), 6.96 (d, 1H), 7.03 (d, 1H), 7.45 (s, 1H), 8.11 (s, 1H), 8.96 (s, 1H); Mass Spectrum: M+H$^+$ 432.

The 4-chloro-3-cyano-7-ethoxy-6-methoxyquinoline used as a starting material was prepared as follows:

Diethyl azodicarboxylate (2.6 g) was added dropwise to a suspension of 4-chloro-3-cyano-7-hydroxy-6-methoxyquinoline (1.5 g; prepared as described in International Patent Application WO 00/68201, disclosed as compound (7) within Preparation 1 therein), ethanol (0.441 g), triphenylphosphine (2.18 g) and methylene chloride (15 ml) and the mixture was stirred at ambient temperature for 16 hours. The resultant mixture was washed with water and with a saturated brine solution. The organic phase was dried over magnesium sulphate and evaporated. The residue was purified by column chromatography on silica using increasingly polar mixtures of methylene chloride and ethyl acetate. There was thus obtained 4-chloro-3-cyano-7-ethoxy-6-methoxyquinoline as a solid (0.225 g); NMR Spectrum:

(DMSOd$_6$ at 100° C.) 1.39–1.48 (m, 3H), 4.0 (s, 3H), 4.25–4.35 (m, 2H), 7.46 (s, 1H), 7.5 (s, 1H), 8.89 (s, 1H); Mass Spectrum: M+H$^+$ 263.

The 4-(3-methoxyprop-1-ynyl)-2,3-methylenedioxyaniline used as a starting material was prepared as follows:

N,N-Diisopropylamine (0.231 g) was added to a stirred mixture of 4-iodo-2,3-methylenedioxyaniline (0.3 g), methyl 2-propynyl ether (0.16 g), bis(triphenylphosphine)palladium(II) dichloride (0.16 g), cuprous iodide (0.065 g) and ethyl acetate (10 ml) that had been cooled to −20° C. The resultant mixture was allowed to warm to ambient temperature and was stirred for 16 hours. The reaction mixture was partitioned between ethyl acetate and a saturated aqueous sodium bicarbonate solution. The organic layer was washed with water and with a saturated brine solution, dried over magnesium sulphate and evaporated. The residue was purified by column chromatography on silica using increasingly polar mixtures of isohexane and methylene chloride as eluent. There was thus obtained 4-(3-methoxyprop-1-ynyl)-2,3-methylenedioxyaniline as a gum (0.2 g); NMR Spectrum: (DMSOd$_6$) 3.28 (s, 3H), 4.25 (s, 2H), 5.29 (s, 2H), 5.94 (s, 2H), 6.2 (d, 1H), 6.64 (d, 1H).

EXAMPLE 4

3-cyano-6,7-dimethoxy-4-{4-[3-(1,1-dioxotetrahydro-4H-thiazin-4-yl)prop-1-ynyl]-2,3-methylenedioxyanilino}quinoline N,N-Diisopropylamine (0.043 g) was added to a stirred mixture of 3-cyano-4-(4-iodo-2,3-methylenedioxyanilino)-6,7-dimethoxyquinoline (0.2 g), 4-(2-propynyl)-1,1-dioxotetrahydro-4H-thiazine (0.145 g), bis(triphenylphosphine)palladium(II) dichloride (0.071 g), cuprous iodide (0.024 g) and ethyl acetate (10 ml) that had been cooled to −20° C. The resultant mixture was allowed to warm to ambient temperature and was stirred for 16 hours. The reaction mixture was partitioned between ethyl acetate and a saturated aqueous sodium bicarbonate solution. The organic layer was washed with water and with a saturated brine solution, dried over magnesium sulphate and evaporated. The residue was triturated under a mixture of acetonitrile and water. The resultant solid was isolated and dried. There was thus obtained the title compound as a solid (0.05 g); NMR Spectrum: (DMSOd$_6$) 2.97–3.04 (m, 4H), 3.12–3.18 (m, 4H), 3.72 (s, 2H), 3.83 (s, 3), 3.85 (s, 3H), 6.04 (s, 2H), 6.82 (d, 1H), 6.95 (d, 1H), 7.31 (s, 1H), 7.74 (s, 1H), 8.48 (s, 1H), 9.6 (s, 1H); Mass Spectrum: M+H$^+$ 521.

EXAMPLE 5

3-cyano-6,7-dimethoxy-4-[2,3-methylenedioxy-4(3-morpholinoprop-1-ynyl)anilino]quinoline dihydrochloride salt Using an analogous procedure to that described in Example 4,3-cyano-4(4-iodo-2,3-methylenedioxyanilino)-6,7-dimethoxyquinoline was reacted with 4-(2-propynyl)morpholine. The reaction mixture was partitioned between ethyl acetate and a saturated aqueous sodium bicarbonate solution. The organic layer was washed with water and with a saturated brine solution, dried over magnesium sulphate and evaporated. The residue was purified by column chromatography on silica using increasingly polar mixtures of methylene chloride and methanol as eluent. The material so obtained was dissolved in the minimum quantity of methylene chloride. The solution was diluted with diethyl ether and a solution of hydrogen chloride in diethyl ether (1M) was added. The resultant solid was isolated, washed with diethyl ether and dried. There was thus obtained the title compound as a solid (0.065 g); NMR Spectrum: (DMSOd$_6$ and CD$_3$CO$_2$D) 3.24–3.29 (m, 4H), 3.9–3.95 (m, 4H), 4.0 (s, 3H), 4.01 (s, 3H), 4.28 (s, 2H), 6.1 (s, 2H); 6.95 (d, 1H), 7.05 (d, 1H), 7.49 (s, 1H), 7.5–7.65 (m, 1H), 8.06 (s, 1H), 8.67 (s, 1H); Mass Spectrum: M−H$^-$ 471.

EXAMPLE 6

3-cyano-6,7-dimethoxy-4-[2,3-methylenedioxy-4-(3-piperazin-1-ylprop-1-ynyl)anilino]quinoline dihydrochloride salt Using an analogous procedure to that described in Example 1,3-cyano-4-(4-iodo-2,3-methylenedioxyanilino)-6,7-dimethoxyquinoline was reacted with 1-(2-propynyl)piperazine (*J. Med. Chem.*, 1993, 3, 610–616). The reaction mixture was partitioned between methylene chloride and a 2N aqueous hydrochloric acid solution. The organic layer was dried over magnesium sulphate and evaporated and the residue was purified by column chromatography on silica using increasingly polar mixtures of methylene chloride and a saturated methanolic ammonia solution as eluent. The material so obtained was dissolved in the minimum quantity of methylene chloride. The solution was diluted with diethyl ether and a solution of hydrogen chloride in diethyl ether (1M) was added. The resultant solid was isolated, washed with diethyl ether and dried. There was thus obtained the title compound; NMR Spectrum: (DMSOd$_6$ and CD$_3$CO$_2$D) 3.28–3.44 (m, 8H), 3.99 (s, 3H), 4.0 (s, 3H), 4.27 (br s, 2H), 6.15 (s, 2H), 7.04 (d, 1H), 7.14 (d, 1H), 7.5 (s, 1H), 8.24 (s, 1H), 9.05 (s, 1H); Mass Spectrum: M−H$^-$ 470.

EXAMPLE 7

4-[4-(5-chloropent-1-ynyl)-2,3-methylenedioxyanilino]-3-cyano-6,7-dimethoxyquinoline Using an analogous procedure to that described in Example 4,3-cyano-4-(4-iodo-2,3-methylenedioxyanilino)-6,7-dimethoxyquinoline was reacted with 5-chloropent-1-yne. The reaction mixture was partitioned between ethyl acetate and a saturated aqueous sodium bicarbonate solution. The organic layer was washed with water and with a saturated brine solution, dried over magnesium sulphate and evaporated. The residue was purified by column chromatography on silica using increasingly polar mixtures of methylene chloride and ethyl acetate as eluent. There was thus obtained the title compound as a gum in 69% yield; Mass Spectrum: M+H$^+$ 450.

EXAMPLE 8

3-cyano-6,7-dimethoxy-4-[2,3-methylenedioxy-4-(5-morpholinopent-1-ynyl)anilino]quinoline dihydrochloride salt Morpholine (5 ml) was added to a mixture of 4-[4-(5-chloropent-1-ynyl)-2,3-methylenedioxyalnilino]-3-cyano-6,7-dimethoxyquinoline (0.11 g) and sodium iodide (0.073 g) and the reaction mixture was stirred at ambient temperature for 16 hours. The resultant mixture was evaporated and the residue partitioned between methylene chloride and water. The organic phase was washed with water and with a saturated brine solution, dried over magnesium sulphate and evaporated. The residue was purified by column chromatography on silica using increasingly polar mixtures of methylene chloride and a saturated methanolic ammonia solution as eluent. The material so obtained was dissolved in the minimum quantity of methylene chloride. The solution was diluted with diethyl ether and a solution of hydrogen chloride in diethyl ether (1M) was added. The resultant solid was isolated, washed with diethyl ether and dried. There was thus obtained the title compound as a solid (0.105 g); NMR Spectrum: (DMSOd$_6$ and CD$_3$CO$_2$D) 1.98–2.04 (m, 2H), 2.56–2.65 (m, 2H), 3.04–3.16 (m, 2H), 3.17–3.26 (m, 2H), 3.39–3.51 (m, 2H), 3.69–4.02 (m, 10H), 6.06 (s, 2H), 6.9 (d, 1H), 6.98 (d, 1H), 7.37 (s, 1H), 7.95 (s, 1H), 8.75 (s, 1H); Mass Spectrum: M+H$^+$ 501.

EXAMPLE 9

Using an analogous procedure to that described in Example 3, the appropriate 4-chloro-3-cyanoquinoline was reacted with the appropriate 2,3-methylenedioxyaniline to give the compounds described in Table I. Unless otherwise stated, each compound described in Table I was obtained as a dihydrochloride salt.

TABLE I

| Compound No. & Note | R$^1$ | (R$^3$)$_n$ |
|---|---|---|
| [1] | 3-(4-methylpiperazin-1-yl)propoxy | 4-(3-methoxyprop-1-ynyl) |
| [2] | 3-morpholinopropoxy | 4-(3-methoxyprop-1-ynyl) |
| [3] | 3-morpholinopropoxy | 6-chloro-4-(3-methoxyprop-1-ynyl) |
| [4] | 3-(1,1-dioxotetrahydro-4H-thiazin-4-yl)propoxy | 4-(3-methoxyprop-1-ynyl) |
| [5] | 2-fluoroethoxy | 4-(3-methoxyprop-1-ynyl) |
| [6] | 3-(3-oxopiperazin-1-yl)propoxy | 4-(3-methoxyprop-1-ynyl) |
| [7] | 3-(3-oxopiperazin-1-yl)propoxy | 6-chloro-4-(3-methoxyprop-1-ynyl) |
| [8] | 2-(2-methoxyethoxy)ethoxy | 4-(3-methoxyprop-1-ynyl) |
| [9] | 3-chloropropoxy | 4-(3-methoxyprop-1-ynyl) |
| [10] | 2-(2-chloroethoxy)ethoxy | 4-(3-methoxyprop-1-ynyl) |

Notes
[1] The product was obtained as a trihydrochloride salt and gave the following characterising data; NMR Spectrum: (DMSOd$_6$) 2.27–2.38(m, 2H), 2.83(s, 3H), 3.23–3.85(m, 10H), 3.34(s, 3H), 4.01(s, 3H), 4.3(t, 2H), 4.35(s, 2H), 6.11(s, 2H), 6.97(d, 1H), 7.01(d, 1H), 7.53(s, 1H), 8.21(s, 1H), 8.94(s, 1H); Mass Spectrum: M − H$^-$ 542.
The 4-chloro-3-cyano-6-methoxy-7-[3-(4-methylpiperazin-1-yl)propoxy]quinoline used as a starting material was prepared as follows:
A mixture of 3-bromopropanol (20 ml), N-methylpiperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation at about 60–70° C. under about 0.2 mm Hg to give 1-(3-hydroxypropyl)-4-methylpiperazine (17 g); NMR Spectrum: (CDCl$_3$) 1.72(m, 2H), 2.3(s, 3H), 2.2–2.8(m, 8H), 2.6(t, 2H), 3.8(t, 2H), 5.3(br s, 1H). A solution of diisopropyl azodicarboxylate (12.1 ml) in methylene chloride (50 ml) was added dropwise during 30 minutes to a stirred mixture of 4-chloro-3-cyano-7-hydroxy-6-methoxyquinoline (12 g), 1-(3-hydroxypropyl)-4-methylpiperazine (9.7 g), triphenylphosphine (16.1 g) and methylene chloride (200 ml) that had been cooled to 5° C. The resultant mixture was allowed to warm to ambient temperature and was then stirred for 1 hour. Further portions of diisopropyl azodicarboxylate (1.2 ml) and triphenylphosphine (1.6 g) were added and the mixture was stirred at ambient temperature for a further 1 hour. The mixture was poured into water and the organic layer was separated, washed with a saturated brine solution, dried over magnesium sulphate and evaporated. The material so obtained, was purified by column chromatography on silica using increasingly polar mixtures of methylene chloride and methanol as eluent. There was thus obtained the required starting material as a solid (14.5 g); NMR Spectrum: (DMSOd$_6$) 1.95(m, 2H), 2.13(s, 3H), 2.24–2.5 (m, 10H), 4.0(s, 3H), 4.25(t, 2H), 7.43(s, 1H), 7.51(s, 1H), 8.95(s, 1H); Mass Spectrum: M + H$^+$ 375 and 377.
[2] 4-Chloro-3-cyano-6-methoxy-7-(3-morpholinopropoxy)quinoline (International Patent Application WO 00/68201, page 52) was used as a starting material. The product gave the following characterising data; NMR Spectrum: (DMSOd$_6$) 2.3–2.38(m, 2H), 3.04–3.14(m, 2H), 3.25–3.31(m, 2H), 3.35(s, 3H), 3.44–3.52(m, 2H), 3.78–3.86(m, 2H), 3.98(d, 2H), 4.01,(s, 3H), 4.3(t, 2H), 4.36(s, 2H), 6.14(s, 2H), 7.0(d, 1H), 7.03(d, 1H), 7.55(s, 1H), 8.21(s, 1H), 8.94(s, 1H); Mass Spectrum: M + H$^+$ 531.

TABLE I-continued

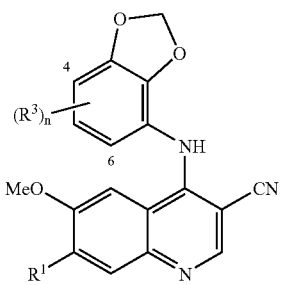

Compound
No. & Note   R¹                                    (R³)ₙ

[3] The product gave the following characterising data; NMR Spectrum: (DMSOd₆) 2.26–2.35(m, 2H), 3.03–3.14(m, 2H), 3.22–3.31(m, 2H), 3.33(s, 3H), 3.44–3.51(m, 2H), 3.81(t, 2H), 3.91–4.0(m, 5H), 4.3.(t, 2H), 4.36(s, 2H), 6.2(d, 2H), 7.22(s, 1H), 7.51(s, 1H), 8.15(s, 1H), 8.86(s, 1H); Mass Spectrum: M −H⁻ 563 and 565.

The 6-chloro-4-(3-methoxyprop-1-ynyl)-2,3-methylenedioxyaniline used as a starting material was prepared as follows:

N,N-Diisopropylamine (0.68 g) was added to a stirred mixture of 6-chloro-4-iodo-2,3-methylenedioxyaniline (1 g), methyl 2-propynyl ether (0.471 g), bis(triphenylphosphine) palladium (II) dichloride (0.472 g), cuprous iodide (0.192 g) and ethyl acetate (20 ml) that had been cooled to −20° C.. The resultant mixture was allowed to warm to ambient temperature and was stirred for 16 hours. The reaction mixture was partitioned between ethyl acetate and a saturated aqueous sodium bicarbonate solution. The organic layer was washed with water and with a saturated brine solution, dried over magnesium sulphate and evaporated. The residue was purified by column chromatography on silica using increasingly polar mixtures of isohexane and methylene chloride as eluent. There was thus obtained 6-chloro-4-(3-methoxyprop-1-ynyl)-2,3-methylenedioxyaniline as a solid (0.2 g); NMR Spectrum: (DMSOd₆) 3.28(s, 3H), 4.26(s, 2H), 5.52(s, 2H), 6.05(s, 2H), 6.93(s, 1H).

[4] The product gave the following characterising data; NMR Spectrum: (DMSOd₆) 2.2–2.27(m, 2H), 3.16–3.2(m, 2H), 3.36(s, 3H), 3.37–3.54(m, 8H), 4.0(s, 3H), 4.3–4.37 (m, 4H), 6.19(s, 2H), 6.8(d, 1H), 7.0(d, 1H), 7.46(s, 1H), 8.0(s, 1H), 8.74(s, 1H); Mass Spectrum: M − H⁻ 577.

The 4-chloro-3-cyano-7-[3-(1,1-dioxotetrahydro-4H-thiazin-4-yl)propoxy]-6-methoxyquinoline used as a starting material was prepared as follows:

A mixture of 3-aminopropan-1-ol (0.65 ml) and divinyl sulphone (1 g) was heated to 110° C. for 45 minutes. The mixture was allowed to cool to ambient temperature and was purified by column chromatography on silica using a 19:1 mixture of methylene chloride and methanol as eluent. There was thus obtained 4-(3-hydroxypropyl)-1,1-dioxotetrahydro-4H-thiazine (0.8 g); NMR Spectrum: (CDCl₃) 1.7–1.8(m, 2H), 2.73(t, 2H), 3.06(br s, 8H), 3.25(s, 1H), 3.78(t, 2H); Mass Spectrum: M + H⁺ 194.

Diethyl azodicarboxylate (1.72 g) was added dropwise to a suspension of 4-chloro-3-cyano-7-hydroxy-6-methoxyquinoline (1 g), 4-(3-hydroxypropyl)-1,1-dioxotetrahydro-4H-thiazine (1.23 g), triphenylphosphine (1.45 g) and methylene chloride (10 ml) and the mixture was stirred at ambient temperature for 16 hours. The resultant mixture was washed with water and with a saturated brine solution. The organic phase was dried over magnesium sulphate and evaporated. The residue was purified by column chromatography on silica using increasingly polar mixtures of methylene chloride, ethyl acetate and a saturated methanolic ammonia solution as eluent. The material so obtained was triturated under diethyl ether. There was thus obtained 4-chloro-3-cyano-7-[3-(1,1-dioxotetrahydro-4H-thiazin-4-yl)propoxy]-6-methoxyquinoline (0.15 g); NMR Spectrum: (DMSOd₆) 1.96 (m, 2H), 2.64 (t, 2H), 2.88–2.93(m, 4H), 3.07–3.12(m, 4H), 4.0(s, 3H), 4.29(t, 2H), 7.44 (s,1H), 7.55(s, 1H), 8.96(s, 1H); Mass Spectrum: M + H⁺ 410.

[5] The product was obtained as a monohydrochloride salt and gave the following characterising data; NMR Spectrum: (DMSOd₆) 3.33(s, 3H), 4.0(s, 3H), 4.35(s, 2H), 4.39–4.43(m, 1H), 4.49–4.53(m, 1H), 4.75–4.8(m, 1H), 4.91–4.96(m, 1H), 6.12(s, 2H), 6.96(d, 1H), 7.01(d, 1H), 7:48(s, 1H), 8.13(s, 1H), 8.94(s, 1H); Mass Spectrum: M + H⁺ 450. The 4-chloro-3-cyano-7-(2-fluoroethoxy)-6-methoxyquinoline used as a starting material was prepared by the reaction of 4-chloro-3-cyano-7-hydroxy-6-methoxyquinoline and 2-fluoroethanol using an analogous procedure to that described in Note [4] immediately above except that the residue was purified by column chromatography on silica using increasingly polar mixtures of methylene chloride and ethyl acetate as eluent. The material so obtained gave the following characterising data; NMR Spectrum: (DMSOd₆) 4.01 (s, 3H), 4.43–4.48(m, 1H), 4.53–4.58(m, 1H), 4.74–4.78(m, 1H), 4.9–4.94(m, 1H), 7.42(s, 1H), 7.56(s, 1H), 8.96(s, 1H); Mass Spectrum: M + H⁺ 281.

TABLE I-continued

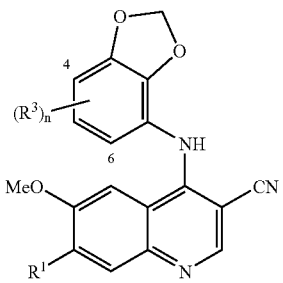

Compound
No. & Note    R¹                              (R³)ₙ

[6] The product was obtained as a free base after chromatographic purification and was not converted into a hydrochloride salt. The product gave the following characterising data; NMR Spectrum: (DMSOd₆ and CD₃CO₂D) 1.96–2.02(m, 2H), 2.6–2.68(m, 4H), 3.03(s, 2H), 3.21(m, 2H), 3.34(s, 3H), 3.94(s, 3H), 4.21(t, 2H), 4.3(s, 2H), 6.01(s, 2H), 6.76(d, 1H), 6.91(d, 1H), 7.34(s, 1H), 7.71(s, 1H), 8.41(s, 1H); Mass Spectrum: M − H⁻ 542.
The 4-chloro-3-cyano-6-methoxy-7-[3-(3-oxopiperazin-1-yl)propoxy]quinoline used as a starting material was prepared by the reaction of 4-chloro-3-cyano-7-hydroxy-6-methoxyquinoline and 4-(3-hydroxypropyl)piperazin-2-one (Tet. Letters, 1994, 35, 9545) using an analogous procedure to that described in Note [4] immediately above. The material so obtained gave the following characterising data; NMR Spectrum: (DMSOd₆) 1.92–2.03 (m, 2H), 2.49–2.59(m, 4H), 2.94(s, 2H), 3.1–3.17(m, 2H), 4.0(s, 3H), 4.27(t, 2H), 7.42(s, 1H), 7.51(s, 1H), 7.69(s, 1H), 8.95(s, 1H); Mass Spectrum: M + H⁺ 375.
[7] The product gave the following characterising data; NMR Spectrum: (DMSOd₆) 2.29–2.36(m, 2H), 3.21–3.41(m, 5H), 3.55–3.9(m, 4H), 3.99(s, 3H), 4.28–4.32(m, 2H), 4.35(s, 2H), 5.99(s, 1H), 6.01(s, 1H), 6.01(s, 2H), 7.21(s, 1H), 7.48(s, 1H), 8.11(s, 1H), 8.81(s, 1H); Mass Spectrum: M + H⁺ 578 and 580.
[8] The product was obtained as a monohydrochloride salt and gave the following characterising data; NMR Spectrum: (DMSOd₆ and CD₃CO₂D) 3.26(s, 3H), 3.36(s, 3H), 3.49 (t, 2H), 3.54(t, 2H), 3.86(t, 2H), 4.0(s, 3H), 4.32–4.36(m, 4H), 6.09(s, 2H), 6.91(d, 1H), 7.0(d, 1H), 7.48(s, 1H), 8.01(s, 1H), 8.75(s, 1H); Mass Spectrum: M + H⁺ 506.
The 4-chloro-3-cyano-6-methoxy-7-[2-(2-methoxyethoxy)ethoxy]quinoline used as a starting material was prepared by the reaction of 4-chloro-3-cyano-7-hyroxy-6-methoxyquinoline and 2-(2-methoxyethoxy)ethanol using an analogous procedure to that described in Note [4] immediately above except that the residue was purified by column chromatography on silica using increasingly polar mixtures of methylene chloride and ethyl acetate as eluent. The material so obtained gave the following characterising data; NMR Spectrum: (DMSOd₆) 3.23(s, 3H), 3.46(s, 2H), 3.61(m, 2H), 3.82(m, 2H), 4.0(s, 3H), 4.34(t, 2H), 7.42(s, 1H), 7.55(s, 1H), 8.95(s, 1H).
[9] The product was obtained as a free base after chromatographic purification and was not converted into a hydrochloride salt. The product gave the following characterising data; NMR Spectrum: (DMSOd₆) 2.25(m, 2H), 3.32(s, 3H), 3.8(t, 2H), 3.92(s, 3H), 4.27 (t, 2H), 4.34(s, 2H), 6.05(s, 2H), 6.82(d, 1H), 6.96(d, 1H), 7.35(s, 1H), 7.74(s, 1H), 8.47 (s, 1H), 9.60(s, 1H); Mass Spectrum: M + H⁺ 480.
The 4-chloro-7-(3-chloropropoxy)-3-cyano-6-methoxyquinoline used as a starting material was prepared as follows:
A mixture of 4-chloro-3-cyano-7-hydroxy-6-methoxyquinoline (0.2 g), potassium tert-butoxide (0.1 g) and DMF(8 ml) was stirred at ambient temperature for 15 minutes. 1-Bromo-3-choropropane (0.134 g) was added and the reaction mixture was stirred at ambient temperature for 16 hours. The resultant mixture was evaporated and the residue was partitioned between methylene chloride and an aqueous sodium bicarbonate solution. The organic layer was dried using magnesium sulphate and evaporated. The residue was purified by column chromatography on silica using increasingly polar mixtures of ethyl acetate and hexane. There was thus obtained the required starting material (0.131 g); NMR Spectrum: (DMSOd₆) 2.3(m, 2H), 3.8(m, 2H), 4.0(s, 3H), 4.35(m, 2H), 7.42(s, 1H), 7.68(s, 1H), 8.95(s, 1H); Mass Spectrum: M + H⁺ 311.
[10] The product was obtained as a free base after chromatographic purification and was not converted into a hydrochloride salt. The product gave the following characterising data; NMR Spectrum: (DMSOd₆) 3.32(s, 3H), 3.72–3.78(m, 4H), 3.85–3.89(m, 2H), 3.91 (s, 3H), 4.28(t, 2H), 4.34(s, 2H), 6.05(s, 2H), 6.82(d, 1H), 6.95(d, 1H), 7.35(s, 1H), 7.74 (s, 1H), 8.47(s, 1H), 9.60(s, 1H); Mass Spectrum: M + H⁺ 510.
The 4-chloro-7-[2-(2-chloroethoxy)ethoxy]-3-cyano-6-methoxyquinoline used as a starting material was prepared by the reaction of 4-chloro-3-cyano-7-hydroxy-6-methoxyquinoline and 2-(2-chloroethoxy)ethanol using an analogous procedure to that described in Note [4] immediately above except that the residue was purified by column chromatography on silica using increasingly polar mixtures of methylene chloride and ethyl acetate as eluent. The material so obtained gave the following characterising data; NMR Spectrum: (DMSOd₆) 3.72–3.8(m, 4H), 3.88–3.93(m, 2H), 4.0(s, 3H), 4.33–4.39(m, 2H), 7.4(s, 1H), 7.55 (s, 1H), 8.94(s, 1H); Mass Spectrum: M + H⁺ 341.

EXAMPLE 10

3-cyano-7-{3-[4-(2-fluoroethyl)piperazin-1-yl]propoxy}-6-methoxy-4-[4-(3-methoxyprop-1-ynyl)-2,3-methylenedioxyanilino]quinoline dihydrochloride salt A mixture of 7-(3-chloropropoxy)-3-cyano-6-methoxy-4-[4-(3-methoxyprop-1-ynyl)-2,3-methylenedioxyanilino]quinoline (0.14 g), 1-(2-fluoroethyl)piperazine trifluoroacetic acid salt (0.158 g), diisopropylethylamine (0.189 g), sodium iodide (0.02 g) and 2-methoxyethanol (20 ml) was stirred and heated to 100° C. for 30 hours. The cooled mixture was evaporated and the resultant residue was partitioned between ethyl acetate and water. The organic layer was dried over magnesium sulphate and evaporated and the residue was purified by column chromatography on silica using increasingly polar mixtures of methylene chloride and methanol as eluent. The material so obtained was dissolved in the minimum quantity of methylene chloride. The solution was diluted with diethyl ether and a solution of hydrogen chloride in diethyl ether (1M) was added. The resultant solid was isolated, washed with diethyl ether and dried. There was thus obtained the title compound (0.045 g); NMR Spectrum: (DMSOd$_6$ and CF$_3$CO$_2$D at 100° C.) 2.22–2.31 (m, 2H), 2.98–3.1 (m, 6H), 3.1.6–3.21 (m, 2H), 3.25–3.31 (m, 4H), 3.36 (s, 3H), 3.99 (s, 3H), 4.3–4.34 (m, 4H), 4.6 (t, 1H), 4.72 (t, 1H), 6.08 (s, 2H), 6.9 (d, 1H), 6.98 (d, 1H), 7.49 (s, 1H), 7.96 (s, 1H), 8.69 (s, 1H); Mass Spectrum: M+H$^+$ 576.

The 1-(2-fluoroethyl)piperazine trifluoroacetic acid used as a starting material was prepared as follows:

A mixture of 1-(tert-butoxycarbonyl)piperazine (5 g), 1-bromo-2-fluoroethane (5.11 g), potassium carbonate (9.26 g) and acetonitrile (60 ml) was stirred and heated to 60° C. for 4 hours. The reaction mixture was cooled to ambient temperature and filtered and the filtrate was evaporated. The residue was purified by column chomatography on silica using increasingly polar mixtures of isohexane and ethyl acetate as eluent. There was thus obtained 4-(tert-butoxycarbonyl)-1-(2-fluoroethyl)piperazine as a solid (3.7 g); NMR Spectrum: (DMSOd$_6$ and CD$_3$CO$_2$D) 1.37 (s, 9H), 2.34–2.4 (m, 4H), 2.56 (t, 1H), 2.67 (t, 1H), 3.25–3.34 (m, 4H), 4.42 (t, 1H), 4.58 (t, 1H).

Trifluoroacetic acid (20 ml) was added to a mixture of 4-(tert-butoxycarbonyl)-1-(2-fluoroethyl)piperazine (3.7 g), triethylsilane (8 ml) and methylene chloride (100 ml) and the resultant mixture was stirred at ambient temperature for 1.5 hours. The mixture was evaporated and the residue was triturated under diethyl ether. The solid so obtained was isolated, washed with diethyl ether and dried. There was thus obtained 1-(2-fluoroethyl)piperazine trifluoroacetic acid salt as a solid (6.0 g); NMR Spectrum: DMSOd$_6$ and CD$_3$CO$_2$D) 3.0–3.31 (m, 10H), 4.59 (m, 1H), 4.75 (m, 1H).

EXAMPLE 11

7-[3-(4-acetylpiperazin-1-yl)propoxy]-3-cyano-6-methoxy-4-[4-(3-methoxyprop-1-ynyl)-2,3-methylenedioxyanilino]quinoline dihydrochloride salt Using an analogous procedure to that described in Example 10, 7-(3-chloropropoxy)-3-cyano-6-methoxy-4-[4-(3-methoxyprop-1-ynyl)-2,3-methylenedioxyanilino]quinoline was reacted with 1-acetylpiperazine to give the title compound in 58% yield; NMR Spectrum: (DMSOd$_6$ and CF$_3$CO$_2$D at 100° C.) 2.04 (s, 3H), 2.3–2.37 (m, 2H), 3.27–3.37 (m, 9H), 3.74–3.84 (m, 4H), 3.96 (s, 3H), 4.3–4.36 (m, 4H), 6.04 (s, 2H), 6.89 (d, 1H), 6.96 (d, 1H), 7.51 (s, 1H), 7.96 (s, 1H), 8.66 (s, 1H); Mass Spectrum: M+H$^+$ 572.

EXAMPLE 12

3-cyano-6-methoxy-4-[4-(3-methoxyprop-1-ynyl)-2,3-methylenedioxyanilino]-7-[2-(2-pyrrolidin-1-ylethoxy)ethoxy]quinoline dihydrochloride salt Pyrrolidine (10 ml) was added to a mixture of 7-[2-(2-chloroethoxy)ethoxy]-3-cyano-6-methoxy-4-[4-(3-methoxyprop-1-ynyl)-2,3-methylenedioxyanilino]quinoline (0.225 g) and sodium iodide (0.133 g) and the reaction mixture was stirred at ambient temperature for 24 hours. The reaction mixture was evaporated and the residue was triturated under methylene chloride. The resultant solid was washed with water and dried. The material so obtained was dissolved in the minimum quantity of ethyl acetate and a solution of hydrogen chloride in diethyl ether (1M) was added. The resultant solid was isolated, washed with diethyl ether and dried. There was thus obtained the title compound as a solid (0.145 g); NMR Spectrum: (DMSOd$_6$ and CD$_3$CO$_2$D at 100° C.) 1.84–1.89 (m, 4H), 3.29–3.39 (m, 9H), 3.88 (m, 2H), 3.94 (m, 2H), 3.96 (s, 3H), 4.3 (s, 2H), 4.36 (m, 2H), 6.04 (s, 2H), 6.84 (d, 1H), 6.94 (d, 1H), 7.46 (s, 1H), 7.87 (s, 1H), 8.56 (s, 1H); Mass Spectrum: M+H$^+$ 545.

EXAMPLE 13

3-[4-(3-cyano-6,7-dimethoxyquinolin-4-ylamino)-2,3-methylenedioxyphenyl]acrylonitrile A mixture of 3-cyano-4-(4-iodo-2,3-methylenedioxyanilino)-6,7-dimethoxyquinoline (0.2 g), acrylonitrile (0.2 ml), triethylamine (0.2 ml), palladium(II) acetate (0.01 g) and DMF (2 ml) was stirred and heated to 115° C. for 3 hours. The reaction mixture was evaporated and the residue was purified by column chromatography on silica using increasingly polar mixtures of hexane and ethyl acetate as eluent. The material so obtained was triturated under diethyl ether. There was thus obtained the title compound, in the form of a 4:1 mixture of trans and cis isomers and as a yellow solid (0.095 g); NMR Spectrum: (DMSOd$_6$, data relating to the major trans isomer) 3.91 (s, 3H), 3.93 (s, 3H), 6.12 (s, 2H), 6.26 (d, 1H), 6.88 (d, 1H), 7.14 (d, 1H), 7.35 (s, 1H), 7.56 (d, 1H), 7.7 (s, 1H), 8.51 (s, 1H), 9.7 (s, 1H); Mass Spectrum: M+H$^+$ 401.

EXAMPLE 14

Using an analogous procedure to that described in Example 13, the appropriate 4-(4-iodo-2,3-methylenedioxyanilino)-3-cyano-6,7-(dimethoxyquinoline was reacted with the appropriate olefin to give the compounds described in Table II.

TABLE II

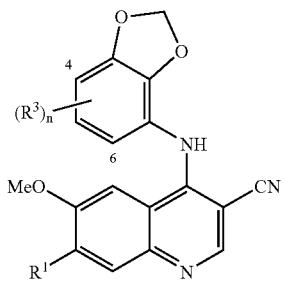

| Compound No. & Note | R¹ | (R³)ₙ |
| --- | --- | --- |
| [1] | methoxy | 6-chloro-4-(2-cyanovinyl) |
| [2] | methoxy | 4-(2-methoxycarbonylvinyl) |
| [3] | methoxy | 6-chloro-4-(2-methoxycarbonylvinyl) |
| [4] | methoxy | 4-(2-propionylvinyl) |

[1] The required olefin was acrylonitrile. The product was obtained as the trans isomer and gave the following characterising data; NMR Spectrum: (DMSOd$_6$) 3.94(s, 3H), 3.98(s, 3H), 6.17(s, 2H), 6.32(d, 1H), 7.33(s, 1H), 7.36(s, 1H), 7.49(d, 1H), 7.84(s, 1H), 8.39(s, 1H), 9.6(br s, 1H); Mass Spectrum: M + H⁺ 435 and 437.

[2] The required olefin was methyl acrylate. The product was obtained as the trans isomer and gave the following characterising data; NMR Spectrum: (DMSOd$_6$) 3.72(s, 3H), 3.91(s, 3H), 3.93(s, 3H), 6.12(s, 2H), 6.29 (d, 1H), 6.88(d, 1H), 7.22(d, 1H), 7.35(s, 1H), 7.59(d, 1H), 7.74(s, 1H), 8.51(s, 1H), 9.68(s, 1H); Mass Spectrum: M + H⁺ 434.

[3] The required olefin was methyl acrylate. The reaction solvent was a 6:1 mixture of acetonitrile and DMF and the reaction mixture was heated to 80° C. for 5 hours. The product was obtained as the trans isomer and gave the following characterising data; NMR Spectrum: (DMSOd$_6$) 3.74(s, 3H), 3.95(s, 6H), 6.22(d, 2H), 6.7(d, 1H), 7.33(s, 1H), 7.53(s, 1H), 7.59(d, 1H), 7.86(s, 1H), 8.44(s, 1H), 9.45(s, 1H); Mass Spectrum: M + H⁺ 468 and 470.

[4] The required olefin was ethyl vinyl ketone. The product was obtained as the trans isomer and gave the following characterising data; NMR Spectrum: (DMSOd$_6$) 1.03(t, 3H), 2.70(q, 2H), 3.91(s, 3H), 3.93(s, 3H), 6.12(s, 2H), 6.83–6.93(m, 2H), 7.22(d, 1H), 7.35(s, 1H), 7.52(d, 1H), 7.74 (s, 1H), 8.51(s, 1H), 9.65(s, 1H); Mass Spectrum: M + H⁺ 432.

EXAMPLE 15

(2E)-3-[4-(3-cyano-6,7-dimethoxyquinolin-4-ylamino)-2,3-methylenedioxyphenyl]acrylic acid A mixture of methyl (2E)-3-[4-(3-cyano-6,7-dimethoxyquinolin-4-ylamino)-2,3-methylenedioxyphenyl]acrylate (0.75 g), a 1N aqueous sodium hydroxide solution (12 ml) and methanol (45 ml) was stirred and warmed to 40° C. for 12 hours. The reaction mixture was evaporated. Water was added and the mixture was acidified by the addition of 2N aqueous hydrochloric acid solution. The resultant precipitate was isolated and dried. There was thus obtained the title compound as a solid (0.703 g); NMR Spectrum: (DMSOd$_6$) 3.98 (s, 6H), 6.19 (s, 2H), 6.59 (d, 1H), 7.02 (d, 1H), 7.28 (d, 1H), 7.48 (s, 1H), 7.55 (d, 1H), 8.09 (s, 1H), 8.95 (s, 1H); Mass Spectrum: M+H⁺ 420.

EXAMPLE 16

N-{(2E)-3-[4-(3-cyano-6,7-dimethoxyquinolin-4-ylamino)-2,3-methylene dioxyphenyl]acryloyl}morpholine 1-(3-Dimethylaminopropyl)-3-ethylcarbodiimide hydrochloride (0.196 g) was added to a mixture of (2E)-3-[4-(3-cyano-6,7-dimethoxyquinolin-4-ylamino)-2,3-methylenedioxyphenyl]acrylic acid (0.35 g), morpholine (0.36 ml), N-methylmorpholine (0.112 ml), 1-hydroxybenzotriazole (0.112 ml), DMF (2 ml) and methylene chloride (10 ml) and the reaction mixture was stirred at ambient temperature for 12 hours. The resultant mixture was partitioned between methylene chloride and water. The organic layer was dried over magnesium sulphate and evaporated and the residue was purified by column chromatography on silica using increasingly polar mixtures of methylene chloride and methanol as eluent. The material so obtained was triturated under diethyl ether. There was thus obtained the title compound as a solid (0.031 g); NMR Spectrum: (DMSOd$_6$) 3.66 (s, 8H), 3.96 (s, 6H), 6.09 (s, 2H), 6.87 (d, 1H), 7.19 (d, 1H), 7.28 (d, 1H), 7.34 (s, 1H), 7.49 (d, 1H), 7.77 (s, 1H), 8.48 (s, 1H), 9.63 (s, 1H); Mass Spectrum: M+H⁺ 489.

EXAMPLE 17

(2E)-3-[4-(3-cyano-6,7-dimethoxyquinolin-4-ylamino)-2,3-methylenedioxyphenyl]-N-(2-methoxyethyl)acrylamide Using an analogous procedure to that described in Example 16, (2E)-3-[4-(3-cyano-6,7-dimethoxyquinolin-4-ylamino)-2,3-methylenedioxyphenyl]acrylic acid was reacted with 2-methoxyethylamine to give the title compound in 64% yield; NMR Spectrum: (DMSOd$_6$) 3.22–3.43 (m, 7H), 3.95 (s, 3H), 3.96 (s, 3H), 6.1 (s, 2H), 6.74 (d, 1H), 6.87 (d, 1H), 7.07 (d, 1H), 7.32 (s, 2H), 7.73 (s, 1H), 8.22 (t, 1H), 8.48 (s, 1H), 9.62 (s, 1H); Mass Spectrum: M+H⁺ 477.

EXAMPLE 18

(2E)-3-[4-(3-cyano-6,7-dimethoxyquinolin-4-ylamino)-2,3-methylenedioxyphenyl]-N-(2-methoxyethyl)-N-methylacrylamide Using an analogous procedure to that described in Example 16, (2E)-3-[4-(3-cyano-6,7-dimethoxyquinolin-4-ylamino)-2,3-methylenedioxyphenyl]acrylic acid was reacted with N-(2-methoxyethyl)-N-methylamine to give the title compound in 47% yield; NMR Spectrum: (DMSOd$_6$) 2.94 (s, 1.5H), 3.08 (s, 1.5H), 3.17 (s, 3H), 3.43–3.65 (m, 4H), 3.95 (s, 3H), 3.96 (s, 3H), 6.1 (s, 2H), 6.84 (d, 1H), 7.16 (d, 1H), 7.25 (d, 1H), 7.33 (s, 1H), 7.43 (d, 1H), 7.76 (s, 1H), 8.48 (s, 1H), 9.62 (s, 1H); Mass Spectrum: M+H⁺ 491.

EXAMPLE 19

3-cyano-6,7-dimethoxy-4-[5-(3-methoxyprop-1-ynyl)-2,3-methylenedioxyanilino]quinoline A mixture of 4-(5-bromo-2,3-methylenedioxyanilino)-3-cyano-6,7-dimethoxyquinoline (0.15 g), methyl 2-propynyl ether (0.049 g), tetrakis(triphenylphosphine)palladium(0) (0.02 g) and pyrrolidine (2 ml) was stirred and heated to 80° C. for 8 hours. The resultant mixture was cooled to ambient temperature, poured into a dilute aqueous ammonium chloride solution and extracted with ethyl acetate. The organic phase was washed with water and with a saturated brine solution, dried over magnesium sulphate and evaporated. The residue was purified by column chromatography on silica using increasingly polar mixtures of methylene chloride and methanol as eluent. There was thus obtained the title compound as a solid (0.032 g); NMR Spectrum: (CDCl$_3$) 3.4 (s, 3H), 3.77 (s, 3H), 4.04 (s, 3H), 4.24 (s, 2H), 5.97 (s, 2H), 6.65 (br s, 1H), 6.73 (d, 1H), 6.78 (d, 1H), 6.99 (s, 1H), 7.38 (s, 1H), 8.63 (s, 1H); Mass Spectrum: M+H$^+$ 418.

The 4-(5-bromo-2,3-methylenedioxyanilino)-3-cyano-6,7-dimethoxyquinoline used as a starting material was prepared as follows:

A mixture of 6-bromo-1,3-benzodioxole-4-carboxylic acid [*Khimn. Geterotsikl. Soedin* 1979, 9, 1183–8 (Chemical Abstracts 22, 94280); 0.92 g], diphenylphosphoryl azide (1.08 g), tert-butanol (3 ml), triethylamine (0.34 g) and toluene (15 ml) were stirred and heated at 100° C. for 4 hours. The resultant mixture was evaporated and the residue was partitioned between methyl tert-butyl ether and a 5% aqueous citric acid solution. The organic phase was washed with water and a saturated aqueous sodium bicarbonate solution, dried over magnesium sulphate and evaporated. The residual oil was purified by column chromatography on silica using a 5:1 mixture of isohexane and ethyl acetate as eluent. There was thus obtained tert-butyl N-(6-bromo-1,3-benzodioxol-4-yl)carbamate (0.6 g); NMR Spectrum: (CDCl$_3$) 1.52 (s, 9H), 5.95 (s, 2H), 6.39 (br s, 1H), 6.7 (d, 1H), 7.73 (br s, 1H).

A mixture of the material so obtained, trifluoroacetic acid (3 ml) and methylene chloride (8 ml) was stirred at ambient temperature for 1 hour. The solvent was evaporated and the residue was partitioned between methyl tert-butyl ether and a saturated aqueous sodium bicarbonate solution. The organic phase was washed with a saturated brine solution, dried over magnesium sulphate and evaporated. The residue was purified by column chromatography on silica using a 4:1 mixture of isohexane and ethyl acetate as eluent. There was thus obtained 5-bromo-2,3-methylenedioxyailine (0.318 g) as a colourless solid; NMR Spectrum: (CDCl$_3$) 3.6 (br s, 2H), 5.92 (s, 2H), 6.27 (m, 2H).

Using an analogous procedure to that described in Example 3,4-chloro-3-cyano-6,7-dimethoxyquinoline (0.65 g) was reacted with 5-bromo-2,3-methylenedioxyaniline (0.587 g). The free base obtained after chromatographic purification was not converted into the dihydrochloride salt. There was thus obtained 4-(5-bromo-2,3-methylenedioxyanilino)-3-cyano-6,7-dimethoxyquinoline as a solid (1.16 g); NMR Spectrum: (CDCl$_3$) 3.83 (s, 3H), 4.05 (s, 3H), 5.98 (s, 2H), 6.76 (d, 1H), 6.84 (d, 1H), 6.9 (br s, 1H), 7.06 (s, 1H), 7.39 (s, 1H), 8.64 (s, 1H); Mass Spectrum: M+H$^+$ 428 and 430.

EXAMPLE 20

3-cyano-7-methoxy-5-[(1-methylpiperidin-4-yl)oxy] 4-[4-(3-methoxyprop-1-ynyl)-2,3-methylenedioxyanilino]quinoline dihydrochloride salt A mixture of 4-chloro-3-cyano-7-methoxy-5-[(1-methylpiperidin-4-yl)oxy]quinoline (165 mg) and 4-(3-methoxyprop-1-ynyl)-2,3-methylendioxyaniline (123 mg) in 1-propanol (10 ml) was treated with a 1.0M solution of hydrogen chloride in diethyl ether (0.5 ml) then stirred and heated at reflux for 2 hours. On cooling a solid precipitated from the reaction mixture. The resulting suspension was basified with aqueous ammonia and evaporated to a gum. This residue was purified by multi-injection preparative RP HPLC [Kromasil C18 5 μm silica column, 100 mm×10 mm; eluted with a mixture of acetonitrile (55%) and 0.1% aqeous ammonia solution (45%)]. After isolation, the major product was converted to its dihydrochloride salt in acetonitrile using two equivalents of a 1.0M solution of hydrogen chloride in diethyl ether. The title compound was thus obtained as a yellow solid (81 mg); NMR Spectrum: (DMSOd$_6$ & CD$_3$COOD, 373K) 2.17 (m, 2H), 2.38 (m, 2H), 2.77 (s, 3H), 3.30 (m, 4H), 3.37 (s, 3H), 3.96 (s, 3H), 4.33 (s, 2H), 5.04 (m, 1H), 6.12 (s, 2H), 6.92 (d, 1H), 6.97 (m, 2H), 7.08 (s, 1H), 8.63 (s, 1H); Mass Spectrum: M+H$^+$ 501.

The 4-(3-methoxyprop-1-ynyl)-2,3-methylendioxyaniline used as a starting material was prepared as described in example 3.

The 4-chloro-3-cyano-7-methoxy-5-[(1-methylpiperidin-4-yl)oxy]quinoline used as a starting material was prepared as follows:

i) Preparation of ethyl (2-E/Z)-2-cyano-3-[(3,5-difluorophenyl)amino]acrylate

A mixture of 3,5-difluoroaniline (32.25 g) and ethyl 2-cyano-3-ethoxyacrylate (42.25 g) dissolved in ethanol (200 ml) was refluxed for 2 hours and then allowed to cool. The product was filtered off and washed with a little ethanol to give the title compound as White needles (58.0 g; 92%); NMR spectrum: (DMSOd$_6$) E/Z or Z/E mixture 64/36, 1.28 (m, 3H), 4.23 (m, 2H), 6.98–7.42 (m, 3H), 8.44 (m, 1H), 10.80 (m, 1H); Mass spectrum: M+H$^+$ 253.

ii) Preparation of 3-cyano-5,7-difluoro-4-hydroxyquinoline

Di(ethylene glycol) dibutyl ether (100 ml) was refluxed at 255° C. under nitrogen in a 250 ml flask. To this was added ethyl (2-E/Z)-2-cyano-3-[(3,5-difluorophenyl)amino]acrylate (12.5 g) in portions over 10 minutes. The mixture was heated for a further 30 minutes and then allowed to cool. The precipitated solid was collected and washed with ethyl acetate. The title compound was thus obtained as a grey/brown solid (4.24 g, 41%); NMR spectrum: (DMSOd$_6$) 7.21 (m, 1H), 7.30 (m, 1H), 8.72 (s, 1H), 12.86 (broad, 1H); Mass spectrum: M+H$^+$ 207.

iii) Preparation of 3-cyano-7-fluoro-4-hydroxy-5-[(1-methylpiperidin-4-yl)oxy]quinoline A mixture of 3-cyano-5,7-difluoro-4-hydroxyquinoline (4.12 g), 1-methylpiperidin-4-ol (2.6 g) and potassium tert-butoxide (6.72 g) in anhydrous tetrahydrofuran (250 ml) was stirred and heated at 60° C. for 2 hours. Acetic acid was added until pH6 was reached and then the solution was evaporated to dryness. The residue was dissolved in a mixture of dichloromethane and methanol (2:1) and the solution added to powdered silica gel (15 g). The suspension was evaporated to dryness and powder was packed into a preload cartridge. This was then chromatographed with an Isco Combiflash system and a Biotage 40M silica cartridge using a gradient elution of 0.6% to 30% ammonia (7.0M in methanol) in dichloromethane. The fractions containing the product were combined and evaporated. This gave the title compound as a white foam (3.55 g, 59%); NMR spectrum: (DMSOd$_6$) 1.77 (m, 2H), 1.92 (m, 2H), 2.30 (s, 3H), 2.43 (m, 2H), 2.81 (m, 2H), 4.55 (m, 1H), 6.81 (m, 2H), 8.40 (s, 1H), Mass spectrum: M+H$^+$ 302.

iv) Preparation of 3-cyano-4-hydroxy-7-methoxy-5-[(1-methylpiperidin-4-yl)oxy]quinoline A mixture of 3-cyano-7-fluoro-4-hydroxy-5-[(1-methylpiperidin-4-yl)oxy]quinoline (600 mg), methanol (0.40 ml) and potassium tert-butoxide (1.0M solution in tetrahydrofuran; 10.0 ml) in anhydrous dimethyl sulphoxide (20 ml) was heated at 70° C. for 16 hours. The solution was cooled and then diluted with water (100 ml). Dilute hydrochloric acid was added until pH6 was reached and the by-product precipitate (3-cyano-4-hydroxy-5,7-dimethoxyquinoline) was filtered off. The filtrate was pumped onto a cation exchange cartridge (Waters Oasis MCX 6.0 g) and washed on with water. The column was flushed successively with water (200 ml), methanol/water (1:1; 200 ml) and methanol (200 ml). The product was eluted off the column with methanol containing triethylamine (1%). The fractions containing the product were combined and evaporated. This gave the title compound as an white solid (460 mg, 73%); NMR spectrum: (DMSOd$_6$) 1.67 (m, 2H), 1.83 (m, 2H), 2.12 (m, 2H), 2.15 (s, 3H), 2.64 (m, 2H), 4.31 (m, 1H), 6.31 (d, 1H), 6.56 (d, 1H), 8.16 (s, 1H); Mass spectrum: M+H$^+$ 314.

v) Preparation of 4-chloro-3-cyano-7-methoxy-5-[(1-methylpiperidin-4-yl)oxy]quinoline A mixture of 3-cyano-4-hydroxy-7-methoxy-5-[(1-methylpiperidin-4-yl)oxy]quinoline (313 mg) and phosphoryl chloride (1.8 ml) in acetonitrile (10 ml) was refluxed and stirred for 20 hours. After cooling, the solution was evaporated to dryness. The flask containing the residue was filled with ice chips and excess concentrated aqueous ammonia (25 ml) was added. This mixture was allowed to warm up while stirring overnight. The product was filtered off and dried under high vacuum overnight. The title compound was obtained as a white solid (225 mg, 68%); NMR spectrum: (DMSOd$_6$) 1.80 (m, 2H), 1.98 (m, 2H), 2.18 (s, 3H), 2.27 (m, 2H), 2.58 (m, 2H), 3.94 (s, 3H), 4.72 (m, 1H), 6.92 (d, 1H), 7.09 (d, 1H), 8.93 (s, 1H); Mass spectrum: M+H$^+$ 332.

EXAMPLE 21

3-cyano-7-(3-morpholin-4-ylpropoxy)-5-(tetrahydro-2H-pyran-4-yloxy)-4-[4-(3-methoxyprop-1-ynyl)-2,3-methylenedioxyanilino]quinoline dihydrochloride salt A mixture of 4-chloro-3-cyano-7-(3-morpholin-4-ylpropoxy)-5-(tetrahydro-2H-pyran-4-yloxy)quinoline (125 mg) and 4-(3-methoxyprop-1-ynyl)-2,3-methylendioxyaniline (179 mg) in 1-propanol (8 ml) was treated with a 11.0M solution of hydrogen chloride in diethyl ether (0.30 ml) then stirred and heated at reflux for 1 hour. The mixture was allowed to cool and neutralised by the addition of tetramethylguanidine (0.10 ml). The resulting solution was evaporated to dryness and the residue was purified by chromatography on a Biotage silica cartridge (20 g) eluting with a gradient of methanol in dichloromethane (1–10%). The fractions containing the product were combined and evaporated. The residue was dissolved in ethanol (8 ml) and treated with 2 equivalents of hydrogen chloride (1.0M in diethyl ether). The title compound was thus obtained as a white solid (130 mg); NMR Spectrum: (DMSOd$_6$, 300K) 1.87 (m, 2H), 2.10 (m, 2H), 2.31 (m, 2H), 3.11 (m, 2H), 3.30 (m, 2H), 3.36 (s, 3H), 3.50 (m, 4H), 3.87 (m, 4H), 3.97 (m, 2H), 4.32 (m, 2H), 4.37 (s, 2H), 5.10 (m, 1H), 6.18 (s, 2H), 1.05 (m, 3H), 7.13 (s, 1H), 8.87 (s, 1H), 10.43 (s, 1H), 11.34 (s, 1H); Mass Spectrum: M+H$^+$ 601.

The 4-(3-methoxyprop-1-ynyl)-2,3-methylendioxyaniline used as a starting material was prepared as described in example 3.

The 4-chloro-3-cyano-7-(3-morpholin-4-ylpropoxy)-5-(tetrahydro-2H-pyran-4-yloxy)quinoline used as a starting material was prepared as follows:

i) 3-cyano-5,7-difluoro-4-hydroxyquinoline was prepared as described in example 20.

ii) Preparation of 3-cyano-7-fluoro-4-hydroxy-5-(tetrahydro-2H-pyran-4-yloxy)quinoline A mixture of 3-cyano-5,7-difluoro-4-hydroxyquinoline (2.06 g), tetrahydro-2H-pyran-4-ol (1.02 g) and potassium tert-butoxide (1.0M solution in tetrahydrofuran; 30.0 ml) in anhydrous tetrahydrofuran (100 ml) was stirred and heated under nitrogen at 60° C. for 1.5 hours. Acetic acid was added until pH6 was reached and then the solution was evaporated to dryness. The residue was dissolved in aqueous sodium hydroxide solution (2.0M) and the resulting solution was filtered through a GF/A glass fibre pad. The filtrate was acidified to pH5 with acetic acid and the resulting oily precipitate allowed to stand 3 days when it had become solid. The solid was collected and washed with water then air-dried. (1.8 g, 62%); NMR spectrum: (DMSOd$_6$) 1.67 (m, 2H), 1.92 (m, 2H), 3.50 (m, 2H), 3.91 (m, 2H), 4.76 (m, 1H), 6.81 (m, 1H), 6.94 (m, 1H), 8.52 (s, 1H); Mass spectrum: M+H$^+$ 289.

iii) Preparation of 3-cyano-4-hydroxy-7-(3-morpholin-4-ylpropoxy)-5-(tetrahydro-2H-pyran-4-yloxy)quinoline A mixture of 3-cyano-7-fluoro-4-hydroxy-5-(tetrahydro-2H-pyran-4-yloxy)quinoline (864 mg), 3-morpholin-4-yl-propan-1-ol (876 mg) and potassium tert-butoxide (1.0M solution in tetrahydrofuran; 9.0 ml) in anhydrous dimethyl sulphoxide (30 ml) was heated at 60° C. for 8 hours. The solution was cooled and then diluted with water (120 ml). Acetic acid was added until pH5 was reached. The solution was pumped onto a cation exchange cartridge (Waters Oasis MCX 6.0 g) and washed on with water. The column was flushed successively with water (200 ml), methanol/water (1:1; 200 ml) and methanol (200 ml). The product was eluted off the column with methanol containing triethylamine (1%). The fractions containing the product were combined and evaporated. The residue was further purified by chromatography on a Redisep silica cartridge (40 g) eluting with a gradient of methanol in dichloromethane (5–20%). This gave the title compound as an white solid (540 mg, 44%); NMR spectrum: (DMSOd$_6$; 373° K) 1.73 (m, 2H), 1.91 (m, 4H), 2.39 (m, 4H), 2.45 (t, 2H), 3.49 (m, 2H), 3.58 (m, 4H), 3.95 (m, 2H), 4.10 (t, 2H), 4.64 (m, 1H), 6.46 (d, 1H), 6.60 (d, 1H), 8.24 (s, 1H); Mass spectrum: M+H$^+$ 414.

iv) Preparation of 4-chloro-3-cyano-7-(3-morpholin-4-ylpropoxy)-5-(tetrahydro-2H-pyran-4-yloxy)quinoline A mixture of 3-cyano-4-hydroxy-7-(3-morpholin-4-ylpropoxy)-5-(tetrahydro-2H-pyran-4-yloxy)quinoline (500 mg) and phosphoryl chloride (2.5 ml) in acetonitrile (1.5 ml) was refluxed and stirred for 4 hours. After cooling, the solution was evaporated to dryness. The flask containing the residue was filled with ice chips and excess concentrated aqueous ammonia (25 ml) was added. This mixture was allowed to warm up while stirring overnight. The product was filtered off and air-dried. The title compound was obtained as a white solid (480 mg, 92%); Mass spectrum: M+H$^+$ 432.

EXAMPLE 22

3-Cyano-7-methoxy-4-[4-(4-methoxybut-1-ynyl)-2,
3-methylenedioxyanilino]-5-[(1-methylpiperidin-4-
yl)oxy]quinoline dihydrochloride salt A mixture of 4-chloro-3-cyano-7-methoxy-5-[(1-methylpiperidin-4-yl)oxy]quinoline (165 mg) and 4-(4-methoxybut-1-ynyl)-2,3-methylendioxyaniline (131 mg) in 1-propanol (10 ml) was treated with a 1.0M solution of hydrogen chloride in diethyl ether (0.5 ml) then stirred and heated at reflux for 2 hours. On cooling a solid precipitated from the reaction mixture. This solid was collected and washed with 1-propanol. Analysis by LC/MS suggested the product was impure. The solid hydrochloride salt and the liquors were combined and basified with a solution of sodium bis(trimethylsilyl)amide (1.0M in THF; 1.0 ml) and the solution allowed to stand overnight. The mixture was evaporated and separated by multi-injection preparative RP HPLC [Kromasil C18 5 µm silica column, 100 mm×10 nm; eluted with a mixture of acetonitrile (55%) and 0.1% aqeous ammonia solution (45%)]. After isolation, the component bases were converted to their dihydrochloride salts in acetonitrile using two equivalents of a 1.0M solution of hydrogen chloride in diethyl ether.

The main component, 3-cyano-7-methoxy-4-[4-(4-methoxybut-1-ynyl)-2,3-methylenedioxyanilino]-5-[(1-methylpiperidin-4-yl)oxy]quinoline dihydrochloride salt, was thus obtained as a yellow solid (51 mg); NMR Spectrum: (DMSOd$_6$ and CD$_3$CO$_2$D, 393K) 2.19 (m, 2H), 2.37 (m, 2H), 2.72 (m, 5H), 3.00 (m, 3H), 3.26 (m, 1H), 3.35 (s, 3H), 3.58 (t, 2H), 3.96 (s, 3H), 5.00 (m, 1H), 6.10 (s, 2H), 6.85 (m, 2H), 6.92 (s, 1H), 7.05 (s, 1H), 8.48 (s, 1H), 9.51 (br, 1H); Mass Spectrum: M+H$^+$ 515.

The second component, 4-[(4-but-3-en-1-ynyl-2,3-methylendioxy)anilino]-3-cyano-7-methoxy-5-[(1-methylpiperidin-4-yl)oxy]quinoline dihydrochloride salt, was thus obtained as a yellow solid (18 mg); NMR Spectrum: (DMSOd$_6$, 393K) 2.18 (m, 2H), 2.35 (m, 2H), 2.70 (s, 3H), 3.09 (m, 4H), 3.95 (s, 3H), 5.00 (m, 1H), 5.62 (d, 1H), 5.73 (d, 1H), 6.11 (m, 3H), 6.90 (m, 3H), 7.07 (s, 1H), 8.51 (s, 1H), 9.55 (br, 1H); Mass Spectrum: M+H$^+$ 483.

The third component, 4-[4-(1-chloro-4-methoxybut-1-enyl)-2,3-methylenedioxyanilino]-3-cyano-7-methoxy-5-[(1-methylpiperidin-4-yl)oxy]quinoline dihydrochloride salt, was thus obtained as a yellow solid (2.1 mg); Mass Spectrum: M+H$^+$ 551. (The stereochemistry of the double bond was not established.)

4-Chloro-3-cyano-7-methoxy-5-[(1-methylpiperidin-4-yl)oxy]quinoline used as a starting material was prepared as described in example 20.

4-(4-methoxybut-1-yn-1-yl)-2,3-methylendioxyaniline used as a starting material was prepared as follows:

A solution of 4-iodo-2,3-methylenedioxyaniline (1.32 g, 5.00 mmol) and 4-methoxybut-1-yne (0.84 g, 10.00 mmol) in ethyl acetate (25 ml) was cooled in ice-methanol, under an atmosphere of nitrogen, then treated with bis(triphenylphosphine) palladium(II) dichloride (350 mg, 10 mol %) followed by copper(I) iodide (95 mg, 10 mol %) and diisopropylamine (1.40 ml, 10.0 mmol). The reaction was stirred for 2 hours in the cooling bath and then allowed to warm to room temperature over 4 hours: The mixture was filtered through Celite and the filtrate was then purified by column chromatography on silica using a gradient of methanol in dichloromethane (0–2%) as eluent to give 4-(4-methoxybut-1-yn-1-yl)-2,3-methylendioxyaniline (524 mg, 82%) as a dark oil; LCMS: M+H$^+$ 220 (82%).

4-Methoxybut-1-yne is described in *Aust. J. Chem.* 1988, 41(2), 251 261.

4-iodo-2,3-methylenedioxyaniline was prepared as described in example 1.

EXAMPLE 23

3-cyano-4-[6-chloro-4-(3-methoxyprop-1-ynyl)-2,3-
methylenedioxyanilino]-7-methoxy-5-[(1-methylpiperidin-4-yl)oxy]quinoline dihydrochloride salt A mixture of 4-chloro-3-cyano-7-methoxy-5-[(1-methylpiperidin-4-yl)oxy]quinoline (203 mg) and 6-chloro-4-(3-methoxyprop-1-ynyl)-2,3-methylendioxyaniline (139 mg) in dry dimethylformamide (6 ml) was stirred at room temperature. Sodium bis(trimethylsilyl)amide (1.0M solution in tetrahydrofuran; 1.35 ml) was added and then the mixture was allowed to warm to room temperature over one hour. The reaction mixture was acidified with acetic acid (2.0 ml) and the solvent was evaporated under high vacuum. The residue was dissolved in a mixture of dichloromethane and methanol (9:1) and the mixture preabsorbed onto silica gel (kieselgel 60; 2.5 g). The solvent was evaporated and the solid packed into a preload cartridge. This was then purified by chromatography on a 40 g silica Redisep cartridge using gradient elution [0.5% to 3% ammonia solution (7.0M in methanol) in dichloromethane]. Fractions containing the required product were combined and evaporated to give the free base (240 mg). This material was dissolved in ethanol (10 ml) and treated with 2 equivalents of 1.0M hydrogen chloride in diethyl ether. The solvents were evaporated and the residue was dissolved in acetonitrile (10 ml). The title compound crystallised on standing overnight as a pale yellow solid (158 mg); NMR Spectrum: (DMSOd$_6$, 373K) 2.21 (m, 2H), 2.41 (m, 2H), 2.76 (s, 3H), 3.15 (m, 2H), 3.47 (s, 3H), 3.49 (m, 2H), 3.97 (s, 3H), 4.36 (s, 2H), 5.04 (m, 1H), 6.16 (s, 2H), 6.97 (m, 1H), 7.07 (s, 1H), 7.13 (s, 1H), 8.56 (s; 1H), 9.73 (br, 1H), 10.75 (br, 1H); Mass Spectrum: M+H$^+$ 535.

4-Chloro-3-cyano-7-methoxy-5-[(1-methylpiperidin-4-yl)oxy]quinoline used as a starting material was prepared as described in example 20.

6-Chloro-4-(3-methoxyprop-1-ynyl)-2,3-methylendioxyaniline used as a starting material was prepared as follows:

Sulphuryl chloride (72.5 ml) was added dropwise during 1.7 hours to a stirred mixture of benzodioxole (100 g), aluminium trichloride (0.43 g) and diphenyl sulphide (0.55 ml). Once the reaction started with the evolution of sulphur dioxide, the reaction mixture was cooled in a water bath to a temperature of approximately 22° C. After completion of the addition, the reaction mixture was stirred at ambient temperature for 45 minutes. The reaction mixture was degassed under vacuum and filtered and the filtrate was distilled at atmospheric pressure using a Vigreux distillation column. There was thus obtained 5-chloro-1,3-benzodioxole; b.p. 185–187° C.; NMR Spectrum: (CDCl$_3$) 6.0 (s, 2H); 6.7 (d, 1H); 6.75–6.9 (m, 2H).

A mixture of diisopropylamine (4.92 ml) and THF (100 ml) was cooled to −78° C. and n-butyllithium (2.5 M in hexane, 14 ml) was added dropwise. The mixture was stirred at −78° C. for 15 minutes. 5-Chloro-1,3-benzodioxole (3.73 ml) was added dropwise and the reaction mixture was stirred at −78° C. for 30 minutes. Dry carbon dioxide gas was bubbled into the reaction mixture for 30 minutes. The resultant reaction mixture was allowed to warm to ambient temperature and was stirred for a further hour. Water was added and the organic solvent was evaporated. The residue was acidified to pH2 by the addition of 2N aqueous hydrochloric acid solution. The resultant solid was isolated and washed in turn with water and diethyl ether. There was thus obtained 5-chloro-1,3-benzodioxole-4-carboxylic acid (5.4 g); NMR Spectrum: (DMSOd$_6$) 6.15 (s, 2H), 7.0 (m, 2H), 13.7 (br s, 1H).

A portion (1 g) of the material so obtained was dissolved in 1,4-dioxane (15 ml) and anhydrous tert-butanol (4 ml), diphenylphosphoryl azide (1.12 ml) and triethylamine (0.73 ml) were added in turn. The resultant mixture was stirred and heated to 100° C. for 4 hours. The mixture was evaporated and the residue was partitioned between ethyl acetate and a 5% aqueous citric acid solution. The organic phase was washed in turn with water, a saturated aqueous sodium bicarbonate solution and brine, dried over magnesium sulphate and evaporated. The residue was purified by column chromatography on silica using a 9:1 mixture of petroleum ether (b.p. 40–60° C.) and ethyl acetate as eluent. There was thus obtained tert-butyl 5-chloro-1,3-benzodioxol-4-ylcarbamate (1.1 g); NMR Spectrum: (DMSOd$_6$) 1.45 (s, 9H), 6.1 (s, 2M), 6.85 (d, 1H), 6.95 (d, 1H), 8.75 (s, 1H).

A mixture of the material so obtained (1.1 g), trifluoroacetic acid (6 ml) and methylene chloride (20 ml) was stirred at ambient temperature for 3 hours. The solvent was evaporated and the residue was partitioned between ethyl acetate and a saturated aqueous sodium bicarbonate solution. The organic phase was washed with brine, dried over magnesium sulphate and evaporated. There was thus obtained 6-chloro-2,3-methylenedioxyaniline (0.642 g); NMR Spectrum: (DMSOd$_6$) 5.15 (s, 2H), 6.0 (s, 2H), 6.25 (d, 1H), 6.75 (d, 1H).

Benzyltrimethylammonium dichloroiodate (6.7 g) was added portionwise over 10 minutes to a stirred mixture of 6-chloro-2,3-methylenedioxyaniline (3 g), calcium carbonate (2.28 g) in methanol (15 ml) and dichloromethane (30 ml). The reaction mixture was stirred at ambient temperature for 1.5 hours. The reaction mixture was diluted with water and extracted with dichloromethane. The organics were washed with water, saturated brine and dried over magnesium sulfate. The residue was purified by column chromatography on silica using a gradient of an 8:1 mixture of dichloromethane/isohexane to dichloromethane as eluent. There was thus obtained 6-chloro-4-iodo-2,3-methylendioxyaniline as a black crystalline solid (4.82 g); NMR Spectrum: (DMSOd$_6$) 6.04 (s, 2H), 7.00 (s, 1H).

Bis(Triphenyl-phosphine)palladium(II) chloride (472 mg), copper iodide (192 mg) and diisopropylamine (680 mg) were added to a stirred solution of 6-chloro-4-iodo-2,3-methylenedioxyaniline (1000 mg) and methyl propargyl ether (471 mg) in ethyl acetate (10 mls) at −20° C. The reaction was allowed to warm to ambient temperature over 16 hours. The reaction mixture was partitioned between ethyl acetate and saturated NaHCO3. The organics were washed with water and saturated brine and dried over magnesium sulfate. The product was purified by column chromatography on silica using a gradient of 80–100% Dichloromethane/isohexane as eluent. 6-chloro-4-(3-methoxyprop-1-ynyl)-2,3-methylendioxyaniline was thus obtained as a tan crystalline solid (200 mg); NMR Spectrum: (DMSOd$_6$) 3.28 (s, 3H), 4.26 (s, 2H), 5.52 (s, 2H), 6.05 (s, 2H), 6.93 (s, 1H).

EXAMPLE 24

3-cyano-6,7-dimethoxy-4-[2,3-methylenedioxy-4-(pyridin-2-ylethynyl)anilino]quinoline dihydrochloride salt Using an analogous procedure to that described in Example 1, 3-cyano-4-(4-iodo-2,3-methylenedioxyanilino)-6,7-dimethoxyquinoline was reacted with 2-ethynylpyridine. The reaction mixture was partitioned between methylene chloride and a 2N aqueous hydrochloric acid solution. This resulted in the precipitation of the product which was filtered, washed with dichloromethane, ethanol and diethyl ether and dried to give the title compound as as a yellow solid (53%); NMR Spectrum: (DMSOd$_6$) 4.00 (s, 3H), 4.02 (s, 3H), 6.19 (s, 2H), 7.07 (d, 1H), 7.19 (d, 1H), 7.43–7.49 (m, 1H), 7.50 (s, 1H), 7.68 (d, 1H), 7.88 (t, 1H), 8.21 (s, 1H), 8.63 (d, 1H), 9.08 (s, 1H); Mass Spectrum: M+H$^+$ 451.05.

The invention claimed is:

1. A quinoline derivative of the Formula I

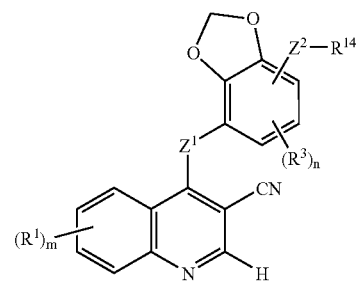

I wherein $Z^1$ is an O, S, SO, SO$_2$, N(R$^2$) or C(R$^2$)$_2$ group, wherein each R$^2$ group, which may be the same or different, is hydrogen or (1–6C)alkyl;

m is 0, 1, 2, 3 or 4;

each R$^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl N,N-di-[(1–6C)alkyl]sulphamoyl, (1–6C)alkanesulphonylamino, N-(1–6C)alkyl-(1–6C)alkanesulphonylamino or from a group of the formula:

wherein X$^1$ is a direct bond or is selected from O, S, SO, SO$_2$, N(R$^4$), CO, CH(OR$^4$), CON(R$^4$), N(R$^4$)CO, SO$_2$N(R$^4$), N(R$^4$)SO$_2$, OC(R$^4$)$_2$, SC(R$^4$)$_2$ and N(R$^4$)C(R$^4$)$_2$, wherein R$^4$ is hydrogen or (1–6C)alkyl, and Q$^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or (R$^1$)$_m$ is (1–3C)alkylenedioxy, and wherein adjacent carbon atoms in any (2–6C)alkylene chain within a R$^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl or, when the inserted group is $N(R^5)$, $R^5$ may also be (2–6C)alkanoyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl, di-[(1–6C)alkyl]amino-(1–6C)alkyl or from a group of the formula:

$Q^2$-$X^2$— wherein $X^2$ is a direct bond or is selected from CO and $N(R^6)CO$, wherein $R^6$ is hydrogen or (1–6C)alkyl, and $Q^2$ is aryl, aryl-(1–6C)alkyl, heteroaryl, heteroaryl-(1–6C)alkyl, heterocyclyl or heterocyclyl-(1–6C)alkyl, and wherein any CH, $CH_2$ or $CH_3$ group within a $R^1$ substituent optionally bears on each said CH, $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N N-di-[(1–6C)alkyl]sulphamoyl, (1–6C)alkanesulphonylamino, N-(1–6C)alkyl-(1–6C)alkanesulphonylamino or from a group of the formula:

—$X^3$-$Q^3$ wherein X3 is a direct bond or is selected from I, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N N-di-[(1–6C)alkyl]sulphamoyl, (1–6C)alkanesulphonylamino, N-(1–6C)alkyl-(1–6C)alkanesulphonylamino or from a group of the formula:

—$X^4$—$R^8$ wherein $X^4$ is a direct bond or is selected from O and $N(R^9)$, wherein R is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl or from a group of the formula:

—$X^5$-$Q^4$ wherein $X^5$ is a direct bond or is selected from O, $N(R^{10})$ and CO, wherein $R^{10}$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^1$ optionally bears 1 or 2 oxo or thioxo substituents;

n is 0, 1,2 or 3;

each $R^3$ group is halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl N,N-di-[(1–6C)alkyl]sulphamoyl, (1–6C)alkanesulphonylamino N-(1–6C)alkyl-(1–6C)alkanesulphonylamino or from a group of the formula:

—$X^6$—$R^{11}$ wherein $X^6$ is a direct bond or is selected from O and $N(R^{12})$, wherein $R^{12}$ is hydrogen or (1–6C)alkyl, and $R^{11}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl;

$Z^2$ is a C≡C or $C(R^{13})$=$C(R^{13})$ group, wherein each $R^{13}$ group, which may be the same or different, is hydrogen or (1–6C)alkyl; and $R^{14}$ is selected from halogeno, cyano, isocyano, formyl, carboxy, carbamoyl, (2–8C)alkenyl, (2–8C)alkynyl, (1–6C)alkoxycarbonyl, N-(1–6C)alkylcarbamoyl, N,N-di-[(1–6C)alkyl]carbamoyl, (2–6C)alkanoyl, N-(1–6C)alkylsulphamoyl, N,N-di-[(1–6C)alkyl]sulphamoyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl or from a group of the formula:

—$X^7$-$Q^5$ wherein $X^7$ a direct bond or is selected from CO, $CH(OR^{15})$, $CON(R^{15})$ or $SO_2N(R^{15})$, wherein $R^{15}$ is hydrogen or (1–6C)alkyl, and $Q^5$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein any CH, $CH_2$ or $CH_3$ group within a $R^{14}$ substituent optionally bears on each said CH, $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-

[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]-sulphamoyl, (1–6C)alkanesulphonylamino, N-(1–6C)alkyl-(1–6C)alkanesulphonylamino or from a group of the formula:

—X$^8$-Q$^6$ wherein X$^8$ is a direct bond or is selected from O, S, SO, SO$_2$, N(R$^{16}$), CO, CH(OR$^{16}$), CON(R$^{16}$), N(R$^{16}$)CO, SO$_2$N(R$^{16}$), N(R$^{16}$)SO$_2$, C(R$^{16}$)$_2$O, C(R$^{16}$)$_2$S and N(R$^{16}$)C(R$^{16}$)$_2$, wherein R$^{16}$ is hydrogen or (1–6C)alkyl, and Q$^6$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on R$^{14}$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino N-(1–6C)alkyl-(2–6C)alkanoylamino, N-(1–6C)alkylsulphamoyl, N,N-di-[(1–6C)alkyl]-sulphamoyl, (1–6C)alkanesulphonylamino, N-(1–6C)alkyl-(1–6C)alkanesulphonylamino or from a group of the formula:

—X$^9$—R$^{17}$ wherein X$^9$ is a direct bond or is selected from O and N(R$^{18}$), wherein R$^{18}$ is hydrogen or (1–6C)alkyl, and R$^{17}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl, or from a group of the formula:

—X$^{10}$-Q$^7$ wherein X$^{10}$ is a direct bond or is selected from O, N(R$^{19}$) and CO, wherein R$^{19}$ is hydrogen or (1–6C)alkyl, and Q$^7$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on R$^{14}$ optionally bears 1 or 2 oxo or thioxo substituents;

or a pharmaceutically-acceptable salt thereof.

2. A quinoline derivative of the Formula I, or a pharmaceutically acceptable salt thereof, according to claim 1 wherein R$^1$, R$^3$, Z$^1$, Z$^2$, m and n have any of the meanings defined in claim 1 and R$^{14}$ is selected from cyano, formyl, carboxy, carbamoyl, methoxycarbonyl, vinyl, ethoxycarbonyl, N-methylcarbamoyl, N-ethylcarbamoyl, N,N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl or from a group of the formula:

—X$^7$-Q$^5$ wherein X$^7$ is a direct bond or CO and Q$^5$ is pyridin-2-yl, 1-pyrrolidinyl, morpholino, 1,1-dioxotetrahydro-4H-1,4-thiazin-4-yl, piperidino, 1-homopiperidinyl, piperazin-1-yl, homopiperazin-1-yl, 1-pyrrolidinylmethyl, morpholinomethyl, piperidinomethyl, 1-homopiperidinylmethyl, 1,1-dioxotetrahydro-4H-1,4-thiazin-4-ylmethyl, piperazin-1-ylmethyl, homopiperazin-1-ylmethyl or 3-morpholinopropyl, and wherein any CH$_2$ or CH$_3$ group within a R$^{14}$ substituent optionally bears on each said CH$_2$ or CH$_3$ group one or more fluoro, chloro or methyl groups or a substituent selected from hydroxy, amino, methoxy, methylamino, dimethylamino, acetoxy, acetamido and N-methylacetamido, and wherein any heteroaryl or heterocyclyl group within a sub stituent on R$^{14}$ optionally bears 1, 2 or 3 substituents, which may be the same or different, selected from hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—X$^9$—R$^{17}$ wherein X$^9$ is a direct bond and R$^{17}$ is 2-fluoroethyl, 2-hydroxyethyl, 3-hydroxypropyl, 2-methoxyethyl, 3-methoxypropyl, cyanomethyl, aminomethyl, methylaminomethyl, dimethylaminomethyl, acetamidomethyl, methoxycarbonylaminomethyl, ethoxycarbonylaminomethyl or tert-butoxycarbonylaminomethyl, and wherein any heterocyclyl group within a substituent on R$^{14}$ optionally bears 1 or 2 oxo substituents.

3. A quinoline derivative of the Formula I according to claim 1 wherein:

Z$^1$ is O or NH;

m is 1 and the R$^1$ group is located at the 5-, 6- or 7-position or m is 2 and each R$^1$ group, which may be the same or different, is located at the 5- and 7-positions or at the 6- and 7-positions and R$^1$ is selected from hydroxy, amino, methyl, ethyl, propyl, butyl, methoxy, ethoxy, propoxy, isopropoxy, butoxy, pent-4-ynyloxy, hex-5-ynyloxy, methylamino, ethylamino, dimethylamino, diethylamino, acetamido, propionamido, 2-imidazol-1-ylethoxy, 2-(1,2,4-triazol-1-yl)ethoxy, tetrahydrofuran-3-yloxy, tetrahydropyran-4-yloxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2–6C)alkylene chain within a R$^1$ substituent are optionally separated by the insertion into the chain of a group selected from O, NH, N(Me), CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy, and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a $R^1$ substituent is optionally N-substituted with allyl, methylsulphonyl, acetyl, 2-fluoroethyl, 3-fluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

n is 0 or 1 and the $R^3$ group, if present, is located at the 5- or 6-position of the 1,3-benzodioxol-4-yl group and is selected from fluoro, chloro, bromo, trifluoromethyl, cyano, hydroxy, methyl, ethyl, vinyl, allyl, ethynyl, methoxy and ethoxy;

$Z^2$ is a C≡C or CH=CH group; and $R^{14}$ is selected from cyano, formyl, carboxy, carbamoyl, methoxycarbonyl, vinyl, ethoxycarbonyl N-methylcarbamoyl, N-ethylcarbamoyl, N,N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, cyanomethyl, 2-cyanoethyl, 3-cyanopropyl, methylaminomethyl, ethylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, 2-acetamidoethyl and 3-acetamidopropyl, or from a group of the formula:

—$X^7$-$Q^5$ wherein $X^7$ is a direct bond or CO and $Q^5$ is pyridin-2-yl, 1-pyrrolidinyl, morpholino, 1,1-dioxotetrahydro-4H-1,4-thiazin-4-yl, piperidino, 1-homopipendinyl, piperazin-1-yl, homopiperazin-1-yl, 1-pyrrolidinylmethyl, morpholinomethyl, piperidinomethyl, 1-homopiperidinylmethyl, 1,1-dioxotetrahydro-4H-1,4-thiazin-4-ylmethyl, piperazin-1-ylmethyl, homopiperazin-1-ylmethyl or 3-morpholinopropyl, and wherein any $CH_2$ or $CH_3$ group within a $R^{14}$ substituent optionally bears on each said $CH_2$ or $CH_3$ group one or more fluoro, chloro or methyl groups or a substituent selected from hydroxy, amino, methoxy, methylamino, dimethylamino, acetoxy, acetamido and N-methylacetamido, and wherein any heteroaryl or heterocyclyl group within a sub stituent on $R^{14}$ optionally bears 1, 2 or 3 substituents, which may be the same or different, selected from hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—$X^9$—$R^{17}$ wherein $X^9$ is a direct bond and $R^{17}$ is 2-hydroxyethyl, 3-hydroxypropyl, 2-methoxyethyl, 3-methoxypropyl, cyanomethyl, aminomethyl, methylaminomethyl, dimethylaminomethyl, acetamidomethyl, methoxycarbonylaminomethyl, ethoxycarbonylaminomethyl or tert-butoxycarbonylaminomethyl, and wherein any heterocyclyl group within a substituent on $R^{14}$ optionally bears 1 or 2 oxo substituents;

or a pharmaceutically-acceptable acid-addition salt thereof.

4. A quinoline derivative of the Formula I, or a pharmaceutically acceptable salt thereof, according to claim 1 wherein $R^1$, $R^3$, $R^{14}$, $Z^2$, m and n have any of the meanings defined in claim 1 and $Z^1$ is NH.

5. A quinoline derivative of the Formula I, or a pharmaceutically acceptable salt thereof, according to claim 1 wherein $R^1$, $R^3$, $R^{14}$, $Z^1$, m and n have any of the meanings defined in claim 1 and $Z^2$ is a C≡C group.

6. A quinoline derivative of the Formula I, or a pharmaceutically acceptable salt thereof, according to claim 1 wherein $R^1$, $R^3$, $R^{14}$, $Z^1$, $Z^2$, m and n have any of the meanings defined in claim 1 and the $Z^2$-$R^{14}$ group is located at the 7-position on the 1,3-benzodioxol-4-yl group.

7. A quinoline derivative of the Formula I according to claim 1 wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy and 2-fluoro-3-(4-hydroxypiperidin-1-yl)propoxy;

n is 0 or n is 1 and $R^3$ is a fluoro or chloro group located at the 5-position of the 1,3-benzodioxol-4-yl group;

the -$Z^2$-$R^{14}$ group is located at the 7-position on the 1,3-benzodioxol-4-yl group, $Z^2$ is a C≡C group; and $R^{14}$ is selected from vinyl, hydroxymethyl, methoxymethyl, dimethylaminomethyl, pyridin-2-yl, 1-pyrrolidinylmethyl, morpholinomethyl, piperidinomethyl, 1,1-dioxotetrahydro-4H-1,4-thiazin-4-ylmethyl and piperazin-1-ylmethyl;

or a pharmaceutically-acceptable acid-addition salt thereof.

8. A quinoline derivative of the Formula I according to claim 1 wherein
$Z^1$ is NH;
m is 2 and the first $R^1$ group is located at the 5-position and is selected from N-methylpiperidin-4-yloxy and tetrahydro-2H-pyran-4-yloxy and the second $R^1$ group is located at the 7-position and is selected from methoxy and 3-morpholinopropoxy,
n is 0 or n is 1 and $R^3$ is located at the 5-position of the 1,3-benzodioxol-4-yl group and is a chloro group;
the $-Z^2-R^{14}$ group is located at the 7-position on the 1,3-benzodioxol-4-yl group,
$Z^2$ is a C≡C group; and
$R^{14}$ is selected from methoxymethyl and 2-methoxyethyl;
or a pharmaceutically-acceptable acid-addition salt thereof.

9. A quinoline derivative of the Formula I according to claim 1 and selected from
7-[3-(4-acetylpiperazin-1-yl)propoxy]-3-cyano-6-methoxy-4-[4-(3-methoxyprop-1-ynyl)-2,3-methylenedioxyanilino]quinoline;
3-cyano-6,7-dimethoxy-4-[4-(3-methoxyprop-1-ynyl)-2,3-methylenedioxyanilino]quinoline;
3-cyano-6,7-dimethoxy-4-[6-chloro-4-(3-methoxyprop-1-ynyl)-2,3-methylenedioxy anilino]quinoline;
3-cyano-7-ethoxy-6-methoxy-4-[4-(3-methoxyprop-1-ynyl)-2,3-methylenedioxyanilino]quinoline;
3-cyano-7-{3-[4-(2-fluoroethyl)piperazin-1-yl]propoxy}-6-methoxy-4-[4-(3-methoxyprop-1-ynyl)-2,3-methylenedioxyanilino]quinoline;
3-cyano-6-methoxy-7-[3-(4-methylpiperazin-1-yl)propoxy]-4-[4-(3-methoxyprop-1-ynyl)-2,3-methylenedioxyanilino]quinoline;
3-cyano-6-methoxy-4-[4-(3-methoxyprop-1-ynyl)-2,3-methylenedioxyanilino]-7-[3-morpholinopropoxy] quinoline;
4-[6-chloro-4-(3-methoxyprop-1-ynyl)-2,3-methylenedioxyanilino]-3-cyano-6-methoxy-7-[3-morpholinopropoxy]quinoline;
3-cyano-7-[3-(1,1-dioxotetrahydro-4H-thiazin-4-yl)propoxy]-6-methoxy-4-[4-(3-methoxyprop-1-ynyl)-2,3-methylenedioxyanilino]quinoline;
3-cyano-7-(2-fluoroethoxy)-6-methoxy-4-[4-(3-methoxyprop-1-ynyl)-2,3-methylenedioxyanilino]quinoline;
3-cyano-6-methoxy-4-[4-(3-methoxyprop-1-ynyl)-2,3-methylenedioxyanilino]-7-[3-(3-oxopiperazin-1-yl)propoxy]quinoline;
3-cyano-6-methoxy-4-[6-chloro-4-(3-methoxyprop-1-ynyl)-2,3-methylenedioxyanilino]-7-[3-(3-oxopiperazin-1-yl)propoxy]quinoline;
3-cyano-6-methoxy-4-[4-(3-methoxyprop-1-ynyl)-2,3-methylenedioxyanilino]-7-[2-(2-pyrrolidin-1-ylethoxy)ethoxy]quinoline;
3-cyano-6-methoxy-7-[2-(2-methoxyethoxy)ethoxy]-4-[4-(3-methoxyprop-1-ynyl)-2,3-methylenedioxyanilino]quinoline;
3-cyano-4-[6-chloro-4-(3-methoxyprop-1-ynyl)-2,3-methylenedioxyanilino]-7-methoxy-5-[(1-methylpiperidin-4-yl)oxy]quinoline;
3-cyano-7-methoxy-5-[(1-methylpiperidin-4-yl)oxy]-4-[4-(3-methoxyprop-1-ynyl)-2,3-methylenedioxyanilino]quinoline;
3-cyano-7-(3-morpholin-4-ylpropoxy)-5-(tetrahydro-2H-pyran-4-yloxy)-4-[4-(3-methoxyprop-1-ynyl)-2,3-methylenedioxyanilino]quinoline;
3-cyano-7-methoxy-4-[4-(4-methoxybut-1-ynyl)-2,3-methylenedioxyanilino]-5-[(1-methylpiperidin-4-yl)oxy] quinoline;
4-[(4-but-3-en-1-ynyl-2,3-methylendioxy)anilino]-3-cyano-7-methoxy-5-[(1-methylpiperidin-4-yl)oxy]quinoline;
3-cyano-6-methoxy-7-[3-(4-methylpiperazin-1-yl)propoxy]-4-[6-fluoro-4-(3-methoxyprop-1-ynyl)-2,3-methylenedioxyanilino]quinoline;
3-cyano-6-methoxy-7-[2-fluoro-3-(4-hydroxypiperidin-1-yl)propoxy]-4-[4-(3-methoxyprop-1-ynyl)-2,3-methylenedioxyanilino]quinoline;
3-cyano-6-methoxy-7-[3-(4-methylpiperazin-1-yl)propoxy]-4-[4-(3-methoxyprop-1-ynyl)-2,3-methylenedioxyanilino]quinoline; and
3-cyano-6,7-dimethoxy-4-[(pyridin-2-ylethynyl)-2,3-methylenedioxyanilino]quinoline, or a pharmaceutically acceptable acid addition salt thereof.

10. A process for the preparation of a quinoline derivative of the Formula I, or a pharmaceutically-acceptable salt thereof, according to claim 1 which comprises:

(a) for the production of those compounds of the Formula I wherein $Z^1$ is an O, S or $N(R^2)$ group, the reaction of a quinoline of the Formula II

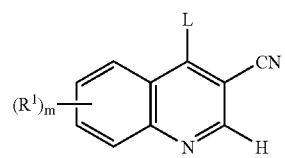

wherein L is a displaceable group and m and $R^1$ have any of the meanings defined in claim 1 except that any functional group is protected if necessary, with a compound of the Formula III

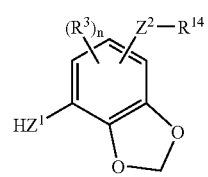

wherein $Z^1$ is O, S, or $N(R^2)$ and n, $R^3$, $R^2$, $Z^2$ and $R^{14}$ have any of the meanings defined in claim 1 except that any functional group is protected if necessary, whereafter any protecting group that is present is removed by conventional means;

(b) for the production of those compounds of the Formula I wherein at least one $R^1$ group is a group of the formula $Q^1-X^1-$ wherein $Q^1$ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group or an optionally substituted alkyl group and $X^1$ is an oxygen atom, the coupling, conveniently in the presence of a suitable dehydrating agent, of a quinoline of the Formula V

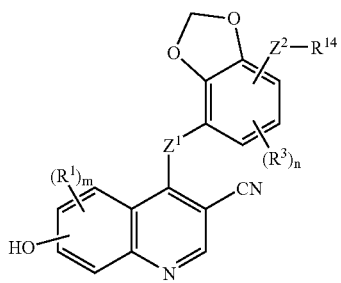

V wherein m, $R^1$, $Z^1$, n, $R^3$, $Z^2$ and $R^{14}$ have any of the meanings defined in claim 1 except that any functional group is protected if necessary, with an appropriate alcohol of the formula $Q^1$-OH wherein any functional group is protected if necessary, whereafter any protecting group that is present is removed by conventional means;

(c) for the production of those compounds of the Formula I wherein $R^1$ is an amino-substituted (1–6C)alkoxy group, the reaction of a compound of the Formula I wherein $R^1$ is a halogeno-substituted (1–6C)alkoxy group with a heterocyclyl compound or an appropriate amine;

(d) for the production of those compounds of the Formula I wherein an $R^1$ group contains a (1–6C)alkoxy or substituted (1–6C)alkoxy group or a (1–6C)alkylamino or substituted (1–6C)alkylamino group, the alkylation, conveniently in the presence of a suitable base of a quinoline derivative of the Formula I, wherein the $R^1$ group contains a hydroxy group or a primary or secondary amino group;

(e) for the production of those compounds of the Formula I wherein $Z^1$ is a SO or $SO_2$ group, wherein an $R^1$ or $R^3$ substituent is a (1–6C)alkylsulphinyl or (1–6C)alkylsulphonyl group or wherein an $R^1$, $R^3$ or $R^{14}$ substituent contains a SO or $SO_2$ group, the oxidation of a compound of Formula I wherein $Z^1$ is a S group or wherein an $R^1$ or $R^3$ substituent is a (1–6C)alkylthio group or wherein an $R^1$ $R^3$ or $R^{14}$ substituent contains a S group;

(f) the reaction of a compound of the Formula VI

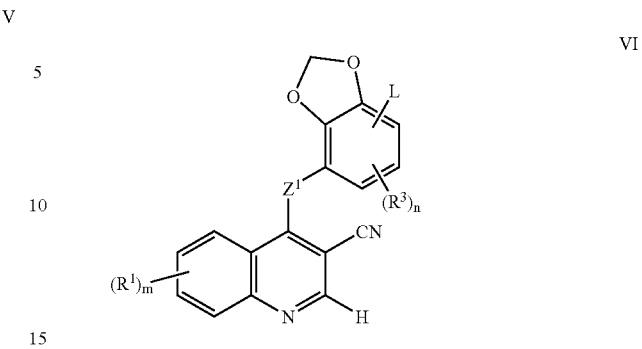

VI wherein L is a displaceable group and m, $R^1$, $Z^1$, n and $R^3$ have any of the meanings defined in claim 1 except that any functional group is protected if necessary, with a compound of the Formula VII $$HZ^2\text{-}R^{14}$$ VII wherein $Z^2$ is a C≡C or $C(R^{13})$=$C(R^{13})$ group and $R^{13}$ and $R^{14}$ have any of the meanings defined in claim 1 except that any functional group is protected if necessary, whereafter any protecting group that is present is removed by conventional means;

(g) for the production of a compound of the Formula I wherein $R^{14}$ is a carboxy group, the cleavage of a compound of the Formula I wherein $R^{14}$ is a (1–6C) alkoxycarbonyl group;

(h) the reaction of a compound of the Formula I wherein $R^{14}$ is a carboxy group with an appropriate amine to form a further compound of the Formula I wherein $R^{14}$ is a carbamoyl, N-(1–6C)alkylcarbamoyl, N,N-di-[(1–6C)alkyl]carbamoyl or heterocyclylcarbonylamino group;

and when a pharmaceutically-acceptable salt of a quinoline derivative of the Formula I is required it may be obtained using a conventional procedure.

11. A pharmaceutical composition which comprises a quinoline derivative of the Formula I, or a pharmaceutically-acceptable salt thereof, according to claim 1 in association with a pharmaceutically-acceptable diluent or carrier.

\* \* \* \* \*